US008969344B2

(12) United States Patent
Matsui et al.

(10) Patent No.: US 8,969,344 B2
(45) Date of Patent: *Mar. 3, 2015

(54) METHOD FOR ASSAY ON THE EFFECT OF VASCULARIZATION INHIBITOR

(71) Applicants: Junji Matsui, Ibaraki (JP); Yuji Yamamoto, Ibaraki (JP); Toshimitsu Uenaka, Ibaraki (JP)

(72) Inventors: Junji Matsui, Ibaraki (JP); Yuji Yamamoto, Ibaraki (JP); Toshimitsu Uenaka, Ibaraki (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 73 days.

This patent is subject to a terminal disclaimer.

(21) Appl. No.: 13/624,278

(22) Filed: Sep. 21, 2012

(65) Prior Publication Data

US 2013/0085152 A1    Apr. 4, 2013

Related U.S. Application Data

(62) Division of application No. 11/997,719, filed as application No. PCT/JP2006/315698 on Aug. 2, 2006.

(30) Foreign Application Priority Data

Aug. 2, 2005   (JP) .................. 2005-224173
Jun. 14, 2006  (JP) .................. 2006-164700

(51) Int. Cl.
| | | |
|---|---|---|
| A61K 31/517 | (2006.01) | |
| A61K 31/535 | (2006.01) | |
| A61K 31/47 | (2006.01) | |
| G01N 33/50 | (2006.01) | |
| G01N 33/574 | (2006.01) | |

(52) U.S. Cl.
CPC .............. *A61K 31/517* (2013.01); *A61K 31/47* (2013.01); *G01N 33/5011* (2013.01); *G01N 33/574* (2013.01); *G01N 2333/485* (2013.01); *G01N 2333/515* (2013.01)
USPC .................... 514/234.8; 514/266.22; 514/312

(58) Field of Classification Search
None
See application file for complete search history.

(56) References Cited

U.S. PATENT DOCUMENTS

| | | | |
|---|---|---|---|
| 4,526,988 A | 7/1985 | Hertel et al. |
| 4,563,417 A | 1/1986 | Albarella et al. |
| 4,582,789 A | 4/1986 | Sheldon, III et al. |
| 4,742,003 A | 5/1988 | Derynck et al. |
| 4,764,454 A | 8/1988 | Ichijima et al. |
| 5,180,818 A | 1/1993 | Cech et al. |
| 5,445,934 A | 8/1995 | Fodor et al. |
| 5,464,826 A | 11/1995 | Grindey et al. |
| 5,487,889 A | 1/1996 | Eckert et al. |
| 5,624,937 A | 4/1997 | Reel et al. |
| 5,656,454 A | 8/1997 | Lee et al. |
| 5,658,374 A | 8/1997 | Glover |
| 5,733,913 A | 3/1998 | Blankley et al. |
| 5,747,651 A | 5/1998 | Lemischka |
| 5,750,376 A | 5/1998 | Weiss et al. |
| 5,770,599 A | 6/1998 | Gibson |
| 5,792,783 A | 8/1998 | Tang et al. |
| 5,891,996 A | 4/1999 | Mateo de Acosta del Rio et al. |
| 5,948,438 A | 9/1999 | Staniforth et al. |
| 6,027,880 A | 2/2000 | Cronin et al. |
| 6,057,100 A | 5/2000 | Heyneker |
| 6,143,764 A | 11/2000 | Kubo et al. |
| 6,156,501 A | 12/2000 | McGall et al. |
| 6,156,522 A | 12/2000 | Keay et al. |
| 6,217,866 B1 | 4/2001 | Schlessinger et al. |
| 6,261,776 B1 | 7/2001 | Pirrung et al. |
| 6,346,398 B1 | 2/2002 | Pavco et al. |
| 6,476,040 B1 | 11/2002 | Norris et al. |
| 6,524,583 B1 | 2/2003 | Thorpe et al. |
| 6,534,535 B1 | 3/2003 | Zhu et al. |
| 6,576,424 B2 | 6/2003 | Fodor et al. |
| 6,676,941 B2 | 1/2004 | Thorpe et al. |
| 6,762,180 B1 | 7/2004 | Roth et al. |
| 6,797,823 B1 | 9/2004 | Kubo et al. |
| 6,811,779 B2 | 11/2004 | Rockwell et al. |
| 6,812,341 B1 | 11/2004 | Conrad |
| 6,821,987 B2 | 11/2004 | Kubo et al. |
| 7,005,430 B2 | 2/2006 | Ueno et al. |
| 7,101,663 B2 | 9/2006 | Godfrey et al. |
| 7,135,466 B2 | 11/2006 | Sakai et al. |
| 7,169,789 B2 | 1/2007 | Kubo et al. |
| 7,253,286 B2 | 8/2007 | Funahashi et al. |

(Continued)

FOREIGN PATENT DOCUMENTS

| | | |
|---|---|---|
| CN | 1473041 | 2/2004 |
| CN | 1478078 | 2/2004 |

(Continued)

OTHER PUBLICATIONS

Response to Office Action for CN200880115011.7 dated Nov. 20, 2012 with English translation.
Office Action for U.S. Appl. No. 13/083,338 dated Nov. 23, 2012.
Response to Office Action for JP2011-527665 dated May 10, 2012 with English translation.
Explanation of Circumstances re Accelerated Examination filed for JP2011-527665 dated May 10, 2012 with English translation.

(Continued)

*Primary Examiner* — Karen Canella
(74) *Attorney, Agent, or Firm* — Fish & Richardson P.C.

(57) ABSTRACT

The present invention provides a method of predicting the antitumor effect of an angiogenesis inhibitor. It is possible to predict the antitumor effect of an angiogenesis inhibitor by evaluating the EOF dependency of a tumor cell for proliferation and/or survival and using the EGF dependency as an indicator. Since the antitumor effect of an angiogenesis inhibitor correlates with the EGF dependency of a tumor cell for proliferation and/or survival, the angiogenesis inhibitors is capable of producing excellent antitumor effect when combined with a substance having EGF inhibitory activity.

4 Claims, 5 Drawing Sheets

(56) References Cited

U.S. PATENT DOCUMENTS

| | | |
|---|---|---|
| 7,435,590 B2 | 10/2008 | Komurasaki |
| 7,485,658 B2 | 2/2009 | Bolger et al. |
| 7,495,104 B2 | 2/2009 | Miwa et al. |
| 7,550,483 B2 | 6/2009 | Sakaguchi et al. |
| 7,612,092 B2 | 11/2009 | Funahashi et al. |
| 7,612,208 B2 | 11/2009 | Matsushima et al. |
| 7,759,518 B2 | 7/2010 | Maderna et al. |
| 7,820,664 B2 | 10/2010 | Vernier et al. |
| 7,846,941 B2 | 12/2010 | Zhang et al. |
| 7,855,290 B2 | 12/2010 | Matsushima et al. |
| 7,863,288 B2 | 1/2011 | Ibrahim et al. |
| 7,973,160 B2 | 7/2011 | Funahashi et al. |
| 8,044,240 B2 | 10/2011 | Dimock |
| 8,063,049 B2 | 11/2011 | Koh et al. |
| 8,101,799 B2 | 1/2012 | Maderna et al. |
| 8,143,271 B2 | 3/2012 | Ibrahim et al. |
| 8,252,842 B2 | 8/2012 | Dimock |
| 8,288,538 B2 | 10/2012 | Matsushima et al. |
| 8,372,981 B2 | 2/2013 | Funahashi et al. |
| 8,377,938 B2 | 2/2013 | Matsushima et al. |
| 8,415,469 B2 | 4/2013 | Ibrahim et al. |
| 8,466,316 B2 | 6/2013 | Dimock |
| 8,470,818 B2 | 6/2013 | Ibrahim et al. |
| 8,580,254 B2 | 11/2013 | Adam et al. |
| 8,648,116 B2 | 2/2014 | Vernier et al. |
| 8,759,577 B2 | 6/2014 | Dimock |
| 8,808,742 B2 | 8/2014 | Quart et al. |
| 2002/0010203 A1 | 1/2002 | Lipson et al. |
| 2002/0040127 A1 | 4/2002 | Jiang et al. |
| 2003/0013208 A1 | 1/2003 | Jendoubi |
| 2003/0087907 A1 | 5/2003 | Kubo et al. |
| 2003/0113713 A1 | 6/2003 | Glezer et al. |
| 2003/0215523 A1 | 11/2003 | Ozawa et al. |
| 2004/0009965 A1 | 1/2004 | Collins et al. |
| 2004/0034026 A1 | 2/2004 | Wood et al. |
| 2004/0053908 A1 | 3/2004 | Funahashi et al. |
| 2004/0086915 A1 | 5/2004 | Lin et al. |
| 2004/0132727 A1 | 7/2004 | Sakai et al. |
| 2004/0152759 A1 | 8/2004 | Abrams et al. |
| 2004/0167134 A1 | 8/2004 | Bruns et al. |
| 2004/0171068 A1 | 9/2004 | Wehland et al. |
| 2004/0191254 A1 | 9/2004 | Fagin |
| 2004/0229876 A1 | 11/2004 | Kubo et al. |
| 2004/0242506 A1 | 12/2004 | Barges Causeret et al. |
| 2004/0253205 A1 | 12/2004 | Yamamoto et al. |
| 2004/0259834 A1 | 12/2004 | Kasprzyk et al. |
| 2005/0014727 A1 | 1/2005 | Muller et al. |
| 2005/0049264 A1 | 3/2005 | Miwa et al. |
| 2005/0119303 A1 | 6/2005 | Wakabayashi et al. |
| 2005/0176802 A1 | 8/2005 | Tang et al. |
| 2005/0187236 A1 | 8/2005 | Tsuruoka et al. |
| 2005/0209452 A1 | 9/2005 | Bornsen et al. |
| 2005/0272688 A1 | 12/2005 | Higgins et al. |
| 2005/0277652 A1 | 12/2005 | Matsushima et al. |
| 2005/0288521 A1 | 12/2005 | Naidu et al. |
| 2006/0004017 A1 | 1/2006 | Stokes et al. |
| 2006/0004029 A1 | 1/2006 | Tsuruoka et al. |
| 2006/0057195 A1 | 3/2006 | Nonomura et al. |
| 2006/0079494 A1 | 4/2006 | Santi et al. |
| 2006/0135486 A1 | 6/2006 | Owa et al. |
| 2006/0160832 A1 | 7/2006 | Funahashi et al. |
| 2006/0189629 A1 | 8/2006 | Bolger et al. |
| 2006/0292192 A1 | 12/2006 | Hasenzahl et al. |
| 2007/0004773 A1 | 1/2007 | Sakaguchi et al. |
| 2007/0027318 A1 | 2/2007 | Kubo et al. |
| 2007/0032521 A1 | 2/2007 | Moussy et al. |
| 2007/0037849 A1 | 2/2007 | Naito et al. |
| 2007/0078159 A1 | 4/2007 | Matsushima |
| 2007/0117842 A1 | 5/2007 | Arimoto et al. |
| 2008/0214604 A1 | 9/2008 | Furitsu et al. |
| 2008/0241835 A1 | 10/2008 | Mehraban et al. |
| 2009/0047278 A1 | 2/2009 | Owa et al. |
| 2009/0047365 A1 | 2/2009 | Owa et al. |
| 2009/0053236 A1 | 2/2009 | Yamamoto et al. |
| 2009/0202541 A1 | 8/2009 | Bruns et al. |
| 2009/0247576 A1 | 10/2009 | Kamata et al. |
| 2009/0264464 A1 | 10/2009 | Yamamoto et al. |
| 2009/0304694 A1 | 12/2009 | Oliner et al. |
| 2010/0048503 A1 | 2/2010 | Yamamoto |
| 2010/0048620 A1 | 2/2010 | Yamamoto et al. |
| 2010/0092490 A1 | 4/2010 | Uenaka et al. |
| 2010/0105031 A1 | 4/2010 | Matsui et al. |
| 2010/0239688 A1 | 9/2010 | Yamamoto |
| 2010/0324087 A1 | 12/2010 | Yamamoto |
| 2011/0118470 A1 | 5/2011 | Funahashi et al. |
| 2011/0158983 A1 | 6/2011 | Bascomb et al. |
| 2011/0166174 A1 | 7/2011 | Zhang et al. |
| 2011/0293615 A1 | 12/2011 | Yamamoto |
| 2012/0022076 A1 | 1/2012 | Maderna et al. |
| 2012/0077842 A1 | 3/2012 | Bando |
| 2012/0207753 A1 | 8/2012 | Yu et al. |
| 2012/0219522 A1 | 8/2012 | Xi |
| 2012/0244209 A1 | 9/2012 | Roth et al. |
| 2012/0263677 A1 | 10/2012 | Eagle et al. |
| 2012/0283206 A1 | 11/2012 | Bruns et al. |
| 2013/0123274 A1 | 5/2013 | Nakagawa et al. |
| 2013/0296365 A1 | 11/2013 | Bando |

FOREIGN PATENT DOCUMENTS

| | | |
|---|---|---|
| CN | 1890220 | 1/2007 |
| CN | 101001629 | 7/2007 |
| CN | 101029022 | 9/2007 |
| CN | 101198590 | 6/2008 |
| CN | 101316590 | 12/2008 |
| CN | 101454311 | 6/2009 |
| CN | 101616621 | 12/2009 |
| CN | 102470133 | 5/2012 |
| EP | 297580 | 1/1989 |
| EP | 405425 | 1/1991 |
| EP | 602851 | 6/1994 |
| EP | 684820 | 6/1995 |
| EP | 795556 | 9/1997 |
| EP | 837063 | 4/1998 |
| EP | 870842 | 10/1998 |
| EP | 930305 | 7/1999 |
| EP | 930310 | 7/1999 |
| EP | 1029853 | 8/2000 |
| EP | 1044969 | 10/2000 |
| EP | 543942 | 1/2001 |
| EP | 1153920 | 11/2001 |
| EP | 712863 | 2/2002 |
| EP | 1331005 | 7/2003 |
| EP | 1382604 | 1/2004 |
| EP | 1411046 | 4/2004 |
| EP | 1415987 | 5/2004 |
| EP | 1447405 | 1/2005 |
| EP | 1506962 | 2/2005 |
| EP | 1522540 | 4/2005 |
| EP | 1535910 | 6/2005 |
| EP | 1552833 | 7/2005 |
| EP | 1566379 | 8/2005 |
| EP | 1604665 | 12/2005 |
| EP | 1683785 | 7/2006 |
| EP | 1698623 | 9/2006 |
| EP | 1797877 | 6/2007 |
| EP | 1797881 | 6/2007 |
| EP | 1859797 | 11/2007 |
| EP | 1894918 | 3/2008 |
| EP | 1925676 | 5/2008 |
| EP | 1925941 | 5/2008 |
| EP | 1949902 | 7/2008 |
| EP | 1964837 | 9/2008 |
| EP | 2116246 | 11/2009 |
| EP | 2119707 | 11/2009 |
| EP | 2133094 | 12/2009 |
| EP | 2133095 | 12/2009 |
| EP | 2218712 | 8/2010 |
| GB | 2253848 | 9/1992 |
| IN | 236500 | 11/2009 |
| JP | S63-028427 | 2/1988 |
| JP | 01-022874 | 1/1989 |
| JP | 02-291295 | 12/1990 |
| JP | 04-341454 | 11/1992 |

(56) References Cited

FOREIGN PATENT DOCUMENTS

| | | |
|---|---|---|
| JP | 06-153952 | 6/1994 |
| JP | 07-176103 | 7/1995 |
| JP | 08-045927 | 2/1996 |
| JP | 08-048078 | 2/1996 |
| JP | 09-023885 | 1/1997 |
| JP | 09-234074 | 9/1997 |
| JP | 11-501343 | 2/1999 |
| JP | 11-143429 | 5/1999 |
| JP | 11-158149 | 6/1999 |
| JP | 11-322596 | 11/1999 |
| JP | 3040486 | 3/2000 |
| JP | 3088018 | 7/2000 |
| JP | 2000-328080 | 11/2000 |
| JP | 2001-131071 | 5/2001 |
| JP | 2002-003365 | 1/2002 |
| JP | 2002-114710 | 4/2002 |
| JP | 2002-536414 | 10/2002 |
| JP | 2003-012668 | 1/2003 |
| JP | 2003-026576 | 1/2003 |
| JP | 3420549 | 4/2003 |
| JP | 2003-525595 | 9/2003 |
| JP | 2004-513964 | 5/2004 |
| JP | 2004-155773 | 6/2004 |
| JP | 2004-531549 | 10/2004 |
| JP | 2005-501074 | 1/2005 |
| JP | 2005-504111 | 2/2005 |
| JP | 2005-520834 | 7/2005 |
| JP | 3712393 | 8/2005 |
| JP | 2005-272474 | 10/2005 |
| JP | 2006-508981 | 3/2006 |
| JP | 2006-515884 | 6/2006 |
| JP | 2008-546797 | 10/2008 |
| JP | 2010-535233 | 11/2010 |
| KR | 10-0589032 | 6/2006 |
| WO | 86/03222 | 6/1986 |
| WO | 92/20642 | 11/1992 |
| WO | 94/09010 | 4/1994 |
| WO | 95/15758 | 6/1995 |
| WO | 95/19774 | 7/1995 |
| WO | 96/09294 | 3/1996 |
| WO | 96/26997 | 9/1996 |
| WO | 96/30347 | 10/1996 |
| WO | 96/33980 | 10/1996 |
| WO | 96/39145 | 12/1996 |
| WO | 96/40142 | 12/1996 |
| WO | 97/03069 | 1/1997 |
| WO | 97/13760 | 4/1997 |
| WO | 97/13771 | 4/1997 |
| WO | 97/17329 | 5/1997 |
| WO | 97/21437 | 6/1997 |
| WO | 97/38984 | 10/1997 |
| WO | 97/48693 | 12/1997 |
| WO | 98/00134 | 1/1998 |
| WO | 98/02434 | 1/1998 |
| WO | 98/02437 | 1/1998 |
| WO | 98/02438 | 1/1998 |
| WO | 98/13350 | 4/1998 |
| WO | 98/14437 | 4/1998 |
| WO | 98/23613 | 6/1998 |
| WO | 98/32436 | 7/1998 |
| WO | 98/35958 | 8/1998 |
| WO | 98/37079 | 8/1998 |
| WO | 98/50346 | 11/1998 |
| WO | 98/52558 | 11/1998 |
| WO | 99/00357 | 1/1999 |
| WO | 99/32106 | 7/1999 |
| WO | 99/32110 | 7/1999 |
| WO | 99/32111 | 7/1999 |
| WO | 99/32436 | 7/1999 |
| WO | 99/35132 | 7/1999 |
| WO | 99/35146 | 7/1999 |
| WO | 99/43654 | 9/1999 |
| WO | 99/62890 | 12/1999 |
| WO | 00/31048 | 6/2000 |
| WO | 00/42012 | 7/2000 |
| WO | 00/43366 | 7/2000 |
| WO | 00/43384 | 7/2000 |
| WO | 00/44728 | 8/2000 |
| WO | 00/47212 | 8/2000 |
| WO | 00/50405 | 8/2000 |
| WO | 00/71097 | 11/2000 |
| WO | 01/02369 | 1/2001 |
| WO | 01/23375 | 4/2001 |
| WO | 01/27081 | 4/2001 |
| WO | 01/32926 | 5/2001 |
| WO | 01/36403 | 5/2001 |
| WO | 01/40217 | 6/2001 |
| WO | 01/45689 | 6/2001 |
| WO | 01/47890 | 7/2001 |
| WO | 01/47931 | 7/2001 |
| WO | 01/60814 | 8/2001 |
| WO | 02/16348 | 2/2002 |
| WO | 02/32872 | 4/2002 |
| WO | 02/36117 | 5/2002 |
| WO | 02/41882 | 5/2002 |
| WO | 02/44156 | 6/2002 |
| WO | 02/072578 | 9/2002 |
| WO | 02/080975 | 10/2002 |
| WO | 02/088110 | 11/2002 |
| WO | 02/092091 | 11/2002 |
| WO | 03/006462 | 1/2003 |
| WO | 03/013529 | 2/2003 |
| WO | 03/024386 | 3/2003 |
| WO | 03/027102 | 4/2003 |
| WO | 03/028711 | 4/2003 |
| WO | 03/033472 | 4/2003 |
| WO | 03/050090 | 6/2003 |
| WO | 03/074045 | 9/2003 |
| WO | 03/079020 | 9/2003 |
| WO | 2004/006862 | 1/2004 |
| WO | 2004/020434 | 3/2004 |
| WO | 2004/032872 | 4/2004 |
| WO | 2004/032937 | 4/2004 |
| WO | 2004/035052 | 4/2004 |
| WO | 2004/039782 | 5/2004 |
| WO | 2004/041308 | 5/2004 |
| WO | 2004/043472 | 5/2004 |
| WO | 2004/045523 | 6/2004 |
| WO | 2004/064730 | 8/2004 |
| WO | 2004/078144 | 9/2004 |
| WO | 2004/080462 | 9/2004 |
| WO | 2004/080966 | 9/2004 |
| WO | 2004/101526 | 11/2004 |
| WO | 2005/004870 | 1/2005 |
| WO | 2005/021537 | 3/2005 |
| WO | 2005/027972 | 3/2005 |
| WO | 2005/030140 | 4/2005 |
| WO | 2005/044788 | 5/2005 |
| WO | 2005/051366 | 6/2005 |
| WO | 2005/056764 | 6/2005 |
| WO | 2005/063713 | 7/2005 |
| WO | 2005/082854 | 9/2005 |
| WO | 2005/092896 | 10/2005 |
| WO | 2005/117887 | 12/2005 |
| WO | 2006/030826 | 3/2006 |
| WO | 2006/030941 | 3/2006 |
| WO | 2006/030947 | 3/2006 |
| WO | 2006/062984 | 6/2006 |
| WO | 2006/090930 | 8/2006 |
| WO | 2006/090931 | 8/2006 |
| WO | 2006/036941 | 12/2006 |
| WO | 2006/137474 | 12/2006 |
| WO | 2007/000347 | 1/2007 |
| WO | 2007/014335 | 2/2007 |
| WO | 2007/015569 | 2/2007 |
| WO | 2007/015578 | 2/2007 |
| WO | 2007/023768 | 3/2007 |
| WO | 2007/040565 | 4/2007 |
| WO | 2007/052849 | 5/2007 |
| WO | 2007/052850 | 5/2007 |
| WO | 2007/061127 | 5/2007 |
| WO | 2007/061130 | 5/2007 |
| WO | 2007/136103 | 11/2007 |
| WO | 2008/023698 | 2/2008 |

(56) References Cited

FOREIGN PATENT DOCUMENTS

| WO | 2008/026748 | 3/2008 |
|---|---|---|
| WO | 2008/088088 | 7/2008 |
| WO | 2008/093855 | 8/2008 |
| WO | 2009/060945 | 5/2009 |
| WO | 2009/077874 | 6/2009 |
| WO | 2009/096377 | 8/2009 |
| WO | 2009/140549 | 11/2009 |
| WO | 2010/006225 | 1/2010 |
| WO | 2011/017583 | 2/2011 |
| WO | 2011/022335 | 2/2011 |
| WO | 2011/162343 | 12/2011 |

OTHER PUBLICATIONS

Office Action for IN 1571/CHENP/2007 dated Oct. 30, 2012.
Office Action for AU 2008325608 dated Nov. 24, 2012.
Office Action for EP 07743994.1 dated Oct. 10, 2012.
Response to Office Action for IL 200090 dated Dec. 23, 2012 (with English language translation).
European Search Report for EP 10809938.3 dated Jan. 2, 2013.
Office Action for CN 201080030508.6 dated Nov. 30, 2012 with English translation.
Response to Office Action for EP 08704376.6 dated Jan. 2, 2013.
Response to Office Action for EP 08846814.5 dated Jan. 3, 2013.
Office Action for U.S. Appl. No. 13/083,338 dated Jan. 3, 2013.
Clinical Trial: AMG 706 20040273 Thyroid Cancer Study, Stage 4 Cancer Treatments, Chat w/a Cancer Info Expert About Stage 4 Cancer Treatment Options. Www.CancerCenter.com, Jul. 2005.
Polverino et al., "AMG 706, an Oral, Multikinase Inhibitor that Selectively Targets Vascular Endothelial Growth Factor, Platelet-Derived Growth Factor, and Kit Receptors, Potently Inhibits Angiogenesis and Induces Regression in Tumor Xenografts", Cancer Research, 66(1):8715-8721, Sep. 1, 2006.
Office Action for IL 205512 dated Dec. 20, 2012 with English translation.
Submission to European Patent Office for EP03791389.4 dated Dec. 20, 2012.
Communication from Israel Patent Office for IL 175363 dated Jan. 2, 2013 with English translation.
Notice of Allowance for U.S. Appl. No. 12/524,754 dated Jan. 18, 2013.
Amendment submitted for Korean Application No. 10-2009-7017694 dated Jan. 18, 2013 with English translation.
Response to Office Action for U.S. Appl. No. 13/322,961 dated Jan. 25, 2013.
Decision of Patent Grant for JP2008-516724 dated Jan. 22, 2013 with English translation.
Office Action for JP2008-556208 dated Jan. 22, 2013 with English translation.
Office Action for CN 200980103218.7 dated Sep. 29, 2012 with English translation.
Examination Report for NZ Patent Application No. 598291 dated Oct. 15, 2012.
European Search Report for EP 12195436.6 dated Feb. 21, 2013.
English translation of Office Action dated Jan. 2, 2013 for Israel Patent Application No. 175363.
Amendment for New Zealand Patent Application No. 598291 dated Jan. 30, 2013.
Amendment for Chinese Patent Application No. 201080030508.6 dated Feb. 7, 2013 with English translation.
"NCBI GenBank Accession No. NM_000222", Feb. 11, 2008.
Australian Office Action for Application No. AU2006309551 issued on Apr. 28, 2011.
Australian Response to Office Action for Application No. 2006309551 filed on Jan. 27, 2012.
Australian Office Action for Application No. 2006309551 issued on Feb. 2, 2012.
Chinese Office Action for Application No. 200680041355.9 issued on Mar. 5, 2010 with English translation.
Chinese Response to Office Action for Application No. 200680041355.9 filed on Jul. 19, 2010 with English translation.
Chinese Office Action for Application No. 200680041355.9 issued on Aug. 24, 2010 with English translation.
Chinese Response to Office Action for Application No. 200680041355.9 filed on Nov. 8, 2010 with English translation.
"Proceedings of the American Association for Cancer Research", vol. 45, Mar. 2004, p. 1070-p. 1071.
"Redefining the Frontiers of Science 94th Annual Meeting", American Association for Cancer Research, 2003, vol. 44, Washington D.C., USA, Jul. 11-14, 2003.
"Types of Lung Cancer", Cancer care, Inc., Cancer care, Inc., Aug. 13, 2009.
Abuzar, S. et al., "Synthesis of some new 7-chloro-4-substituted quinolines as potential antiparasitic agents", Eur. J. Med. Chem.,vol. 21,No. 1, 1986, p. 5-p. 8.
Agarwal et al., "Binding of Discoidin Domain Receptor 2 to Collagen I: An Atomic Force Microscopy Investigation", Biochemistry 41:11091-11098 (2002).
Alvares Da Silva et al., "A Novel Germ-Line Point Mutation in RET Exon 8 (Gly533Cys) in a Large Kindred with Familial Medullary Thyroid Carcinoma" The Journal of Clinical Endocrinology & Metabolism 88(11):5438-5443 (Nov. 2003).
Abrams et al., "SU11248 Inhibits Kit and Platelet-derived Growth Factor Receptor Beta in Preclinical Models of Human Small Cell Lung Cancer", Molecular Cancer Therapeutics., 2: 471-478, 2003.
Anonymous, Scientific Discussion, Internet Citation, Jan. 1, 2004, p. 1/61-p. 61/61, XP007918143.
Asuno-Shinyaku, "The New Drugs of Tomorrow", Update Summary Dec. 2006 with English translation (14 pages).
Baker et al., "Blockade of Vascular Endothelial Growth Factor Receptor and Epidermal Growth Factor Receptor Signaling for Therapy of Metastatic Human Pancreatic Cancer", Cancer Research 62: 1996-2003 (2002).
Bastin et al., "Salt Selection and Optmiisation for Pharmaceutical New Chemical Entities,"Organic Process Research and Development, Cambridge, GB, vol. 4, No. 5, Jan. 1, 2000, p. 427-p. 435, XP002228592.
Bellone, et al., "Growh Stimulation of Colorectal Carcinoma Cells via the c-kit Rector is Inhibited by TGF-β-1", Journal of Cellular Physiology,172, 1997, p. 1-p. 11.
Benjamin et al., "Selective ablation of immature blood vessels in established human tumors follows vascular endothelial growth factor withdrawal", The J. of Clin. Invest. 103(2):159-165 (1999).
Berdel, et al, "Recombinant Human Stem Cell Factor Stimulates Growth of a Human Glioblastoma Cell Line Expressing c-kit Protooncogene", Cancer Research, 52, 1992, p. 3498-p. 3502.
Berge et al., Journal of Pharmaceutical Sciences, American Pharmaceutical Association, Washington, US, vol. 66, No. 1, Jan. 1, 1977, p. 1-p. 19, XP002550655.
Bergers et al., "Benefits of targeting both pericytes and endothelial cells in the tumor vasculature with kinase inhibitors", The Journal of Clinical Investigation 111(9):1287-1295 (2003).
Blume-Jensen, et al., "Activation of the Human c-kit Product by Ligand-Induced Dimerization Mediates Circular Actin Reorganization and Chemotaxis", The EMBO Journal, 10(13), 1991, p. 4121-p. 4128.
Boissan, et al., "c-Kit and c-kit mutations in mastocytosis and other hematological diseaseas", J. Leukocyte Biol., 67:135-148, (2000).
Bradley Anderson et al., "Preparation of Water-soluble Compounds through Salt Formation", The Practice of Medicinal Chemistry, Technomics, pp. 347-349, 355-356 (1999).
Bruns et al., "Effect of the Vascular Endothelial Growth Factor Receptor-2 Antibody DC101 Plus Gemcitabine on Growth, Metastasis and Angiogenesis of Human Pancreatic Cancer Growing Orthotopically in Nude Mice", Int. J. Cancer 102:101-108 (2002).
Bussolino, et al, "Role of Soluble Mediators in Angiogenesis", Eur. J. Cancer, 32A(14):, 1996, p. 2401-p. 2412.
Cairns et al., "New antiallergic pyrano[3,2g]quinoline-2,8-dicarboxylic acids with potential for the topical treatment of asthma", Cairns et al, Journal of Medicinal Chemistry 8(12), 1985, p. 1832-p. 1842.

(56) References Cited

OTHER PUBLICATIONS

Capellen et al., "Frequent activating mutations of FGFR3 in human bladder and cervix carcinomas", Nature Genetics, 23:18-20 (1999).
Carlomagno et al., "Bay 43-9006 Inhibition of Oncogenic RET Mutants", Journal of the National Cancer Institute 98(5):326-334 (2006).
Carlomagno et al., "ZD6474, an Orally Available Inhibitor of KDR Tyrosine Kinase Actvity, Efficiently Blocks Oncogenic RET Kinases", Cancer Research 62:7284-7290 (2002).
Chen et al., "FGFR3 as a therapeutic target of the small molecule inhibitor PKC412 in hematopoietic malignancies", Oncogene 24:8259-8267 (2005).
Carter et al, "Inhibition of drug-resistant mutants of ABL, KIT and EGF receptor kinases", Proceedings of the National Academy of Sciences of the United States of America., 102, 11011-11016, 2005.
Chesi et al., "Activated fibroblast growth factor receptor 3 is an oncogene that contributes to tumor progression in mulitple myeloma", Blood 97(3):729-736 (2001).
Chesi et al., "Frequent translocation t(4;14)(p16.3;q32.3) in multiple myeloma is associated with increased expression and activating mutations of fibroblast growth factor receptor", Nature Genetics, 3 16:260-264 (1997).
Ciardiello, et al., "ZD1839 (IRESSA), An EGFR-Selective Tyrosine Kinase Inhibitor, Enhances Taxane Activity in BCL-2 Overexpressing, Multidrug Resistant MCF-7 ADR Human Breast Cancer Cells", Int. J. Cancer, 98:463-469, (2002).
Clark et al., "Safety and Pharmacokinetics of the Dual Action Raf Kinase and Vascular Endothelial Growth Factor Rector Inhibitor, BAY43-9006, in Patients with Advanced Refractory Solid Tumors", Clin. Cancer Res. (2005)11:, 2005, p. 5472-p. 5480.
Chinese Office Action directed at application No. 200580026468.7 issued on Jun. 26, 2009, 6 pages.
Chinese Office Action directed at application No. 200710007097.9 issued on Mar. 6, 2009, 5 pages.
Chinese Office Action directed at application No. 200880003336.6, issued on May 24, 2011 (with English Translation).
CN200780032071.8 Office Action issued on Oct. 13, 2010 with English translation.
CN200780032071.8 Response to Office Action filed on Feb. 16, 2011 with English translation.
Cohen, et al., "Expression of Stem Cell Factor and c-kit in Human Neuroblastoma", Blood, 84(10):3465-3472 (1994).
Corbin et al., "Sensitivity of oncogenic KIT mutants to the kinase inhibitors MLN518 and PD180970", Blood., 104, 3754-3757, 2004.
Croom, et al., "Imatinib mesylate in the Treatment of Gastrointestinal Stromal Tumours", Drugs, 63(5), 2003, p. 513-p. 522.
Deplanque, et al., "Anti-Angiogenic Agents: Clinical Trial Design and Therapies in Development", European Journal of Cancer, 36, 2000, p. 1713-p. 1724.
EP07806561.2 Office Actions issued on Jan. 19 and Feb. 7, 2011.
EP07806561.2 Response to Office Action filed on Aug. 9, 2011.
EP07806561.2 Office Action issued on Dec. 9, 2011.
EESR directed at application No. 06832529.9 issued on Jul. 29, 2009, 6 pages.
Elisei et al., "Identification of a Novel Point Mutation in the RET Gene (Ala883Thr), Which Is Associated with Medullary Thyroid Carcinoma Phenotype Only in Homozygous Condition", The Journal of Clinical Endocrinology & Metabolism 89(11):5823-5827 (2004).
Erber et al., "Combined inhibition ofVEGF- and PDGF-signaling enforces tumor vessel regression by interfering with pericytemediated endothelial cell survival mechanisms", The FASEB Journal published online Dec. 4, 2003 (25 pages).
European Office Action for Application No. 06832529.9 issued on Oct. 15, 2009.
European Response to Office Action for Application No. 06832529.9 filed on Apr. 22, 2010.
European Office Action for Application No. 06832529.9 issued on Sep. 12, 2011.
European Response to Office Action for Application No. 06832529.9 filed on Oct. 4, 2011.
EP Communication under Rule 71(3) EPC for Application No. 06832529.9 issued on Nov. 25, 2011.
European Search Report for Application No. 04807580.8 dated Apr. 18, 2011 (9 pages).
European Search Report for Application No. 06767145.3 dated May 23, 2011 (7 pages).
European Search Report for Application No. 06768437.3 dated Oct. 11, 2010 (10 pages).
European Search Report for Application No. 06833681.7 dated Nov. 24, 2010, 15 pages.
European Search Report for Application No. 07806561.2 dated Jan. 19, 2011 (16 pages).
European Search Report for EP Appl. No. 06782407, Jul. 23, 2010.
European Search Report for EP Appl. No. 07743994.1 dated May 12, 2010.
European Search Report for Application No. 10015141.4 dated Sep. 9, 2011.
Experimental and Molecular Therapeutices 30, Proceedings of the American Association for Cancer Research, vol. 47 (2006).
Folkman, et al., "Angiogenesis", The Journal of Biological Chemistry, 267(16), 1992, p. 10931-p. 10934.
Folkman, et al., "Clinical Applications of Research on Angiogenesis", The New England Journal of Medicine, 333(26), 1995, p. 1757-p. 1763.
Folkman, J., "New Perspective in Clinical Oncology From Angiogenesis Research", Eur J. Cancer. 32A(14), 1996, p. 2534-p. 2539.
Folkman, J., "What is the Evidence That Tumors are Angiogenesis Dendent?", Journal of the National Cancer Institute, 82(1), 1990, p. 4-p. 6.
Furitsu et al., "Stable medicinal compositions of quinolinecarboxamide derivative", Database Caplus Chemical Abstracts Service, Columbus, Ohio, US, 2006, XP002520305.
Furitsu, et al., "Identification of Mutations in the Coding Sequence of the Proto-Oncogene c-kit in a Human Mast Cell Leukemia Cell Line Causing Ligand-Indendent Activation of c-kit Product", J. Clin. Invest. 92, 1993, p. 1736-p. 1744.
Furuta, et al., "Synthesis and Biological Evaluation of Selective Inhibitors of PDGF Rector Auto Phosphorylation", Pharmaceutical Research Laboratories, Kirin Brewery Co., Ltd. Takasaki, Gunma, Japan (Sep. 7, 2003).
Gall-Istok, et al., "Abstract of Acta Chimica Hungarica", Inst. Exp. Med., Hung. Avad. Svi., Budapest, 1983, p. 112(2)-p. 241-7.
Gardner et al., "In Vitro Activity of Sorghum-Selective Fluorophenyl Urea Herbicides", Pesticide Biochemistry and Physiology, 24(3):285-297, (1985).
Gatzemeier et al., "Phase III Comparative Study of High-Dose Cisplatin Versus a Combination of Paclitaxel and Cisplatin in Patients With Advanced Non-Small-Cell Lung Cancer", Journal of Clinical Oncology 18(19):3390-3399 (2000).
Genitourinary Cancers, Prostate Cancer Genitourinary, http://www.merkmanuals.com/professional/print/sec17/ch241/ch241e.html Mar. 16, 2011.
Gerald B. Dermer, "Another anniversary for the war on cancer", Bio/Technology, vol. 12, 1994, p. 320.
Giles, F., "The Vascular Endothelial Growth Factor (VEGF) Signaling Pathway: A Therapeutic Target in Patients with Hematologic Malignancies", The Oncologists 6(supp15):32-39 (2001).
Golkar, et al., "Mastocytosis", Lancet, 349, 1997, p. 1379-p. 1385.
Gould et al., International Journal of Pharmaceutics, Elsevier, BV, NL, vol. 33, No. 1-3, Nov. 1, 1986, p. 201-p. 217, XP025813036.
Guo et al., "Expression of gastric cancer-associated MG7 antigen in gastric cancer, precancerous lesions and *H. pylori*-associated gastric diseases", Word J. Gastroenterol, 8(6):1009-1013 (2002).
Haller, D., "Chemotherapy for Advanced Pancreatic Cancer", Int. J. Radiation Oncology Biol. Phys., 56(4): Supplement, pp. 16-23 (2003).
Hamby et al., "Structure-Activity Relationships for a Novel Series of Pyrido[2,3-d]pyrimidine Tyrosine Kinase Inhibitors", Journal of Medicinal Chemistry., 40, 2296-2303, 1997.
Hamel, et al., "The Road Less Travelled: c-kit and Stem Cell Factor", Journal of Neuro-Oncology, 35, 1997, p. 327-p. 333.

(56) References Cited

OTHER PUBLICATIONS

Hannequin et al., "Novel 4-Anilinoquinazolines with C-7 Basic Side Chains: Design and Structure Activity Relationship of a Series of Potent, Orally Active, VEGF Receptor Tyrosine Kinase Inhibitors", Journal of Medicine Chemistry 45:1300-1312 (2002).
Hattori et al, "Immunohistochemical Detection of K-sam Protein in Stomach Cancer", Clinical Cancer Research, 2:1373-1381 (1996).
Hayek, et al., "An In Vivo Model for Study of the Angiogenic Effects of Basic Fibroblast Growth Factor", Biochemical and Biophysical Research Communications, 147(2), 1987, p. 876-p. 880.
Haymo et al., "Pericytes in experimental MDA-MB231 tumor angiogenesis", Histochemistry and Cell Biology, 117(6):527-534 (2002).
Heinrich et al., "Inhibition of c-kit receptor tyrosine kinase activity by STI 571, a selective tyrosine kinase inhibitor", Hematopoeisis, Blood 96(3):925-932 (2000).
Heinrich et al., "Inhibition of KIT Tyrosine Kinase Activity: A Novel Molecular Approach to the Treatment of KIT-Positive Malignancies", Journal of Oncology 20(6):1692-1703 (2002).
Hibi, et al., "Coexpression of the Stem Cell Factor and the c-kit Genes in Small-Cell Lung Cancer", Oncogene, 6, 1991, p. 2291-p. 2296.
Hines, et al., "Coexpression of the c-kit and Stem Cell Factor Genes in Breast Carcinomas", Cell Growth & Differentiation, 6, 1995, p. 769-p. 779.
Hogaboam, et al."Novel Role of Transmembrane SCF for Mast Cell Activation and Eotaxin Production in Mast Cell-Fibroblast Interactions", The Journal of Immunology, 160, 1998, p. 6166-p. 6171.
Hurwitz et al., "Bevacizumab plus Irinotecan, Fluorouracil, and Leucovorin for Metastatic Colorectal Cancer", The New England Journal of Medicine', 350(23):2335-2342 (2004).
Huston et al., "Protein engineering of antibody binding sites: Recovery of specific activity in an anti-digoxin single-chain Fv analogue produced in *Escherichia coli*", Proc. Natl. Acad. Sci. USA 85:5879-83, 1988.
Ikeda, et al., "Changes in Phenotype and Proliferative Potential of Human Acute Myeloblastic Leukemia Cells in Culture with Stem Cell Factor", Experimental Hematology, 21, 1993, p. 1686-p. 1694.
Ikeda, et al., "Expression and Functional Role of the Proto-Oncogene c-kit in Acute Myeloblastic Leukemia Cells", Blood, 78(11), 1991, p. 2962-p. 2968.
Inai et al, "Inhibition of Vascular Endothelial Growth Factor (VEGF) Signaling in Cancer Causes Loss of Endothelial Fenestrations, Regression of Tumor Vessels, and Appearance of Basement Membrane Ghosts", American J. of Pathol. 165(1): 35-52 (2004).
Inoue et al., "Molecular Target Therapy Targeting Angiogenesis Pathways", The Nishinihon J. Urol., 66:425-432 (2004).
International Search Report issued for related PCT application PCT/JP01/09221, Jan. 15, 2002.
International Search Report issued for related PCT application PCT/JP2004/003087, Jul. 13. 2004.
ISR (PCT/JP2006/315563) dated Sep. 5, 2006.
ISR (PCT/JP2006/315698) dated Oct. 17, 2006.
ISR (PCT/JP2006/322514) dated Jan. 23, 2007.
ISR (PCT/JP2006/323881) dated Jan. 23, 2007.
ISR (PCT/JP2007/060560) dated Sep. 11, 2007.
ISR (PCT/JP2007/063525) dated Sep. 4, 2007.
IPRP (PCT/JP2007/067088) dated Mar. 3, 2009 with English translation.
ISR (PCT/JP2007/067088) dated Nov. 20, 2007 with English translation.
ISR (PCT/JP2008/051024) dated Apr. 1, 2008.
ISR (PCT/JP2008/051697) dated Mar. 4, 2008.
ISR (PCT/JP2008/070321) dated Jan. 20, 2009.
ISR (PCT/JP2009/051244) dated Mar. 24, 2009.
Itoh et al., "Preferential Alternative Splicing in Cancer Generates a K-sam Messenger RNS with Higher Transforming Activity", Cancer Research 54: 3237-3241(2002).
J. Haleblian, Characterization of Habits and Crystalline Modification of Solids and Their Pharmaceutical Applications, "Journal of Pharmaceutical Sciences", 64(8):1269-1288 (1975).

Jakeman, et al., "Developmental Expression of Binding Sites and Messenger Ribonucleic Acid for Vascular Endothelial Growth Factor Suggests a Role for This Protein in Vasculogenesis and Angiogenesis", Endocrinology, 133(2), 1993, p. 848-p. 859.
Japanese Office Action for Application No. 2005-516605, Jun. 1, 2010 (with partial translation).
Japanese Publication of Patent Application No. H11-322596 with English translation.
Japanese Patent Application No. 2006-230816 (English translation).
Jhiang, S., "The RET proto-oncogene in human cancers", Oncogene 19:5590-5597 (2000).
Jimenez et al., "Pheochromocytoma and Medullary Thyroid Carcinoma:A New Genotype-Phenotype Correlation of the RET Protooncogene 891 Germline Mutation", The Journal of Clinical Endocrinology & Metabolism 89(8):4142-4145 (2004).
Johnson et al., "Paclitaxel Plus Carboplatin in Advanced Non-Small-Cell Lung Cancer: A Phase II Trial", Journal of Clinical Oncology 14(7):2054-2060 (1996).
JP Allowance directed at application No. P2005-515330 issued on Apr. 21, 2009, 2 pages.
Jung et al., "Effects of combination anti-vascular endothelial growth factor receptor and anti-epidermal growth factor receptor therapies on the growth of gastric cancer in a nude mouse model", European Journal of Cancer, 38:1133-1140 (2002).
Juurikivi et al., "Inhibition of c-kit tyrosine kinase by imatinib mesylate induces apoptosis in mast cells in rheumatoid synovia: a potential approach to the treatment of arthritis", Ann. Rheum. Dis., 64:1126-1131 (2005).
Kanakura, et al., "Expression, Function and Activation of the Proto-Oncogene c-kit Product in Human Leukemia Cells", Leukemia and Lymphorma, 10, 1993, p. 35-p. 41.
Karl Nocka, et al., "Expression of c-kit gene products in known cellular targets of W mutations in normal and W mutant mice-evidence for an impaired c-kit kinase mutant mice", Genes & Development, Cold Spring Harbor Laboratory Press, 3:816-826, (1989).
Kashuk et al., "Phenotype-genotype correlation in Hirschsprung disease is illuminated by comparative analysis of the RET protein sequence", PNAS 102(25):8949-8954 (2005).
Kay, et al., "Eosinophils and Eosinophil-Associated Cytokines in Allergic Inflammation", Int. Arch. Allergy Immunol 113, 1997, p. 196-p. 199.
Kelly et al., "Randomized Phase III Trial of Paclitaxel Plus Carboplatin Versus Vinorelbine Plus Cisplatin in the Treatment of Patients With Advanced Non-Small-Cell Lung Cancer: A Southwest Oncology Group Trial", Journal of Clinical Oncology 19(13):3210-3218 (2001).
Kim et al., "A Phase II Study of Irinotecan Plus Cisplatin for Patients With Advanced Stage IIIB or IV NSCLC Previously Treated With Nonplatinum-Based Chemotherapy", American Cancer Socieity, pp. 799-805 (2006).
Kim et al., "An Orally Administered Multitarget Tyrosine Kinase Inhibitor, SU11248, Is a Novel Potent Inhibitor of Thyroid Oncogenic RET/Papillary Thyroid Cancer Kinases", The Journal of Clinical Endocrinology & Metabolism 91(10):4070-4075 (2006).
Ko et al., "Stomach Cancer", Cancer supportive care.com, published online Feb. 2003, pp. 1-4.
Kitamura, et al., "Regulation of Development, Survival and Neoplastic Growth of Mast Cells through the c-kit Rector", Int Arch Allergy Immunol., 107, 1995, p. 54-p. 56.
Kolibaba, et al., "Protein Tyrosine Kinases and Cancer", Biochimica et Biophysica Acta, 1333, 1997, p. F217-p. F248.
Kotva, et al., "Substances with Antineoplastic Activity, LIII. N-(δ-(4-Pyrrolo[2,3-d]Pyrimidinylthio) Valeryl]} Amino Acids and Analogous Derivatives of Di-and Triglycine", Collection Czechoslov. Chem. Commun.38, 1973, p. 1438-p. 1444.
KR Office Action directed at application No. 10-2006-7013993 issued on Jul. 31, 2007 (with English translation), 9 pages.
Krystal et al., "Indolinone Tyrosine Kinase Inhibitors Block Kit Activation and Growth of Small Cell Lung Cancer Cells", Cancer Research., 61, 3660-3668, 2001.
Kleespies et al., Tyrosine kinase inhibitors and gemcitabine: New treatment options in pancreatic cancer?, Drug Resistance Updates 9:1-19 (2006).

(56) References Cited

OTHER PUBLICATIONS

Lasota, et al., "Mutations in Exons 9 and 13 of KIT Gene Are Rare Events in Gastrointestinal Stromal Tumors", American Journal of Pathology, 157(4), 2000, p. 1091-p. 1095.

Leukemias, Hematology and Oncology, http://www.merkmanuals.com/professional/print/sec11/ch142/ch142a.html Mar. 16, 2011.

Lesueur et al., "Polymorphisms in RET and Its Coreceptors and Ligands as Genetic Modifiers of Multiple Endocrine Neoplasia Type 2A", Cancer Research 66(2):1177-1180 (2006).

Lev et al., "A Specific Combination of Substrates is Involved in Signal Transduction by the Kit-Encoded Rector", The EMBO Journal,10(3), 1991, p. 647-p. 654.

Li et al., "Abrogation of c-kit/Steel factor-dendent tumorigenesis by kinase defective mutants of the c-kit rector: c-kit kinase defective mutants as candidate tools for cancer gene therapy, Cancer Research vol. 56", Oct. 1, 1996, p. 4343-p. 4346, XP002522473.

Lin et al., "The Vascular Endothelias Growth Factor Receptor Tyrosine Kinase Inhibitor K787/ZK222584 Inhibits Growth and Migration of Mutiple Myeloma Cells in the Bone Marrow Microenvironment", Cancer Research, 62:5019-5026 (2002).

Logie et al., "Activating mutations of the tyrosine kinase receptor FGFR3 are associated with benign skin tumors in mice and humans", Human Molecular Genetics, 14(9):1153-1160 (2005).

Longley, et al., "Altered Metabolism of Mast-Cell Growth Factor (c-kit Ligand) in Cutaneous Mastocytosis", The New England Journal of Medicine, 328(18), 1993, p. 1302-p. 1307.

Longley, et al., "Classes of c-Kit activating mutations: proposed mechanisms of action and implications for disease classification and therapy", Leukemia Res., 25:571-576, (2001).

Longley, et al., "Somatic c-KIT Activating Mutation in Urticaria Pigmentosa and Aggressive Mastocytosis: Establishment of Clonality in a Human Mast Cell Neoplasm", Nature Genetics, 12, 1996, p. 312-p. 314.

Lukacs, et al., "Stem Cell Factor (c-kit Ligand) Influences Eosinophil Recruitment and Histamine Levels in Allergic Airway Inflammation", The Journal of Immunology, 156, 1996, p. 3945-p. 3951.

Matsui et al., "E7080 (ER-203492-00), a Novel VEGF Rector Tyrosine Kinase Inhibitor-I. Characterization as an Angiogenesis Inhibitor.", Abstract # 51, AACR, Toronto, Canada, Apr. 5-9, 2003.

Matsui et al., "E7080, a novel inhibitor that targets multiple kinases, has potent antitumor activities against stem cell factor producing human small cell lung cancer H146, based on angionenesis inhibition", Int. J. Cancer 122:664-671 (2008).

Matsui et al., "E7080, a novel multi-rector Tyrosine Kinase Inhibitor, inhibited in vitro / in vivo VEGF- and SCF-driven angiogenesis SCLC cell line", Matsui et al., Abstract #146, EORTC-NCI-AACR, Geneva, Switzerland, Sep. 28-Oct. 1, 2004.

Matsui et al., "Quantitative analysis of the profile of tumor vessels may be useful as predictive biomarkers for E7080", Abstract #4631, 98th AACR annual meeting, Los Angeles, CA Apr. 14-18, 2007.

Matsui et al., "VEGFRs inhibitor E7080 inhibits lymph node metastasis of human breast carcinoma, by preventing murine lymphatic endothelial cells from lymphangiogenesis.", Abstract # PD12-8, 18th EORTC-NCI-AACR symposium on "Molecular Targets and Cancer Therapeutics", Prague, Czech rublic, Nov. 7-10, 2006.

Matsui et al., "146 E7080, a novel multi-targeted tyrosine kinase inhibitor, exhibits anti-angiogenic activity via inhibition of KIT signaling in a small cell lung cancer xenograft model", European Journal of Cancer, Supplement Pergamon, Oxford, GB XP004639590 abstract.

McCarty et al., "ZD6474, a vascular endothelial growth factor receptor tyrosine kinase inhibitor with additional activity against epidermal growth factor receptor tyrosine kinase, inhibits orthotopic growth and angiogenesis of gastric cancer", Molecular Cancer Therapeutics, 3(9):1041-1048 (2004).

McCulloch et al., "Astragalus-Based Chinese Herbs and Platinum-Based Chemotherapy for Advanced Non-Small-Cell Lung Cancer: Meta-Analysis of Randomized Trials", Journal of Clinical Oncology 24(3):419-430 (2006).

Meltzer, E.O., "The Pharmacological Basis for the Treatment of Perennial Allergic Rhinitis and Non-Allergic Rhinitis with Topical Corticosteroids", Allergy, 52, 1997, p. 33-p. 40.

Mendel et al., "In Vivo Antitumor Activity of SU11248, a Novel Tyrosine Kinase Inhibitor Targeting Vascular Endothelial Growth Factor and Platelet-derived Growth Factor Rectors: Determination of a Pharmacokinetic/Pharmacodynamic Relationship" Clin. Cancer Res., 9: 327-337, (2003).

Metcalf, et al., "Lineage Commitment in the Progeny of Murine Hematopoietic Prrogenitor Cells: Influence of Thrombopoietin and Interleukin 5", Proc. Nat'l Acad. Sci. USA, 95, 1998, p. 6408-p. 6412.

Metcalfe, D., "Classification and Diagnosis of Mastocytosis: Current Status", J. Invest. Dermatol, 96, 1991, p. 2S-p. 4S.

Metcalfe, et al., "Mast Cells", Physiological Reviews, 77(4), 1997, p. 1033-p. 1079.

Micke et al., "Characterization of c-kit expression in small cell lung cancer: prognostic and therapeutic implications", Clinical Cancer Res. 9:188-194(2003).

Miller et al., "Paclitaxel plus Bevacizumab versus Paclitaxel Alone for Metastatic Breast Cancer", The New England Journal of Medicine, 357:2666-76 (2007).

Miyazaki et al., "Synthesis, Structure and Biological Activity Relationship of E7080 and its Derivatives as Novel and Potent Antiangiogenic Protein Tyrosine Kinase Inhibitors Including the VEGF Rectors, FGFR1 Rector and PDGF Rector." Abstract B-15, AIMECS03, Kyoto, Japan, Oct. 14-17, 2003.

Miyazaki et al., Synthesis, Structure and Biological Activity Relationship of . . . PDGF Receptor, AIMECS 03, 5th AFMC International Medicinal Chem. Symposium, Oct. 2003, Kyoto Japan, 1 page.

Mologni et al., "Inhibition of RET tyrosine kinase by SU5416", Journal of Mol. Endo., 37:199-212 (2006).

Morgan et al., "Dynamic Contrast-Enhanced Magnetic Resonance Imaging As a Biomarker for the Pharmacological Response of PTK787/ZK 222584, an Inhibitor of the Vascular Endothelial Growth Factor Receptor Tyrosine Kinases, in Patients With Advanced Colorectal Cancer and Liver Metastases: Results From Two Phase I Studies", Journal of Oncology 21(21):3955-3964 (2003).

Morikawa et al., Angiogenesis and Pericytes, Putative Positive Function of Pericytes in Angiogenesis, Cell, vol. 37, No. 4, pp. 164-168, with English translation, (2005).

Morris et al., "An integrated approach to the selection of optimal salt form for a new drug candidate," International Journal of Pharmaceutics, Elsevier, BV, NL, vol. 105, No. 3, May 9, 1994, p. 209-p. 217, XP023724810.

Myers, et al., "The Praration and SAR of 4-(Anilino), 4-(Phenoxy), and 4-(Thiophenoxy)-Quinazolines: Inhibitors of p56lck and EGF-R Tyrosine Kinase Activity", Bioorgan. & Med. Chem. Letters, 7, 1997, p. 417-p. 420.

Naclerio, et al., "Rhinitis and Inhalant Allergens", JAMA, 278(22), 1997, p. 1842-p. 1848.

Nagata, et al., "Elevated Expression of the Proto-Oncogene c-kit in Patients with Mastocytosis", Leukemia, 12, 1998, p. 175-p. 181.

Nakamura et al., "E7080 (ER-203492-00), a Novel VEGF Rector Tyrosine Kinase Inhibitor-II. Effects on Growth of Human Tumor Xenografts and Life Span of Mice in Colon 38 Orthotopic Transplantation Model." Abstract # 52, AACR, Toronto, Canada, Apr. 5-9, 2003.

Nakamura et al., "KRN633: A Selective inhibitor of vascular endothelial growth factor receptor-2 tyrosine kinase that suppresses tumor angiogenesis and growth", Molecular Cancer Therapeutics., 3:1639-49, 2004.

Naruse, et al., Activity of the Selective Epidermal Growth Factor Receptor-Tyrosine Kinase Inhibitor (EGFR-TKI) IRESSA . . . In Vivo, Int. J. Cancer, 98:310-315, (2002).

Naski et al., "Graded activation of fibroblast growth factor receptor 3 by mutations causing achondroplasia and thanatophoric dysplasia", Nature Genetics 13:233-237 (1996).

Natali, et al., "Breast Cancer is Associated with Loss of the c-kit Oncogene Product", Int. J. Cancer, 52, 1992, p. 713-p. 717.

(56) References Cited

OTHER PUBLICATIONS

Nugiel et al., "Synthesis and Evaluation of Indenopyrazoles as Cyclin-Dependent Kinase Inhibitors. 2. Probing the Indeno Ring Substituent Pattern", Journal of Medical Chemistry, 45(24):5224-5232, (2002).
Ocqueteau et al., "Expression of the CD117 Antigen (C-Kit) on Normal and Myelomatous Plasma cells", British Journal of Haematology, 95:489-493 (1996).
Office Action directed at EP Application No. 04719054.1 issued on Oct. 30, 2009.
Office Action directed at application No. 4025700.8 issued on Apr. 10, 2006, 3 pages.
Ohe et al., "Randomized phase III study of cisplatin plus irinotecan versus carboplatin plus paclitaxel, cisplatin plus gemcitabine, and cisplatin plus vinorelbine for advanced non-small-cell lung cancer: Four-Arm Cooperative Study in Japan", Annals of Oncology 18:317-323 (2007).
Okayama, et al., "Activation of Eosinophils with Cytokines Produced by Lung Mast Cells", Int Arch Allergy Immunol.114:(suppl 1), 1997, p. 75-p. 77.
Okayama, et al., "Human Lung Mast Cells are Enriched in the Capacity to Produce Granulocyte-Macrophage Colony-Stimulating Factor in Response to IgE-Dendent Stimulation", Eur. J. Immunol. 28, 1998, p. 708-p. 715.
Okura et al., "Effects of monoclonal anti-c-kit antibody (ACK2) on melanocytes in newborn mice", J. Invest. Dermatol., 105(3): 322-328 (1995).
Olaso et al., "DDR2 receptor promotes MMP-2-mediated proliferation and invasion by hepatic stellate cells", The Journal of Clinical Investigation, 108(9):1369-1378 (2001).
Ozols et al., "Phase III Trial of Carboplatin and Paclitaxel Compared With Cisplatin and Paclitaxel in Patients With Optimally Resected Stage III Ovarian Cancer: A Gynecologic Oncology Group Study", Journal of Oncology 21(17):3194-3200 (2003).
Pandey et al., "Identification of Orally Active, Potent, and Selective 4-Piperazinylquinazolines as Antagonists of the Platelet-Derived Growth Factor Receptor Tyrosine Kinase Family", Journal of Medicinal Chemistry., 45, 3772-3793, 2002.
Paterson et al., "Preclinical studies of fibroblast growth factor receptor 3 as a therapeutic target in multiple myeloma", Blackwell Publishing Ltd, British Journal of Haematology, 124: 595-603 (2004).
Paz and Zhu, "Development of Angiogenesis Inhibitors to Vascular Endothelial Growth Factor Receptor 2. Current Status and Future Perspectiv", Frontiers in Bioscience 10:1415-1439 (2005).
Plowright et al., "Ectopic expression of fibroblast growth factor receptor 3 promotes myeloma cell proliferation and prevents apoptosis" Neoplasia, Blood, 95(3): 992-998 (2000).
Pritzker, "Cancer Biomarkers: Easier Said Than Done", Clinical Chemistry 48(8):1147-1150 (2002).
PCT/JP2006/322514 International Preliminary Report on Patentability issued on May 7, 2008.
PCT/JP2006/322516 International Search Report issued on Jan. 23, 2007.
PCT/JP2006/322516 International Preliminary Report on Patentability issued on May 7, 2008.
R. Ian Freshney, Alan R. Liss, "Culture of Animal Cells, A Manual of Basic Technique", New York, 1983, p. 4.
Raimondo et al., "Angiogenic factors in multiple myeloma: higher levels in bone marrow than in peripheral blood", Haematologica, 85:800-805 (2000).
Salmon et al., "Anti-Angiogenic Treatment of Gastrointestinal Malignancies", New Drugs, Cancer Investigation 23:712-726 (2005).
Sandler et al., "Phase III Trial of Gemcitabine Plus Cisplatin Versus Cisplatin Alone in Patients With Locally Advanced or Metastatic Non-Small-Cell Lung Cancer", Journal of Clinical Oncology 18(1):122-130 (2000).
Santoro et al., "Drug Insight: small-molecule inhibitors of protein kinases in the treatment of thyroid cancer", Nature Clinical Practice Endocrinology & Metabolism 2(1):42-52 (2006).
Santoro et al., "Molecular Mechanism of RET Activation in Human Cancer", Ann. N.Y. Acad Sci. 963:116-121 (2002).
Santoro et al., "Minireview: RET: Normal and Abnormal Functions", Endocrinology 145(12):5448-5451 (2004).
Scheijen et al. "Tryosine Kinase Oncogenes in Normal Hematopoiesis and Hematological Disease", Oncogene, 21, 2002, p. 3314-p. 3333.
Search Report directed at application No. 4719054.1 issued on Apr. 17, 2009, 4 pages.
Search Report directed at application No. 4818213.3 issued on Jul. 30, 2007, 3 pages.
Search report directed at EP application No. 03791389.4, issued on Jul. 7, 2011, 3 pages.
Sekido, et al., "Preferential Expression of c-kit Protooncogene Transcripts in Small Cell Lung Cancer", Cancer Research, 51, 1991, p. 2416-p. 2418.
Shiang et al., "Mutations in the Transmembrane Domain of FGFR3 Cause the Most Common Genetic Form of Dwarfism, Achondroplasia", Cell 78:335-342 (1994).
Shibata et al., "Rapid Communication Association of Epstein-Barr Virus with Undifferentiated Gastric Carcinomas with Intense Lymphoid Infiltration", American Journal of Pahthology 139(3):469-473 (1991).
Shimizu et al., "Orally active anti-proliferation agents: novel diphenylamine derivatives as FGF-R2 autophosphorylation inhibitors", Bioorganic & Medicinal Chem. Letters 14:875-879 (2004).
Sihto, H., "Kit and Platelet-Derived Growth Factor Receptor Alpha Tyrosine Kinase Gene Mutations and KIT Amplifications in Human Solid Tumors", 23 J. Clin. Oncol. 49-57 (Jan. 1, 2005).
Spacey, et al., "Indolocarbazoles, Potent and Selective Inhibitors of Platelet-Derived Growth Factor Rector Autophosphorylation", Biochemical Pharmacology, 55:261-271, (1998).
Strohmeyer, et al., "Expression of the hst-1 and c-kit Protoonocogenes in Human Testicular Germ Cell Tumors", Cancer Research, 51, 1991, p. 1811-p. 1816.
Taguchi et al., "A novel orally active inhibitor of VEGF rector tyrosine kinases KRN951: Anti-angiogenic and anti-tumor activity against human solid tumors.", Taguchi E et al., Proceedings of the AACR annual meeting., vol. 45, Mar. 2004, p. 595, XP002536608.
Takahashi et al., "A case of inoperable scirrhous gastric cancer that responded remarkably to a combination of TS-1 +paclitaxel and showed complete loss of ascites", JP Journal of Cancer and Chemotherapy, 31(7):1093-1095 (2004).
Takano et al., "Thermal recording materials with improved background stability", Database CA(Online) Chemical Abstracts Service, Columbus, Ohio, US, Feb. 29, 1996, XP002443195.
Takeda et al., "AZD2171 shows potent anti-tumor activity against gastric cancer expressing variant K-SAM/FGFR2", Proceeding of the American Association for Cancer Research, 47:890 (2006) #3785.
Tan et al., "Randomized study of vinorelbine-gemcitabine versus vinorelbine-carboplatin in patients with advanced non-small cell lung cancer", Lung Cancer, 49:233-240 (2005).
Taniguchi, et al., "Effect of c-kit Mutation on Prognosis of Gastrointestinal Stromal Tumors", Cancer Research, 59, 1999, p. 4297-p. 4300.
Thomas et al., "The Eosinophil and its Role in Asthma", Gen. Pharmac. 27(4), 1996, p. 593-p. 597.
Tian, et al., "Activating c-kit Gene Mutations in Human Germ Cell Tumors", American Journal of Pathology, 154(6), 1999, p. 1643-p. 1647.
Thyroid Cancers, Endocrine and Metabolic Disorders, http://www.merkmanuals.com/professional/print/sec12/ch152/ch152j.html Mar. 16, 2011.
Tonary, et al., "Lack of Expression of c-KIT in Ovarian Cancers is Associated with Poor Prognosis", Int. J. Cancer (Pred. Oncol) 89, 2000, p. 242-p. 250.
Tong et al., "Vascular Normalization by Vascular Endothelial Growth Factor Receptor 2 Blockade Induces a Pressure Gradient Across the Vasculature and Improves Drug Penetration in Tumors", Cancer Research 64:3731-3736 (2004).
Traxler et al., "AEE788: A Dual Family Epidermal Growth Factor Receptor/ErbB2 and Vascular Endothelial Growth Factor Receptor

(56) References Cited

OTHER PUBLICATIONS

Tyrosine Kinase Inhibitor with Antitumor and Antiangiogenic Activity", Cancer Research 64:4931-4941 (2004).
Trisha Gura, "Cancer Models Systems for Identifying new drugs are often faulty", Science, vol. 278, Nov. 7, 1997, p. 1041-p. 1042.
Trudel et al., "Inhibition of fibroblast growth factor receptor 3 induces differentiation and apoptosis in t(4;14) myeloma", Neoplasia, Blood, 103(9): 3521-3528 (2004).
Trudel et al., "CHIR-258, a novel, multitargeted tyrosine kinase inhibitor for the potential treatment of t(4;14) multiple myeloma", Neoplasia, Blood 105(7):2941-2948 (2005).
Ueda et al., "Deletion of the Carboxyl-Terminal Exons of K-sam/FGFR2 by Short omologymediated Recombination, Generating Preferential Expression of Specific Messenger RNAs", Cancer Research, 59:6080-6086 (1999).
US Office Action directed at U.S. Appl. No. 10/577,531 issued on Sep. 23, 2008, 17 pages.
US Office Action directed at U.S. Appl. No. 10/797,903 issued on Aug. 20, 2009, 12 pages.
US Office Action directed at U.S. Appl. No. 10/797,903 issued on Dec. 11, 2007.
US Office Action directed at U.S. Appl. No. 11/347,749 issued on Feb. 9, 2009, 6 pages.
US Office Action directed at U.S. Appl. No. 11/997,543 issued May 19, 2011.
US Office Action directed at U.S. Appl. No. 11/997,719 issued on Sep. 3, 2010.
US Office Action directed at U.S. Appl. No. 12/092,539 issued on Jan. 7, 2011.
US Office Action directed at U.S. Appl. No. 12/094,492 issued on Mar. 24, 2011.
US Office Action directed at U.S. Appl. No. 12/301,353 issued on Jan. 24, 2011.
US Office Action directed at U.S. Appl. No. 12/864,817 issued on May 19, 2011.
US Office Action directed at U.S. Appl. No. 12/439,339 issued Nov. 14, 2011.
US Office Action directed a U.S. Appl. No. 12/523,495 issued on Sep. 27, 2011.
Office Action for U.S. Appl. No. 12/092,539 issued on Oct. 29, 2010.
Final Office Action for U.S. Appl. No. 12/092,539 issued on May 9, 2011.
Advisory Action for U.S. Appl. No. 12/092,539 issued on Jun. 28, 2011.
Van Dijk et al. "Induction of Tumor-Cell Lysis by B-Specific Monoclonal Antibodies Recognizing Renal-Cell Carcinoma and CD3 Antigen", Int. J. Cancer 43: 344-9, 1989.
Van Oers et al., "A Simple and Fast Method for the Simultaneous Detection of Nine Fibroblast Growth Factor Receptor 3Mutations in Bladder Cancer and Voided Urine", Clin Cancer Res 11(21):7743-7748 (2005).
Vippagunta et al., "Crystalline solids", Advanced Drug Delivery Reviews 48:3-26 (2001).
Vogel et al., "Sensing extracellular matrix: An update on discoidin domain receptor function", Cellular Signalling 18:1108-1116 (2006).
Wakeling, et al., ZD1839 (Iressa): An Orally Active Inhibitor of Epidermal Growth Factor Signalling with Potential for Cancer Therapy, Cancer Res.,62:5749-5754 ( 2002).
Wakui, "Chemotherapy of scirrhous gastric cancer", JP Journal of Cancer and Chemotherapy, 21(14): 2398-2406 (1994) with English translation.
Wang and Schwabacher, "A Convenient Set of Bidentate Pyridine Ligands for Combinatorial Synthesis", Tetrahedron Lett.40, 1999, p. 4779-p. 4782.
Wang et al., "Phase II study of gemcitabine and carboplatin in patients with advanced non-small-cell lung cancer", Cancer Chemother Pharmacol, 60:601-607 (2007).

Wang, et al., "The Expression of the Proto-Oncogene C-Kit in the Blast Cells of Acute Myeloblastic Leukemia", Leukemia, 3(10), 1989, p. 699-p. 702.
Wedge et al., "AZD2171: A Highly Potent, Orally Bioavailable, Vascular Endothelial Growth Factor Rector-2 Tyrosine Kinase Inhibitor for the Treatment of Cancer", Cancer Res., vol. 65(10), p. 4389-4400, 2005.
Werner et al., "Gastric adenocarcinoma: pathormorphology and molecular pathology", J. Cancer Res. Clin. Oncol. 127:207-216 (2001).
Willett et al., "Direct evidence that the VEGF-specific antibody bevacizumab has antivascular effects in human rectal cancer", Nature Medicine 10(2):145-147 (2004).
Wisniewski et al.,"Characterization of Potent Inhibitors of the Bcr-Abl and the c-Kit Receptor Tyrosine Kinases", Cancer Research., 62, 4244-4255, 2002.
WO IPRP directed at application No. PCT/JP2004/003087 issued on Feb. 23, 2006.
WO IPRP directed at application No. PCT/JP2006/312487 issued on Jan. 10, 2008.
Wood et al., "PTK787/ZK 222584, a Novel and Potent Inhibitor of Vascular Endothelial Growth Factor Receptor Tyrosine Kinases, Impairs Vascular Endothelial Growth Factor-Induced Responses and Tumor Growth after Oral Administration", Cancer Research., 60, 2178-2189, 2000.
Wozniak et al., "Randomized Trial Comparing Cisplatin With Cisplathn Plus Vinorelbine in the Treatment of Advanced Non-Small Cell Lung. Cancer: A Southwest Oncology Group Study", Journal of Clinical Oncology 16(7):2459-2465 (1998).
Yamada et al., "New Technique for Staining", Monthly Medical Technology, Supplementary Volume, Apr. 1999.
Yamamoto et al., "A Novel VEGF Receptor Tyrosine Kinase Inhibitor-III. Significant prolongation of life span in mice transplanted with human ovarian carcinoma based on inhibition of VEGF signaling", Abstract # 50, AACR, Toronto, Canada, Apr. 5-9, 2003.
Yamamoto et al., "E7080 a novel multitargeted tyrosine kinase inhibitor, has direct anti-tumor activity via inhibition of KIT signaling in small cell lung cancer", Yamamoto et al., Abstract #4636, AACR, Orlando, FL, Mar. 27-31, 2004.
Yamamoto et al., "E7080, an oral multi-targeted tyrosine kinase inhibitor, has direct anti-tumor efficacy via inhibition of KIT signaling in gastrointestinal stromal tumor (GIST)" Abstract #40358, 97th annual meeting AACR, Washington, DC., Apr. 1-5, 2006.
Yanagihara et al., "Development and biological analysis of peritoneal metastasis mouse models for human scirrhous stomach cancer", Cancer Sci, 96(6):323-332 (2005).
Yigitbasi et al., "Tumor Cell and Endothelial Cell Therapy of Oral Cancer by Dual Tyrosine Kinase Receptor Blockade", Cancer Research, 64, 7977-7984, 2004.
Yu, Lian, "Amorphous pharmaceutical solids: preparation, characterization and stabilization", Adv. Drug Delivery Reviews, Elsevier, Amsterdam, NL, 48(1):27-42 (2001).
Zhang et al., "Overexpression of Platelet-Derived Growth Factor Receptor α in Endothelial Cells of Hepatocellular Carcinoma Associated with High Metastatic Potential", Clinical Cancer Research 11:8557-8563 (2005).
Zhu et al., "Fibroblast growth factor receptor 3 inhibition by short hairpin RNAs leads to apoptosis in multiple myeloma", Mol Cancer Ther 4(5):787-798 (2005).
Zhu et al., Molecular Targets for Therapy (MTT), "Inhibition of human leukemia in an animal . . . activity", Leukemia 17:604-611 (2003).
Zieger et al., "Role of Activating Fibroblast Growth Factor Receptor 3 Mutations in the Development of Bladder Tumors", Clin Cancer Res 11(21):7709-7719 (2005).
Zhou et al., "Correlation Research on VEGF Testing in Primary Gastric Cancer and Clinical Pathology Factor", Journal of Practical Oncology, 20(2):103-105 (2006) with English translation.
Sun et al., "Synthesis and Biological Evaluations of 3-Substituted Indolin-2-ones: A novel class of Tyrosine kinase inhibitors that exhibit selectivity toward particular receptor tyrosine kinases", Journal of Medicinal Chemistry., 41:2588-2603 (1998).

(56) References Cited

OTHER PUBLICATIONS

Sun et al., "Design, synthesis, and evaluations of substituted 3-[(3-or 4-carboxyethylpyrrol-2-yl)methylidenyl]indolin-2-ones as inhibitors of VEGF, FGF, and PDGF receptor tyrosine kinases", Journal of Medicinal Chemistry., 42:5120-5130 (1999).
Sun et al., "Discovery of 5-[5-Fluoro-2-oxo-1,2-dihydroindol-(3Z)-ylidenemethyl]-2,4-dimethyl-1H-pyrrole-3carboxylic acid . . . Tyrosine Kinase", Journal of Medicinal Chemistry., 46:1116-1119 (2003).
Bold et al., "New anilinophthalazines as potent and orally well absorbed inhibitors of the VEGF receptor tyrosine kinases useful as antagonists of tumor-driven angiogenesis", Journal of Medicinal Chemistry., 43:2310-2323 (2000).
Wilhelm et al., "BAY 43-9006 Exhibits Broad Spectrum Oral Antitumor Activity and Targets the RAF/MEK/ERK Pathway and Receptor Tyrosine Kinases Involved in Tumor Progression and Angiogenesis", Cancer Research., 64:7099-7109 (2004).
Bankston et al., "A Scaleable synthesis of BAY 43-9006: A Potent Raf Kinase Inhibitor for the Treatment of Cancer", Organic Process Res Dev., 6:777-81 (2002).
Response to the European Search Report for Euroepan Application No. 06782407 filed on Nov. 8, 2010.
Office Action issued for European Search Report for European Application No. 06782407 on Sep. 29, 2011.
Response to the Office Action for European Application No. 06782407 filed on Jan. 23, 2012.
Office Action issued for Japanese Application No. 2007-529565 issued on Dec. 13, 2011 with English translation.
Response to the Office Action issued for Japanese Application No. 2007-529565 filed on Feb. 3, 2012 with English full translation.
Office Action directed at Israel Application No. 207089 issued on Nov. 13, 2011 (with English translation).
Written Opinion of the International Searching Authority directed at PCT/JP2009/051244 issued on Mar. 24, 2009 (with English translation).
International Preliminary Report directed at PCT/JP2009/051244 issued on Aug. 31, 2010 (with English translation).
Final Office Action for U.S. Appl. No. 12/523,495 dated Dec. 27, 2011.
Final Office Action for U.S. Appl. No. 11/997,719 issued on Apr. 6, 2011.
Office Action for U.S. Appl. No. 13/205,328 dated Jan. 12, 2012.
Final Office Action for U.S. Appl. No. 11/997,543 dated Nov. 9, 2011.
Office Action for U.S. Appl. No. 12/524,754 dated Dec. 19, 2011.
Israel Office Action directed at Appl. No. 205512 issued on Nov. 13, 2011 with English translation.
PCT/JP2008/070321 Written Opinion of the International Searching Authority issued on Jan. 20, 2009 with English translation.
PCT/JP2008/070321 International Preliminary Report on Patentability issued on May 11, 2010 with English translation.
Sanger et al., "DNA sequencing with chain-terminating inhibitors", Proc. Natl. Acad. Sci. USA 74:5463 (1977).
Wakui, "Chemotherapy for Scirrhous Gastric Cancer", Japanese Journal of Cancer and Chemotherapy, 21:(14): 2398-2406 (1994) (English translation only).
Takahashi et al., "A Case of Inoperable Scirrhous Gastric Cancer that Responded Remarkably to a Combination . . . Loss of Ascites", Japanese Journal of Cancer and Chemotherapy, 31(7):1093-1095 (2004) (English translation only).
PCT/JP2008/051697 Written Opinion of the International Searching Authority issued on Mar. 4, 2008.
PCT/JP2008/051697 International Preliminary Report on Patentability issued on Aug. 4, 2009.
CN200880003336.6 Response to Office Action filed on Oct. 8, 2011.
Israel 200090 Office Actions issued on Jun. 22, 2010.
Israel 200090 Response to Office Action filed on Oct. 12, 2010.
Office Action issued for EP application No. 07806561.2 on Dec. 9, 2011.
Office Action issued for U.S. Appl. No. 10/797,903 on Apr. 1, 2010.

Office Action issued for U.S. Appl. No. 10/797,903 on Sep. 1, 2010.
Office Action (Decision to refuse) issued for EP 04807580.8 on Oct. 25, 2011.
Forbes R T et al.,International Journal of Pharmaceutics, Elsevier Science BV, vol. 126, Jun. 1, 1995, p. 199-208.
Ernst Mutschler et al., Arzneimittel-Wirkungen Lehrbuch Der Pharmakologie Und Toxikologie, Wissenschaftliche Verlagsgesellschaft, Stuttgart, Jan. 1, 1999, p. 1-5 with Full English translation.
Rudolf Voigt et al., Pharmazeutische Technologie Fuer Studium Und Beruf,DT. Apotheker-Verl, Stuttgart; DE, Jan. 1, 2000, p. 40-52, XP008143620 with Full English translation.
Lennartsson et al., "The Stem Cell Factor Receptor/c-Kit as a Drug Target in Cancer", Current Cancer Drug Targets, 6:561-571 (2006).
N. Turner and R. Grose, "Fibroblast growth factor signalling: form development to cancer", Nature Reviews, Cancer,10:116-129 (2010).
S. Wells and M. Santoro, "Targeting the RET Pathway in Thyroid Cancer", Clinical Cancer Research, 15:7119-7123 (2009).
Giuseppe Di Lorenzo et al., "Targeted Therapy in the Treatment of Metastatic Renal Cell Cancer", Oncology, 77(Suppl.1):122-131 (2010).
Abby B.-Siegel et al., "Sorafenib: Where Do We Go from Here?" Hepatology, 52:360-369 (2010).
Kanai et al., "Development Status and Future Prospects of Novel Molecular Target Drugs for Hepatocellular Carcinoma", Journal of the Japanese Society of Gastroenterology, 106:1727-1735 (2009).
National Institutes of Health, Food and Drug Administration, National Library of Medicine, http://clinicaltrials.gov/ct2/show/study/NCT01136733, May 26, 2010.
Office Action issued for EP application No. 04818213.3 on Feb. 2, 2012.
Kitteringham et al., "A Simple Method for the Synthesis of Unsymmetrical Ureas", Synthetic Communications, 30(11):1937-1943 (2000).
Notice of Allowance issued for U.S. Appl. No. 12/986,638 on Mar. 22, 2012.
International Preliminary Examination Report and Patentability and Written Opinion for International Application No. PCT/2010/063804 dated Mar. 22, 2012.
Restriction Requirement issued for U.S. Appl. No. 11/997,543 dated Feb. 23, 2011.
Restriction Requirement issued for U.S. Appl. No. 12/092,539 dated Oct. 29, 2010.
Restriction Requirement issued for U.S. Appl. No. 12/301,353 dated Oct. 29, 2010.
Restriction Requirement issued for U.S. Appl. No. 12/439,339 dated Jul. 29, 2011.
Restriction Requirement issued for U.S. Appl. No. 12/524,754 Nov. 3, 2011.
Restriction Requirement issued for U.S. Appl. No. 13/083,338 Apr. 12, 2012.
Nishikawa et al., "Cys611Ser mutation in RET proto-oncogene in a kindred with medullary thryroid carcinoma and Hirschsprung's disease", European Journal of Human Genetics, 11,364-368 (2003).
Machens et al., "Genotype-Phenotype Correlations in Hereditary Medullary Thyroid Carcinoma: Oncological Features and Biochemical Properties", Journal of Clinical Endocrinology and Metabolism, 86(3):1104-1109 (2001).
Carniti et al., "The RetC620R Mutation Affects Renal and Enteric Development in a mouse Model of Hirschprung's Disease", American Journal of Pathology, 168, 1262-1275, (2006).
Asai et al., "Mechanism of Ret Activation by a Mutation of Aspartic Acid 631 Identified in Sporadic Pheochromocytoma", Biochemical and Biophysical Research Communications, 255, 587-590 (1999).
Carlomagno et al., "Point Mutation of the RET Proto-Oncogene in the TT Human Medullary Thyroid Carcinoma cell Line", Biochemical and Biophysical Research Communications, 207,1022-1028 (1995).
Berndt et al., "A New Hot Spot for Mutations in the ret Protooncogene Causing Familial Medually Thyroid Carcinoma and Multiple Endocrine Neoplasia Type 2A", Journal of Clinical Endocrinology and Metabolism, 83, 770-774 (1998).

(56) References Cited

OTHER PUBLICATIONS

Miyauchi et al., "Two Germline Missense Mutations of Codons 804 and 806 of the RET proto-oncogene in the Same 15 Allele in a Patient with Multiple Endocrine Neoplasia Type 2B without Codon 915 Mutation", Japanese Journal of D Cancer Research, 90, 1-5, (1999).
Joao et al., "Somatic trinucleotide change encompassing codons 882 and 883 of the RET proto-oncogene in a patient with sporadic medullary thyroid carcinoma", European Journal of Endocrinology, 142, 573-575, (2000).
Kim et al., "RET Oligonucleotide Microarray for the Detection of RET Mutations in Multiple Endocrine Neoplasia Type 2 Syndromes", Clinical Cancer Research, 8,457-463, (2002).
Salvatore et al., "Molecular profile of hyalinizing trabecular tumours of the thyroid: High prevalence of RET/PTC rearrangements and absence of B-raf and N-raspoint mutations", European Journal of Cancer, 41: 816-821 (2005).
Grieco et al., "PTC is a Novel Rearranged Form of the ret Proto-Oncogene and Is Frequently Detected in Vivo in Human Thyroid Papillary Carcinomas", Cell, 60: 557-563 (1990).
Lam et al., "High prevalence of RET proto-oncogene activation (RET/PTC) in papillary thyroid carcinomas", Eur J Endocrinology, 147: 741-745 (2002).
Klugbauer et al., "Detection of a Novel Type of RET Rearrangement (PTC5) in Thyroid Carcinomas after Chernobyl and Analysis of the Involved RET-fused Gene RFG5", Cancer Research, 58: 198-203 (1998).
Klugbauer and Rabes, "The transcription coactivator HT1 F1 and a related protein are fused to the RET receptor tyrosine kinase in childhood papillary thyroid carcinomas", Oncogene, 18: 4388-4393 (1999).
Salassidis et al., "Translocation t(1 0; 14) (q 11.2; q22.1) Fusing the Kinectin to the RET Gene Creates a Novel Rearranged Form (PTC8) of the RET Proto-Oncogene in Radiation-induced Childhood Papillary Thyroid Carcinoma", Cancer Research, 60: 2786-2789 (2000).
Klugbauer et al., "A Novel Type of RET Rearrangement (PTC8) in Childhood Papillary Thyroid Carcinomas and Characterization of the Involved Gene (RFG8)", Cancer Research, 60: 7028-7032 (2000).
Nakata et al., "Fusion of a Novel Gene, ELKS, to RET Due to Translocation t(1 0; 12) (q11; p13) in a Papillary Thyroid Carcinoma", Genes Chromosomes Cancer, 25: 97-103 (1999).
Corvi et al., "RET/PCM-1: a novel fusion gene in papillary thyroid carcinoma", Oncogene, 19:4236-4242 (2000).
Written Opinion of the International Searching Authority for PCT/JP2007/060560 mailed on Sep. 11, 2007 with English translation.
International Preliminary Report of Patentability issued for PCT/JP2007/060560 on Nov. 18, 2008 with English translation.
Australian Office Action directed at Appl. No. 2007252506 issued on Nov. 7, 2011.
Australian Response to Office Action directed at Appl. No. 2007252506 filed on Jan. 4, 2012.
Australian Office Action directed at Appl. No. 2007252506 issued on Jan. 13, 2012.
Chinese Office Action directed at Appl. No. 200780017371.9 mailed on Oct. 20, 2010 with English translation.
Chinese Response to Office Action directed at Appl. No. 200780017371.9 filed on Feb. 24, 2011 with English translation.
European Response to EESR directed at Appl. No. 07743994.1-2123 filed on Nov. 23, 2010.
Israel Office Action directed at Appl. No. 195282 issued on Jan. 26, 2010 with English translation.
Israel Response (IDS List) to Office Action directed at Appl. No. 195282 filed on May 3, 2010 with English translation.
Israel Appl. No. 195282 IDS List filed on Jul. 1, 2010.
Russian Office Action directed at Appl. No. 2008149948/15(065561) issued on May 24, 2011 with English translation.
Russian Response to Office Action directed at Appl. No. 2008149948/15(065561) filed on Jul. 27, 2011 with English translation.
Russian Decision of Grant directed at Appl. No. 2008149948/15(065561) with English translation.
US Office Action directed at U.S. Appl. No. 12/301,353 issued on Oct. 29, 2010.
US Response to Office Action directed at U.S. Appl. No. 12/301,353 filed on Nov. 23, 2010.
Australian Response to Office Action directed at Appl. No. 2007252506 filed on Mar. 2, 2012.
Response to Office Action directed at Australian Appl. No. 2006309551 filed on Mar. 30, 2012.
US Office Action directed at U.S. Appl. No. 13/083,338 dated Jun. 8, 2012.
US Final Office Action for U.S. Appl. No. 12/439,339 dated Mar. 30, 2012.
Zimmermann et al., "Potent and Selective Inhibitors of the ABL-Kinase:Phenylamino-Pyrimidine (PAP) Derivatives", Bioorganic and Medicinal Chemistry Letters., 7(2):187-192, 1997.
Zimmermann, "Electrical Breakdown, Electropermeabilization and Electrofusion", Rev. Physiol. Biochem. Pharmacol. 105:176-260 (1986).
"Current Protocols in Molecular Biology", John Wiley & Sons Section 11.4-11.13 (1987).
Antibodies: A Laboratory Manual, E. Harlow and D. Lane, ed.. Cold Spring Harbor Laboratory (Cold Spring Harbour, NY, 1988).
First Office Action issued on Mar. 6, 2012 for the corresponding JP application, JP2007-542863, and English translation.
Amendment and Argument filed on Apr. 27, 2012 in response to the JP Office Action for JP2007-542863 and English translation.
Heinrich et al., "Kinase Mutations and Imatinib Response in Patients with Metastatic Gastrointestinal Stromal Tumor", Journal of Clinical Oncology, vol. 21, No. 23:4342-4349 (2003).
Paulus, "Preparation and Biomedical Applications of Bispecific Antibodies", Behring Inst. Mitt. 78:118-132 (1985).
Waterman, M., "Computer Analysis of Nucleic Acid Sequences", Methods in Enzymology, 164:765-793 (1988).
Wilbur, W.J. and Lipman, D.J., "Rapid similarity searches of nucleic acid and protein data banks", Natl. Acad. Sci, U.S.A. 80:726-730 (1983).
Altschul et al., "Basic Local Alignment Search Tool", J. Mol. Biol. 215:403-410 (1990).
Pearson, "Rapid and Sensitive Sequence Comparison with FASTP and FASTA", Methods in Enzymology 183:63-98 (1990).
Jang et al., "Mutations in Fibroblast Growth Factor Receptor 2 and Fibroblast Growth Factor Receptor 3 Genes Associated with Human Gastric and Colorectal Cancers", Cancer Research, 61:3541-3543 (2001).
Japanese Classification of Gastric Carcinoma "Igan-Toriatsukai Kiyaku" (Jun. 1999, 13th ed.) and an English translation.
Voluntary Amendment filed on Feb. 17, 2012 for TH patent appl. No. 1201000221 with English translation.
Office Action dated Apr. 11, 2012 for RU patent appl. No. 2012103471 with English translation.
Office Action dated Apr. 27, 2012 for KR patent appl. No. 10-2007-7001347 with English translation.
Office Action dated May 3, 2012 for IN patent appl. No. 383/CHENP/2008.
Examination Report dated May 9, 2012 for PK patent appl. No. 94/2011.
Office Action dated Jun. 5, 2012 for JP patent appl. No. 2009-123432 with English translation.
Response to the OA filed on May 29, 2012 for RU patent appl. No. 2012103471 with English translation.
Examiner's Report dated Sep. 20, 2005 for AU Patent Application No. 2001295986.
Response filed on Apr. 27, 2006 for AU Patent Application No. 2001295986.
Examiner's Report dated May 4, 2006 for AU Patent Application No. 2001295986.
Response filed on Jul. 26, 2006 for AU Patent Application No. 2001295986.
Notice of Acceptance dated Aug. 3, 2006 for AU Patent Application No. 2001295986.
Voluntary Amendment filed on Aug. 30, 2006 for AU Patent Application No. 2006203099.

(56) References Cited

OTHER PUBLICATIONS

Examiner's Report dated Feb. 21, 2008 for AU Patent Application No. 2006203099.
Voluntary Amendment filed on Feb. 21, 2007 for AU Patent Application No. 2006203099.
Voluntary Amendment filed on Feb. 27, 2007 for AU Patent Application No. 2006236039.
Examiner's Report dated Mar. 26, 2008 for AU Patent Application No. 2006236039.
Response filed on May 8, 2008 for AU Patent Application No. 2006236039.
Notice of Acceptance dated May 13, 2008 for AU Patent Application No. 2006236039.
Office Action dated Dec. 6, 2007 for CA Patent Application No. 2426461.
Response filed on May 16, 2008 for CA Patent Application No. 2426461.
Office Action dated Nov. 20, 2008 for CA Patent Application No. 2426461.
Response filed on Feb. 23, 2009 for CA Patent Application No. 2426461.
Office Action dated May 8, 2009 for CA Patent Application No. 2426461.
Response filed on Aug. 13, 2009 for CA Patent Application No. 2426461.
Office Action dated Feb. 10, 2010 for CA Patent Application No. 2426461.
Response filed on May 20, 2010 for CA Patent Application No. 2426461.
Voluntary Amendment filed on Aug. 19, 2010 for CA Patent Application No. 2426461.
Notice of Allowance dated Oct. 14, 2010 for CA Patent Application No. 2426461.
Amendment after Allowance filed on Jan. 4, 2011 for CA Patent Application No. 2426461.
Office Letter Confirmation of Amendment After Allowance dated Jan. 11, 2011 for CA Patent Application No. 2426461.
Amendment filed on May 28, 2003 for CN Patent Application No. 01819710.8 with English translation.
Office Action dated May 13, 2005 for CN Patent Application No. 01819710.8 with English translation.
Response filed on Sep. 13, 2005 for CN Patent Application No. 01819710.8 with English translation.
Amendment filed on Sep. 13, 2005 for CN Patent Application No. 01819710.8 with English translation.
Office Action dated Feb. 10, 2006 for CN Patent Application No. 01819710.8 with English translation.
Response filed on Apr. 11, 2006 for CN Patent Application No. 01819710.8 with English translation.
Amendment filed on Apr. 11, 2006 for CN Patent Application No. 01819710.8 with English translation.
Office Action dated Aug. 11, 2006 for CN Patent Application No. 01819710.8 with English translation.
Response filed on Oct. 9, 2006 for CN Patent Application No. 01819710.8.
Amendment filed on Oct. 9, 2006 for CN Patent Application No. 01819710.8.
Notice of Allowance dated Dec. 15, 2006 for CN Patent Application No. 01819710.8 with.
Office Action dated Jul. 24, 2009 for CN Patent Application No. 200710007096.4.
Office Action dated Mar. 6, 2009 for CN Patent Application No. 200710007097.9.
Response filed on Jul. 2, 2009 for CN Patent Application No. 200710007097.9.
Amendment filed on Jul. 2, 2009 for CN Patent Application No. 200710007097.9.
Office Action dated Sep. 11, 2009 for CN Patent Application No. 200710007097.9 with.
Response filed on Nov. 19, 2009 for CN Patent Application No. 200710007097.9 with English translation.
Amendment filed on Nov. 19, 2009 for CN Patent Application No. 200710007097.9 with English translation.
Office Action dated Dec. 25, 2009 for CN Patent Application No. 200710007097.9 with English translation.
Response filed on Jan. 26, 2010 for CN Patent Application No. 200710007097.9 with English translation.
Amendment filed on Jan. 26, 2010 for CN Patent Application No. 200710007097.9 with English translation.
Office Action dated Apr. 27, 2010 for CN Patent Application No. 200710007097.9 with English translation.
Response filed on Jun. 22, 2010 for CN Patent Application No. 200710007097.9 with English translation.
Amendment filed on Jun. 22, 2010 for CN Patent Application No. 200710007097.9 with English translation.
Voluntary Amendment filed on Aug. 11, 2010 for CN Patent Application No. 200710007097.9 with English translation.
Notice of Allowance dated Oct. 9, 2010 for CN Patent Application No. 200710007097.9 with English translation.
Partial European Search Report for EP Patent Application No. 01976786.2; Jul. 6, 2004.
Supplementary European Search Report for EP Patent Application No. 01976786.2; Jul. 6, 2004.
Invitation to declare maintenance of the application for EP Patent Application No. 01976786.2; Jul. 12, 2004.
Maintenance of the application for EP Patent Application No. 01976786.2; Sep. 6, 2004.
Amendments received before examination for EP Patent Application No. 01976786.2; Sep. 10, 2004.
Communication from the Examining Division for EP Patent Application No. 01976786.2; Aug. 17, 2005.
Brief communication to applicant for EP Patent Application No. 01976786.2; Sep. 9, 2005.
Communication from the Examining Division for EP Patent Application No. 01976786.2; Sep. 19, 2005.
Reply to communication from the Examining Division for EP Patent Application No. 01976786.2; Jan. 25, 2006.
Communication from the Examining Division for EP Patent Application No. 01976786.2; Mar. 21, 2006.
Reply to communication from the Examining Division for EP Patent Application No. 01976786.2; Jul. 19, 2006.
Communication about intention to grant a European patent for EP Patent Application No. 01976786.2; Sep. 4, 2006.
Decision to grant a European patent for EP Patent Application No. 01976786.2; Feb. 1, 2007.
Communication regarding the expiry of opposition period for EP Patent Application No. 01976786.2; Jan. 4, 2008.
European search report for EP Patent Application No. 04025700.8; Jan. 13, 2005.
Communication from the Examining Division for EP Patent Application No. 04025700.8; Apr. 10, 2006
Reply to communication from the Examining Division for EP Patent Application No. 04025700.8; Sep. 12, 2006.
Communication from the Examining Division for EP Patent Application No. 04025700.8; Oct. 23, 2006.
Reply to communication from the Examining Division for EP Patent Application No. 04025700.8; Jan. 26, 2007.
Reply to communication from the Examining Division for EP Patent Application No. 04025700.8; Feb. 15, 2007.
Communication about intention to grant a European patent for EP Patent Application No. 04025700.8; Oct. 15, 2007.
Request for amendment of the text intended for grant and translation of claims for EP Patent Application No. 04025700.8; Feb. 1, 2008.
Approval of request for amendments for EP Patent Application No. 04025700.8; Mar. 13, 2008.
Decision to grant a European patent for EP Patent Application No. 04025700.8; Jun. 5, 2008.
Communication regarding the expiry of opposition period for EP Patent Application No. 04025700.8; May 7, 2009.
Deficiencies in sequence listing for EP Patent Application No. 06023078.6; Dec. 5, 2006.

(56) References Cited

OTHER PUBLICATIONS

Reply to the invitation to remedy deficiencies for EP Patent Application No. 06023078.6; Jan. 11, 2007.
Request for correction of errors in filed documents for EP Patent Application No. 06023078.6; Feb. 13, 2007.
European Search Report for EP Patent Application No. 06023078.6; Mar. 16, 2007.
Information about decision on request for EP Patent Application No. 06023078.6; Mar. 21, 2007.
Invitation to declare maintenance of the application for EP Patent Application No. 06023078.6; May 2, 2007.
Maintenance of the application for EP Patent Application No. 06023078.6; Jun. 19, 2007.
Communication from Examining Division for EP Patent Application No. 06023078.6; Aug. 2, 2007.
Reply to communication from the Examining Division for EP Patent Application No. 06023078.6; Sep. 11, 2007.
Communication from the Examining Division for EP Patent Application No. 06023078.6; Sep. 26, 2007.
Reply to communication from the Examining Division for EP Patent Application No. 06023078.6; Feb. 4, 2008.
Communication about intention to grant a European patent for EP Patent Application No. 06023078.6; Jul. 18, 2008.
Request for amendment of the text intended for grant and translation of claims for EP Patent Application No. 06023078.6; Nov. 5, 2008.
Decision to grant a European patent for EP Patent Application No. 06023078.6; Dec. 4, 2008.
Communication regarding the expiry of opposition period for EP Patent Application No. 06023078.6; Nov. 4, 2009.
Voluntary Amendment filed on Sep. 10, 2010 for HU Patent Application No. P0302603 with English translation.
Office Action dated Oct. 16, 2007 for IL Patent Application No. 155447 with English translation.
Response filed on Dec. 4, 2007 for IL Patent Application No. 155447 with English translation.
Notice of Allowance dated Dec. 26, 2007 for IL Patent Application No. 155447 with English translation.
Notice Prior to Examination dated Jun. 29, 2008 for IL Patent Application No. 189677 with English translation.
Response to Notice Prior to Examination filed on Jan. 11, 2009 for IL Patent Application No. 189677 with English translation.
Office Action dated Feb. 18, 2009 for IL Patent Application No. 189677 with English translation.
Response filed on May 13, 2009 for IL Patent Application No. 189677 with English translation.
Notice of Allowance dated Mar. 14, 2010 for IL Patent Application No. 189677 with English translation.
Amendment filed on Mar. 7, 2005 for JP Patent Application No. 2002-536056, with English translation.
Office Action dated Apr. 11, 2005 for JP Patent Application No. 2002-536056 with English translation.
Argument filed on Apr. 19, 2005 for JP Patent Application No. 2002-536056 with English translation.
Amendment filed on Apr. 19, 2005 for JP Patent Application No. 2002-536056 with English translation.
"Notice of Allowance dated Aug. 2, 2005 for JP Patent Application No. 2002-536056" with English translation.
Office Action dated Jan. 27, 2009 for JP Patent Application No. 2005-124034 with English translation.
Japanese Patent Application Laid-Open No. H11-158149 with English translation.
"Argument filed on Mar. 23, 2009 for JP Patent Application No. 2005-124034" with English translation.
"Amendment filed on Mar. 23, 2009 for JP Patent Application No. 2005-124034" with English translation.
"Office Action dated Apr. 28, 2009 for JP Patent Application No. 2005-124034" with English translation.
"Argument filed on May 21, 2009 for JP Patent Application No. 2005-124034" with English translation.
"Amendment filed on May 21, 2009 for JP Patent Application No. 2005-124034" with English translation.
"Notice of Allowance dated Jul. 21, 2009 for JP Patent Application No. 2005-124034" with English translation.
"Written Amendment filed on Jun. 16, 2009 for JP Patent Application No. 2009-123432" with English translation.
"Written Statement filed on Jun. 16, 2009 for JP Patent Application No. 2009-123432" with English translation.
"Preliminary Amendment filed on May 23, 2003 for KR Patent Application No. 10-2003-7005506" with English translation.
"Office Action dated Jul. 27, 2005 for KR Patent Application No. 10-2003-7005506" with English translation.
"Argument Brief filed on Oct. 25, 2005 for KR Patent Application No. 10-2003-7005506" with English translation.
"Amendment filed on Oct. 25, 2005 for KR Patent Application No. 10-2003-7005506" with English translation.
"Office Action dated Jan. 5, 2006 for KR Patent Application No. 10-2003-7005506" with English translation.
"Argument Brief filed on Mar. 6, 2006 for KR Patent Application No. 10-2003-7005506" with English translation.
"Amendment filed on Mar. 6, 2006 for KR Patent Application No. 10-2003-7005506" with English translation.
"Notice of decision for patent dated Jun. 12, 2006 for KR Patent Application No. 10-2003-7005506" with English translation.
"Office Action dated Dec. 8, 2005 for KR Patent Application No. 10-2005-7020292" with English translation.
"Argument Brief filed on Mar. 8, 2006 for KR Patent Application No. 10-2005-7020292" with English translation.
"Amendment filed on Mar. 8, 2006 for KR Patent Application No. 10-2005-7020292" with English translation.
"Notice of decision for patent dated Apr. 17, 2006 for KR Patent Application No. 10-2005-7020292" with English translation.
"Office Action dated Oct. 4, 2005 for MX Patent Application No. PA/a/2003/003362" with English translation.
"Response filed on Dec. 15, 2005 for MX Patent Application No. PA/a/2003/003362" with English translation.
"Office Action dated Jun. 7, 2006 for MX Patent Application No. PA/a/2003/003362" with English translation.
"Response filed on Aug. 21, 2006 for MX Patent Application No. PA/a/2003/003362" with English translation.
"Notice of Allowance dated Oct. 18, 2006 for MX Patent Application No. PA/a/2003/003362" with English translation.
"Office Action dated Nov. 26, 2007 for MX Patent Application No. PA/a/2005/013764" with English translation.
"Office Action dated Mar. 7, 2007 for NO Patent Application No. 20031731" with English translation.
"Response filed on Sep. 10, 2007 for NO Patent Application No. 20031731" with English translation.
"Office Action dated Oct. 4, 2007 for NO Patent Application No. 20031731" with English translation.
"Response filed on May 7, 2008 for NO Patent Application No. 20031731" with English translation.
"Office Action dated May 16, 2008 for NO Patent Application No. 20031731" with English translation.
"Response filed on Aug. 18, 2008 for NO Patent Application No. 20031731" with English translation.
"Office Action dated Sep. 5, 2008 for NO Patent Application No. 20031731" with English translation.
"Response filed on Oct. 13, 2008 for NO Patent Application No. 20031731" with English translation.
"Notice of Allowance dated Oct. 31, 2008 for NO Patent Application No. 20031731" with English translation.
"Examination Report dated Oct. 13, 2003 for NZ Patent Application No. 525324".
"Response filed on Aug. 26, 2004 for NZ Patent Application No. 525324".
"Examination Report dated Sep. 2, 2004 for NZ Patent Application No. 525324".
"Response filed on Jan. 21, 2005 for NZ Patent Application No. 525324".
"Examination Report dated Feb. 18, 2005 for NZ Patent Application No. 525324".

(56) References Cited

OTHER PUBLICATIONS

"Notice of Acceptance of Complete Specification dated Mar. 4, 2005 for NZ Patent Application No. 525324".
"Formality Requirement dated Jun. 18, 2003 for PH Patent Application No. 1-2003-500266".
"Response filed on Aug. 5, 2003 for PH Patent Application No. 1-2003-500266".
"Office Action dated Aug. 8, 2003 for PH Patent Application No. 1-2003-500266".
"Response filed on Sep. 8, 2003 for PH Patent Application No. 1-2003-500266".
"Response filed on Sep. 15, 2003 for PH Patent Application No. 1-2003-500266".
"Office Action dated Jul. 21, 2006 for PH Patent Application No. 1-2003-500266".
"Response filed on Aug. 14, 2006 for PH Patent Application No. 1-2003-500266".
"Office Action dated Mar. 21, 2007 for PH Patent Application No. 1-2003-500266".
"Response filed on Apr. 17, 2007 for PH Patent Application No. 1-2003-500266".
"Office Action dated Jun. 27, 2007 for PH Patent Application No. 1-2003-500266".
"Response filed on Jul. 31, 2007 for PH Patent Application No. 1-2003-500266".
"Office Action dated Sep. 7, 2007 for PH Patent Application No. 1-2003-500266".
"Response filed on Oct. 15, 2007 for PH Patent Application No. 1-2003-500266".
"Notice of Allowability dated Nov. 28, 2007 for PH Patent Application No. 1-2003-500266".
"Response to the Notice of Allowability filed on Dec. 13, 2007 for PH Patent Application No. 1-2003-500266".
"Notification dated Apr. 25, 2008 for PH Patent Application No. 1-2003-500266".
"Response filed on Apr. 30, 2008 for PH Patent Application No. 1-2003-500266".
"Registered dated Feb. 24, 2009 for PH Patent Application No. 1-2003-500266".
"Office Action dated Jun. 29, 2004 for RU Patent Application No. 2003114740" with English translation.
"Response filed on Nov. 30, 2004 for RU Patent Application No. 2003114740" with English translation.
"Office Action dated Jan. 19, 2005 for RU Patent Application No. 2003114740" with English translation.
"Response filed on Mar. 17, 2005 for RU Patent Application No. 2003114740" with English translation.
"Notice of Allowance dated Apr. 19, 2005 for RU Patent Application No. 2003114740" with English translation.
"Amendment filed on Apr. 17, 2002 for TW Patent Application No. 90125928" with English translation.
"Rejection dated Apr. 26, 2004 for TW Patent Application No. 90125928" with English translation.
"Reexamination filed on Nov. 25, 2004 for TW Patent Application No. 90125928" with English translation.
"Office Action dated Oct. 11, 2007 for TW Patent Application No. 90125928" with English translation.
"Response filed on Dec. 11, 2007 for TW Patent Application No. 90125928" with English translation.
"Notice of Allowance dated Oct. 20, 2008 for TW Patent Application No. 90125928" with English translation.
"Notice of Allowance dated Jun. 3, 2008 for U.S. Appl. No. 11/293,785".
"Notice of Allowance dated Nov. 19, 2008 for U.S. Appl. No. 11/293,785".
"Notice of Allowance dated Feb. 27, 2009 for U.S. Appl. No. 11/293,785".
"Notice of Allowance dated May 18, 2009 for U.S. Appl. No. 11/293,785".
"Preliminary Amendment filed on Apr. 18, 2003 for U.S. Appl. No. 10/420,466".
"Office Action dated Apr. 13, 2005 for U.S. Appl. No. 10/420,466".
"Response filed on Jul. 1, 2005 for U.S. Appl. No. 10/420,466".
"Notice of Allowance dated Sep. 12, 2005 for U.S. Appl. No. 10/420,466".
"Notice of Allowance dated Jun. 13, 2006 for U.S. Appl. No. 10/420,466".
"Notice of Allowance dated Mar. 16, 2007 for U.S. Appl. No. 10/420,466".
Preliminary Amendment filed on Dec. 2, 2005 for U.S. Appl. No. 11/293,785.
"Preliminary Amendment filed on Feb. 3, 2006 for U.S. Appl. No. 11/293,785".
"Office Action dated Sep. 4, 2007 for U.S. Appl. No. 11/293,785".
"Response filed on Feb. 26, 2008 for U.S. Appl. No. 11/293,785".
"Notification of Non-Compliant Amendment filed on Jan. 13, 2005 for U.S. Appl. No. 10/420,466".
"Office Communication concerning dated Sep. 13, 2004 for U.S. Appl. No. 10/420,466".
"Response filed on Oct. 8, 2004 for U.S. Appl. No. 10/420,466".
"Preliminary Amendment filed on Oct. 27, 2003 for U.S. Appl. No. 10/420,517".
ISR dated Jan. 15, 2002 for International Patent Application No. PCT/JP01/09221.
IPRP dated Jan. 8, 2003 for International Patent Application No. PCT/JP01/09221.
Amendment filed on Aug. 4, 2004 for ZA Patent Application No. 2003/3567.
Notice of Acceptance dated Aug. 10, 2004 for ZA Patent Application No. 2003/3567.
Amendment filed on Aug. 17, 2004 for ZA Patent Application No. 2003/3567.
Amended description filed after receipt of search report for EP Patent Application No. 10809938.3; Dec. 8, 2011.
"Amendment filed on Dec. 12, 2011 for JO Patent Application No. 55/2011" with English translation.
"Written Amendment filed on Sep. 21, 2011 for JP Patent Application No. 2011-527665" with English translation.
"Written Statement filed on Sep. 21, 2011 for JP Patent Application No. 2011-527665" with English translation.
Amendment filed on Oct. 28, 2011 for LB Patent Application No. 9292.
Amendment filed on Feb. 9, 2011 for TW Patent Application No. 100104281.
"Amendment filed on Dec. 15, 2011 for VN Patent Application No. Jan. 2011-03484" with English translation.
"ISR dated Sep. 14, 2010 for International Patent Application No. PCT/JP2010/063804".
"IPRP dated Mar. 13, 2012 for International Patent Application No. PCT/JP2010/063804".
Amendment filed on Dec. 22, 2011 for ZA Patent Application No. 2011/08697.
"Voluntary Amendment filed on Feb. 9, 2010 for AU Patent Application No. 2005283422".
"Notice of Allowance dated Apr. 29, 2010 for AU Patent Application No. 2005283422".
"Voluntary Amendment filed on Jul. 6, 2010 for AU Patent Application No. 2005283422".
"Office Action dated Jul. 15, 2011 for CA Patent Application No. 2579810".
"Response filed on Sep. 21, 2011 for CA Patent Application No. 2579810".
"Notice of Allowance dated Oct. 17, 2011 for CA Patent Application No. 2579810".
"Office Action dated Jun. 26, 2009 for CN Patent Application No. 200580026468.7" with English translation.
"Response filed on Sep. 23, 2009 for CN Patent Application No. 200580026468.7" with English translation.
"Amendment filed on Sep. 23, 2009 for CN Patent Application No. 200580026468.7" with English translation.
"Office Action dated Nov. 20, 2009 for CN Patent Application No. 200580026468.7" with English translation.

(56) References Cited

OTHER PUBLICATIONS

"Response filed on Jan. 11, 2010 for CN Patent Application No. 200580026468.7" with English translation.
"Amendment filed on Jan. 11, 2010 for CN Patent Application No. 200580026468.7" with English translation.
"Notice of Allowance dated Feb. 5, 2010 for CN Patent Application No. 200580026468.7" with English translation.
Communication regarding the expiry of opposition period for EP Patent Application No. 05783232.1; Feb. 19, 2010.
"Decision to grant a European patent for EP Patent Application No. 05783232.1; Mar. 19, 2009".
"Communication about intention to grant a European patent for EP Patent Application No. 05783232.1; Nov. 20, 2008".
"Reply to official communication for EP Patent Application No. 05783232.1; Apr. 30, 2008".
"Communication from the Examining Division for EP Patent Application No. 05783232.1; Feb. 7, 2008".
"Maintainance of the application for EP Patent Application No. 05783232.1; Nov. 9, 2007".
Invitation to declare maintenance of the application for EP Patent Application No. 05783232.1; Sep. 25, 2007.
"European Search Report for EP Patent Application No. 05783232.1; Sep. 7, 2007".
"Notice Prior to Examination dated Mar. 9, 2009 for IL Patent Application No. 181697" with English translation.
"Response to Notice Prior to Examination filed on Apr. 22, 2009 for IL Patent Application No. 181697" with English translation.
"Office Action dated Dec. 20, 2010 for IL Patent Application No. 181697" with English translation.
"Response filed on Jan. 26, 2011 for IL Patent Application No. 181697" with English translation.
"Notice of Allowance dated Nov. 14, 2011 for IL Patent Application No. 181697" with English translation.
"Notice of Allowance dated Sep. 20, 2011 for JP Patent Application No. 2006-535174" with English translation.
Japanese Patent Application Laid-Open No. S63-028427 with English translation.
Japanese Patent Application Laid-Open No. 2003-026576 with English translation.
WO00/071097 with English translation.
"Office Action dated Sep. 28, 2011 for KR Patent Application No. 10-2007-7001347" with English translation.
"Amendment filed on Nov. 24, 2011 for KR Patent Application No. 10-2007-7001347" with English translation.
"Argument Brief filed on Nov. 24, 2011 for KR Patent Application No. 10-2007-7001347" with English translation.
"ISR dated Nov. 15, 2005 for International Patent Application No. PCT/JP2005/016941".
"IPRP dated Mar. 20, 2007 for International Patent Application No. PCT/JP2005/016941".
Office Action for JP2007-542863 dated May 29, 2012 with English translation.
AU2006309551 Response to Office Action filed on Mar. 28, 2012.
CN Office Action issued for CN 200880002425.9 on Mar. 7, 2012 with English translation.
AU Office Action issued for AU 2008211952 on Apr. 3, 2012.
CN Office Action directed at Appl. No. 200780017371.9 mailed on Mar. 7, 2012 with English translation.
IL Office Action issued for IL 195282 on Feb. 5, 2012 with English translation.
CN Office Action issued for CN 200880115011.7 on Feb. 20, 2012 with English translation.
Response to IL OA directed at Appl. No. 205512 filed on Mar. 11, 2012 with English translation.
Response to IL OA directed at Appl. No. 207089 filed on Mar. 11, 2012 with English translation.
AU Office Action issued for AU 2008205847 on Apr. 11, 2012.
Response to the OA issued for U.S. Appl. No. 11/997,543 filed on Mar. 22, 2011.
Response to the OA issued for U.S. Appl. No. 11/997,543 filed on Aug. 19, 2011.
Response to the OA issued for U.S. Appl. No. 11/997,543 filed on Jan. 9, 2012.
Response to the OA issued for U.S. Appl. No. 11/997,719 filed on Dec. 23, 2010.
Response to the Final OA issued for U.S. Appl. No. 11/997,719 filed on Jul. 6, 2011.
U.S. Appl. No. 12/092,539 Response to Office Action filed on Nov. 22, 2010.
U.S. Appl. No. 12/092,539 Response to Office Action filed on Mar. 11, 2011.
U.S. Appl. No. 12/092,539 Response to Final Office Action filed on Jun. 15, 2011.
Response to OA issued for U.S. Appl. No. 13/205,328 filed on Apr. 11, 2012.
Response to Office Action directed at U.S. Appl. No. 12/301,353 filed on Nov. 23, 2010.
Response to the OA for U.S. Appl. No. 12/439,339 filed on Aug. 10, 2011.
Response to the OA for U.S. Appl. No. 12/439,339 filed on Feb. 7, 2012.
Response to the OA for U.S. Appl. No. 12/523,495 filed on Dec. 7, 2011.
Response to the OA for U.S. Appl. No. 12/524,754 filed on Dec. 1, 2011.
Response to the OA for U.S. Appl. No. 12/524,754 filed on Feb. 17, 2012.
Response to the OA for U.S. Appl. No. 12/864,817 filed on Aug. 9, 2011.
Response to the OA of U.S. Appl. No. 12/864,817 filed on Dec. 5, 2011.
Response to the OA for U.S. Appl. No. 12/864,817 filed on Dec. 22, 2011.
Asano et al, "Inhibition of Tumor Growth and Metastasis by an Immunoneutralizing Monoclonal Antibody to Human Vascular Endothelial Growth Factor/Vascular Permeability Factor121", Cancer Research., 55, 5296-5301, 1995.
Hori et al., "Suppression of Solid Tumor Growth by Immunoneutralizing Monoclonal Antibody against Human Basic Fibroblast Growth Factor", Cancer Research., 51, 6180-4, 1991.
Gutheil et al., Targeted Antiangiogenic Therapy for Cancer Using Vitaxin: A Humanized Monoclonal Antibody to the Integrin alphavbeta3 1 Clinical Cancer Research., 6, 3056-61, 2000.
Dias et al., "IL-12 Regulates VEGF and MMPs in a Murine Breast Cancer Model", International J. Cancer., 78, 361-5, 1998.
Liu et al., "Structure of Human Methionine Aminopeptidase-2 Complexed with Fumagillin", Science., 282, 1324-1327, 1998.
Wedge et al., "ZD4190: An Orally Active Inhibitor of Vascular Endothelial Growth Factor Signaling with Broad-Spectrum Antitumor Efficacy", Cancer Research., 60, 970-975, 2000.
Hennequin et al., "Design and Structure-Activity Relationship of a New Class of Potent VEGF Receptor Tyrosine Kinase Inhibitors", Journal of Medicinal Chemistry., 42: 5369-5389, 1999.
Fong et al., "SU5416 Is a Potent and Selective Inhibitor of the Vascular Endothelial Growth Factor Receptor (Flk-1/KDR) That Inhibits Tyrosine Kinase Catalysis, Tumor Vascularization, and Growth of Multiple Tumor Types", Cancer Research., 59, 99-106, 1999.
Laird et al., "SU6668 Is a Potent Antiangiogenic and Antitumor Agent That Induces Regression of Established Tumorsl", Cancer Research., 60, 4152-4160, 2000.
Gingrich et al., "A New Class of Potent Vascular Endothelial Growth Factor Receptor Tyrosine . . . Clinical Candidate CEP-7055", Journal of Medicinal Chemistry., 46: 5375-88, 2003.
Beebe et al., "Pharmacological Characterization of CP-547,632, a Novel Vascular Endothelial Growth Factor Receptor-2 Tyrosine Kinase Inhibitor for Cancer Therapy1", Cancer Research. 63:7301-9, 2003.
Petti et al., "Temporal quantitation of mutant Kit tyrosine kinase signaling attenuated by a novel thiophene kinase inhibitor OSI-930", Molecular Cancer Therapeutics., 4:1186-1197, 2005.

(56) References Cited

OTHER PUBLICATIONS

Guo et al., "In Vitro Pharmacological Characterization of TKI-28, a Broad-Spectrum Tyrosine Kinase Inhibitor with Anti-Tumor and Anti-Angiogenic Effects", Cancer Biol Ther., 4, p. 1125-1132, 2005.
Lee et al., "In vivoTargetModulation and Biological Activity of CHIR-258, aMultitargeted Growth Factor Receptor Kinase Inhibitor, in Colon CancerModels", Clinical Cancer Research., 11, 3633-3641, 2005.
Emanuel et al., "A Vascular Endothelial Growth Factor Receptor-2 Kinase Inhibitor Potentiates the Activity of the Conventional Chemotherapeutic Agents Paclitaxel and Doxorubicin in Tumor Xenograft Models", Molecular Pharmacology., 66, 635-647, 2004.
Ruggeri et al., "CEP-7055: A Novel, Orally Active Pan Inhibitor of Vascular Endothelial Growth Factor Receptor Tyrosine Kinases with Potent Antiangiogenic Activity and Antitumor Efficacy in Preclinical Models1", Cancer Research., 63, 5978-5991, 2003.
Kubo et al., "Novel Potent Orally Active Selective VEGFR-2 Tyrosine Kinase Inhibitors: . . . ureas", Journal of Medicinal Chemistry., 48, 1359-1366, 2005.
Amino et al., "YM-231146, a Novel Orally Sioavailable Inhibitor of Vascular Endothelial Growth Factor Receptor-2, Is Effective against Paclitaxel Resistant Tumors", Biological and Pharmaceutical Bulletin. 28:2096-2101, 2005.
Podar et al., "GW654652, the pan-inhibitor of VEGF receptors, blocks the growth and migration of multiple myeloma cells in the bone marrow microenvironment", Blood.,103, 3474-3479, 2004.
Bainbridge et al., "A peptide encoded by exon 6 of VEGF (EG3306) inhibits VEGF-induced angiogenesis in vitro and ischaemic retinal neovascularisation in vivo", Biochem Biophys Res Commun., 302, 793-799, 2003.
Ueda et al., "VGA1155, a Novel Binding Antagonist of VEGF, Inhibits Angiogenesis In Vitro and In Vivo", Anticancer Research., 24, 3009-3017, 2004.
Wulff et al., "Luteal Angiogenesis: Prevention and Intervention by Treatment with Vascular Endothelial Growth Factor TrapA40", The Journal of Clinical Endocrinology & Metabolism. 86(7), 3377-3386, 2001.
Mohammadi et al., "Crystal structure of an angiogenesis inhibitor bound to the FGF receptor tyrosine kinase domain", EMBO J., 17, 5896-5904, 1998.
Roberts et al., "Antiangiogenic and Antitumor Activity of a Selective PDGFR Tyrosine Kinase Inhibitor, CP-673,451", Cancer Research., 65, 957-966, 2005.
Kubo et al., "A Novel Series of 4-Phenoxyquinolines: Potent and Highly Selective Inhibitors of PDGF Receptor Autophosphorylation", Bioorganic and Medicinal Chemistry Letters., 7, 2935-2940, 1997.
Wood et al., "A Unique Structure for Epidermal Growth Factor Receptor Bound to GW572016 (Lapatinib): Relationships among Protein Conformation, Inhibitor Off-Rate, and Receptor Activity in Tumor Cells", Cancer Research., 64, 6652-6659. 2004.
Nyati et al., "Radiosensitization by Pan ErbB Inhibitor CI-1033 in Vitro and in Vivo", Clinical Cancer Research., 10:691-700, 2004.
El-Abseri et al., "Chemoprevention of UV Light-Induced Skin Tumorigenesis by Inhibition of the Epidermal Growth Factor Receptor", Cancer Research., 64, 3958-3965, 2004.
Tsou et al., "Optimization of 6,7-Disubstituted-4-(arylamino)quinoline-3-carbonitriles as Orally Active, Irreversible Inhibitors of Human Epidermal Growth Factor Receptor-2 Kinase Activity", Journal of Medicinal Chemistry., 48, 1107-1131, 2005.
Experimental Medicine, Supplementary Volume, "A New Handbook of Genetic Engineering", Section 4, Yodosha, 2003(Japanese).
Cell Technology, Supplementary Volume, "Bio-Experiment Illustrated vol. 5, No Fear of Proteins", Visual Laboratory Notebook Series, Section 6, Immunostaining, pp. 127-163, Shujunsha, Co., Ltd., 1997 (Japanese).
Masferrer et al., "COX-2 Inhibitors a New Class of Antiangiogenic Agents", Annals of N.Y. Acad. Science., 889:84-6, 1999.
Bramhall, S., "The Matrix Metalloproteinases and Their Inhibitors in Pancreatic Cancer", International J. Pancreatol., 21, 1-12, 1997.
AACR American Association Cancer Research, 92nd Annual Meeting, 42:583, Mar. 24-28, 2001, New Orleans, LA, USA, 3126.
AACR American Association Cancer Research., 93nd Annual Meeting, 43:1080, Apr. 6-10, 2002, San Francisco, CA, USA, 5347.
AACR American Association Cancer Research., 96th Annual Meeting, 46, (Abstract 2031), Anaheim, Orange County, CA, USA Apr. 2005.
EORTC-NCI-AACR Symp Mol Targets Cancer Ther., 2, (Abstract 172), 2004.
AACR American Association Cancer Research, 96th Annual Meeting, 46:1407, (Abstract 5981), Anaheim, Orange County CA USA Apr. 16-20, 2005.
AACR American Association Cancer Research, 96th Annual Meeting, 46 (Abstract 3033), Anaheim, Orange County CA USA Apr. 16-20, 2005.
"Pharmacokinetics (PK) and tolerability of GW786034, a VEGFR tyrosine kinase inhibitor, after daily oral administration to patients with solid tumors.", Proc. Am. Soc. Clin. Oncology, (Abstract 3054), 2004.
ZK304709 (Proceedings of the American Association for Cancer Research, 46, (Abstract 5842), 2005.
EORTC-NCI-AACR Symp Mol Targets Cancer Ther., (Abstract 134), 2004.
EORTC-NCI-AACR Symp Mol Targets Cancer Ther., 2, (Abstract 151), 2004.
Proceedings of the American Association for Cancer Research, 44, 9, (Abstract 39), 2003.
Proceedings of the American Association for Cancer Research, 44, 9, (Abstract 40), 2003.
Proceedings of the American Association for Cancer Research, 45, 694, (Abstract 3005), 2004.
Proceedings of the American Association for Cancer Research, 44, 1479, (Abstract 6454), 2003.
Proc. Am. Soc. Clin. Oncology, (Abstract 776), 2003.
Am. Assoc. Cancer Research, A3394, 2005.
Am. Assoc. Cancer Research, A3405, 2005.
"Recent Results and Ongoing Trials with Panitumumab (ABX-EGF), a Fully Human Anti-Epidermal Growth Factor Receptor Antibody, in Metastatic Colorectal Cancer", Clinical Colorectal Cancer. 2005; 5(1):21-3.
Kim, T., "Technology evaluation: Matuzumab, Merck KGaA", Curr Opin Mol Ther. 2004; 6(1):96-103.
Am. Assoc. Cancer Research, Abstract 5353, 2005.
David et al., "A Phase I Trial of the Epidermal Growth Factor Receptor (EGFR)-Directed Bispecific Antibody (BsAB) MDX-447 in Patients with Solid Tumors. (Meeting abstract).", ASCO 18: 433, Abstract 1999.
The Pharmacology of Monoclonal Antibody, vol. 113, Chapter 11, Rosenburg and Moore ed., Springer Verlag (1994) pp. 269-315.
LeDoussal et al. "Bispecific-Antibody-Mediated Targeting of Radiolabeled Bivalent Haptens: Theoretical, Experimental and Clinical Results", Int. J. Cancer Suppl. 7: 58-62, 1992.
Millstein and Cuello, "Hybrid hybridomas and their use in immunohistochemistry", Nature 305: 537-9, 1983.
Am. Assoc. Cancer Res. Abstract 3399, 2005.
Proceedings of the American Association for Cancer Research, 45, 594, (Abstract 2571), 2004.
Proceedings of the American Association for Cancer Research, 44, 865, (Abstract 3780), 2003.
Decision of Rejection issued on May 29, 2012 for JP No. 2007-542863 with English translation.
Dvorakova et al., "Exon 5 of the RET proto-oncogene: A newly detected risk exon for familial medullary thyroid carcinoma, a novel germ-line mutation Gly321Arg", Journal of Endocrinological Investigation, 28, 905-909, 2005.
Kinlaw et al., "Multiple endocrine neoplasia 2A due to a unique C6095 RET mutation presents with pheochromocytoma and reduced penetrance of medullary thyroid carcinoma", Clin Endocrinol, 69, 676-682, 2005.
Dourisboure et al, "Penetrance and Clinical Manifestations of Non-Hotspot Germ line RET Mutation, C630R, in a Family with Medullary Thyroid Carcinoma", Thyroid, 15, 668-671, 2005.

(56) References Cited

OTHER PUBLICATIONS

Kruckeberg et al., "Pyrosequencing Technology as a Method for the Diagnosis of Multiple Endocrine Neoplasia Type 2", Clinical Chemistry, 50, 522-529, 2004.
Bartsch et al., "A RET double mutation in the germline of a kindred with FMTC", Exp. Clin Endocrinol Diabetes, 108, 128-132, 2000.
Fugazzola et al., "Molecular and biochemical analysis of RET/PTC4, a novel oncogenic rearrangement between RET and ELE1 genes, in a post-Chernobyl papillary thyroid cancer", Oncogene, 13, 1093-1097, 1996.
Hara et al., "Amplification of c-myc, K-sam, and c-met in Gastric Cancers: Detection by Fluorescence in Situ Hybridization", Laboratory Investigation, 78, 1143-1153, 1998.
Office Action issued for JP Appl. No. 2007-529565 issued on May 8, 2012 with English translation.
Response to EP OA for EP 07806561.2 filed on Apr. 18, 2012.
Response to CN OA for CN200880003336.6 filed on May 3, 2012.
Response to IL OA for IL 195282 filed on May 28, 2012.
Response to AU OA for AU 2008211952 filed on Jun. 28, 2012.
Heinemann, V., et al., "Comparison of the Cellular Pharmacokinetics and Toxicity of . . . 1-beta-d-Arabinofuranosylcytosine", Cancer Research, 48, 4024-4031, 1988.
Hertel LW., et al., "Evaluation of the Antitumor Activity of Gemcitabine (2',2'-Difluoro-2'-deoxycytidine)", Cancer Research, 50, 4417-4422, 1990.
IPRP (PCT/JP2008/051024)dated Jul. 21, 2009, with English translation.
Office Action issued for CN 200880002425.9 on Mar. 2, 2011 with English translation.
Argument and Amendment for CN 200880002425.9 filed on Jul. 18, 2011 with English translation.
Office Action for CN 200880002425.9 issued on Mar. 7, 2012 with English translation.
Office Action for IL 199907 issued on Jun. 17, 2010 with English translation.
Response to Office Action for IL 199907 filed on Oct. 11, 2010 with English translation.
Office Action issued for EP06768437.3 (EPO Form1224) issued on Oct. 28, 2010.
Response to OA for EP10015141 filed on Mar. 5, 2012.
PCT/JP2006/0315563 Written Opinion of the International Searching Authority dated Feb. 5, 2008, with English translation.
PCT/JP2006/315563 International Preliminary Report on Patentability dated Feb. 5, 2008, with English translation.
PCT/JP2006/0315698 Written Opinion of the International Searching Authority, dated Feb. 5, 2008, with English translation.
PCT/JP2006/315698 International Preliminary Report on Patentability with dated Feb. 5, 2008, English translation.
Submission of Documents re Claim 3 and Figure 3 for KR App. Ser. No. 10-2009-7005657, filed on Jul. 13, 2012.
Official Letter for AU2008211952 dated Jul. 10, 2012.
Response to Office Action for U.S. Appl. No. 12/741,682 filed Jul. 30, 2012.
Communication for JP2011-527665 dated Jul. 17, 2012 (with English translation).
Communication for EP07806561.2 dated Jun. 25, 2012.
Communication for EP06782407.8 dated Jun. 20, 2012.
Submission of Documents re UAa201203132, dated May 22, 2012 with English translation.
Office Letter for ZA 2011/08697, dated May 25, 2012.
Response to OA for U.S. Appl. No. 12/439,339 filed Jul. 30, 2012.
Submission of Documents for CO 12-022608 dated Jun. 12, 2012.
Chinese Office Action for CN 200680020317.5 dated Aug. 3, 2012 with English translation.
Official Letter for SG 201108602-2 dated Aug. 8, 2012.
Office Action for U.S. Appl. No. 13/083,338 dated Jun. 8, 2012.
European Search Report for EP 08846814.5 dated Jun. 18, 2012.
Office Action for JP2007-529565 dated Aug. 7, 2012 with English translation.
Noriyuki et al., "Anti-tumor effect of E7080, a novel angiogenesis inhibitor", Database Biosis (online) Biosciences Information Service, Philadelphia, PA, US., Database Accession No. PREV200800475929 (abstract), Aug. 2008, XP002677323.
European Search Report for EP 08704376.6 dated Jun. 14, 2012.
Response to Office Action for U.S. Appl. No. 13/083,338 filed Sep. 6, 2012.
De Lange et al., "Phase II trial of cisplatin and gemcitabine in patients with advanced gastric cancer", Annals of Oncology, Kluwer, Dordrecht, NL, 15(3): 484-488, Mar. 1, 2004, XP002511249.
Office Action for IL 199907 issued on Apr. 22, 2012 with English translation.
Response to Chinese Office Action filed for CN 200880115011.7 dated Jul. 5, 2012, with English translation.
Japanese Office Action for JP2009-123432 dated Sep. 4, 2012, with English translation.
Response to Chinese Office Action for CN 200680020317.5 dated Sep. 11, 2012, with English translation.
Official Letter for CA Patent Application No. 2627598 dated Sep. 19, 2012.
Schlumberger et al., "A Phase 2 Trial of the Multi-Targeted Kinase Inhibitor Lenvatinib(E7080) in Advanced Medullary Thyroid Cancer (MTC)", 2012 ASCO Annual Meeting, Poster Presentation, Jun. 1-5, 2012.
Funahashi et al., "P-2123, Lenvatinib treatment of differentiated thyroid cancer (DTC): Analysis to identify biomarkers associated with response", The 71$^{st}$ Annual Meeting of the Japanese Cancer Association, p. 339, Sep. 19-21, 2012.
Tohyama et al., "P-3111, Preclinical effect of lenvatinib on human thyroid cancer targeting angiogenesis and receptor tyrosine kinase signaling", The 71$^{st}$ Annual Meeting of the Japanese Cancer Association, p. 502, Sep. 19-21, 2012.
Chinese Office Action for CN 200880003336.6 dated Sep. 5, 2012, with English translation.
Chinese Office Action for CN 200880115011.7 dated Sep. 5, 2012, with English translation.
Notice of Allowance for U.S. Appl. No. 12/98,6638, Sep. 25, 2012.
Response to Chinese Office Action filed for CN 200880003336.6 dated Jul. 11, 2012, with English translation.
Office Action for U.S. Appl. No. 13/322,961 dated Sep. 25, 2012.
Notice of Allowance for U.S. Appl. No. 12/524,754 dated Oct. 9, 2012.
Office Action for CN 200780017371.9 dated Sep. 28, 2012 with English translation.
Office Action for JP 2008-516724 dated Oct. 9, 2012 with English translation.
Bernex et al., "Spatial and temporal patterns of c-kit-expressing cells in WlacZ/+ and WlacZ/WlacZ mouse embryos", Development 122:3023-3033 (1996).
Office Action for IL 200090 dated Oct. 15, 2012 with English translation.
Office Action (Notice of Allowance) for EP 06782407.8 dated Nov. 2, 2012.
Office Action (Notice of Allowance) for EP 07806561.2 dated Nov. 2, 2012.
Office Action for JP 2008-532141 dated Nov. 13, 2012 with English translation.
International Preliminary Report on Patentability for PCT/JP2011/064430 dated Jan. 24, 2013.
Response to Office Action for Canadian Patent Application No. 2627598 dated Jan. 25, 2013.
Office Action for Australian Patent Application No. 2009210098 dated Jan. 30, 2013.
Response to Office Action for European Application No. 07743994.1 dated Feb. 8, 2013.
Request to amend specification for Australian Patent Application No. 2008325608 dated Feb. 15, 2013.
Response to Office Action for Chinese Patent Application No. 200780017371.9 dated Nov. 30, 2012.
Response to Office Action for CN Application No. 200980103218.7 dated Feb. 16, 2013.
Response to Office Action for U.S. Appl. No. 13/083,338 filed Apr. 2, 2013.

(56) References Cited

OTHER PUBLICATIONS

Response to Office Action for IL Application No. 205512 dated Mar. 14, 2013.
Communication (Notification on Defects in application) for IL Application No. 207089 dated Jan. 6, 2013.
Office Action from CN Patent Application No. 200880115011.7 dated Feb. 25, 2013.
Communication (Notice of Allowance) for CA Patent Application No. 2627598 dated Mar. 8, 2013.
Notice of Acceptance for NZ Application No. 598291 dated Feb. 15, 2013.
Kawano et al., "Presentation Abstract, Abstract Number; 1619,- Combination of VEGFR inhibitor lenvatinib (E7080) and Met/EphB4 inhibitor golvatinib (E7050) overcomes VEGFR inhibitor— resistant I tumor vascular", Annual Meeting 2013, Walter E. Washington Convention Center, Washington, DC, Apr. 6-10, 2013.
Response to Office Action for IL Patent Application No. 175363 dated Feb. 27, 2013.
Notice of Allowance for AU Application No. 2008325608 dated Feb. 27, 2013.
Notice of Allowance for U.S. Appl. No. 12/741,682 dated Feb. 19, 2013.
Office Action from CN Patent Application No. 200780017371.9 dated Mar. 14, 2013 (with English translation).
Response to Office Action for IN Patent Application No. 1571/CHENP/2007 dated Apr. 10, 2013.
Office Action for U.S. Appl. No. 11/997,719 dated Apr. 8, 2013.
Office Action for CN Patent Application No. 201080030508.6 dated Apr. 9, 2013 (with English translation).
Office Action for CA Application No. 2652442 dated Apr. 16, 2013.
Office Action for IL Patent Application No. 217197 dated Apr. 11, 2013 (with English translation).
Response to Office Action for IL Application No. 207089 dated Apr. 22, 2013 (with English translation).
Preliminary Amendment for U.S. Appl. No. 13/870,507 filed Apr. 26, 2013.
Communication (Notice of Allowance) for EP Application No. 04818213.3 dated May 6, 2013.
"Request to Amend a Complete Specification," submitted for Australian Patent Application No. 2009210098 dated May 9, 2013.
Amendment and RCE for U.S. Appl. No. 12/741,682 dated May 17, 2013.
"Supplementary Observation" submitted for CN Application No. 200980103218.7 dated Mar. 13, 2013 (with English translation ).
Response to Office Action for CN Application No. 200880115011.7 dated Apr. 11, 2013 (with English translation ).
Office Action for EP08846814.5 dated Apr. 16, 2013.
Request for Continued Examination and Information Disclosure Statement for U.S. Appl. No. 12/524,743 filed Apr. 15, 2013.
Office Action for KR 10-2008-7013685 dated May 20, 2013 (with English translation).
Office Action for JP2008-532141 dated May 21, 2013 (with English translation).
Office Action for U.S. Appl. No. 12/439,339 dated May 23, 2013.
"Applicant Interview Summary" submitted for U.S. Appl. No. 12/439,339 (dated May 31, 2013).
Response to Office Action for CN201080030508.6 dated May 27, 2013 (with English translation).
Request for Substantive Examination for UA a201203132 dated Apr. 15, 2013 (with English translation).
Request for Substantive Examination for ID W-00201201031 dated Jun. 3, 2013 with English translation.
Notice of Acceptance (Notice of Allowance) for AU2009210098 dated Jun. 4, 2013.
Notice of Allowance for U.S. Appl. No. 13/083,338 dated Jun. 4, 2013.
Notice of Allowance for CN Patent Application No. 200980103218.7 dated May 27, 2013 (with English translation).
Office Action for IL Application No. 195282 dated Apr. 10, 2013 (with English translation).
Notice of Allowance for U.S. Appl. No. 13/205,328 dated Jun. 10, 2013.
U.S. Appl. No. 13/923,858, filed Jun. 21, 2013.
Koyama et al., "Anti-tumor effect ofE7080, a novel angiogenesis inhibitor", Folia Pharmacol. Jpn. 132, Therapeutic Agents Series (28), Molecular Target Drugs-1-1, pp. 100-104, Apr. 18, 2008.
Haiyi Jiang, "ZD6474: an Agent That Selectively Targets Both VEGFR Tyrosine Kinase and EGFR Tyrosine Kinase", Japanese Journal of Lung Cancer, vol. 46, No. 3, Jun. 20, 2006, pp. 283-288.
Stefan Frings, "New Molecular Targeted Therapeutic Drugs Clinical Results of Bevacizumab in Non-Small Cell Lung Cancer (NSCLC)", Japanese Journal of Lung Cancer, vol. 46, No. 3, Jun. 20, 2006, pp. 277-281.
Lumi Chikahisa et al., "TSU-68 JDR/flk-inhibitor, can modulate the anti-tumor activity of paclitaxel by the induction of endothelial cell and tumor cell apoptosis", 61st Annual Meeting of Japanese Cancer Association, 2002, vol. 61, No. 1374, 2002, p. 443.
Office Action for JP2009-551518 dated Jun. 18, 2013 with English translation.
The Argument and the Amendment for JP Patent Application No. 2008-532141 filed on Nov. 29, 2012 (with English translation).
The Argument and the Amendment for JP Patent Application No. 2008-556208 filed on Mar. 21, 2013 (with English translation).
The Argument and the Amendment for JP Patent Application No. 2008-516724 filed on Nov. 28, 2012 (with English translation).
The Explanation of Circumstances Concerning Accelerated Examination and the Amendment filed on May 10, 2012 for JP Patent Application No. 2011-527665 (with English translation).
The Argument and the Amendment for JP Patent Application No. 2009-123432 filed on Jun. 12, 2012 (with English translation).
The Argument and the Amendment for JP Patent Application No. 2009-529019 filed on Jul. 3, 2012 (with English translation).
Response to Office Action for CN Application No. 200780017371.9 dated May 29, 2013 with English translation.
Response to Office Action for U.S. Appl. No. 11/997,719, filed Jul. 3, 2013.
Office Action for JP Application No. 2009-540099 dated Jul. 2, 2013 (with English translation).
Notice of Allowance for CN Patent Application No. 201080030508.6 dated Jul. 4, 2013 (with English translation).
Notice of Allowance for JP Patent Application No. P2008-0556208 dated Jul. 9, 2013 (with English translation).
Matsui et al., "Extracellular matrix of linitis plastica as possible new therapeutic target", Surgical treatment 89(3):301-306 (Sep. 1, 2013) (with English translation).
Amendment for Application No. IL Patent Application No. 195282 dated Jul. 11, 2013 (with English translation).
Amended Claims for KR Patent Application 10-2010-7011023 dated Jul. 17, 2013 (with English translation).
Communication for EP Patent Application No. 10809938.3 dated Jul. 19, 2013.
Notice of Allowance for U.S. Appl. No. 12/524,754 dated Jul. 19, 2013.
Notice of Allowance for EP Patent Application No. 10015141.4 dated Jul. 1, 2013.
Response to Office Action for IL Patent Application No. 217197 dated Jul. 31, 2013 (with English translation).
Response to Communication for EP Patent Application No. 08846814.5 dated Aug. 1, 2013.
Office Action for CN Patent Application No. 200780017371.9 dated Jul. 3, 2013 (with English translation).
Office Action for MX Patent Application No. MX/a/2012/002011 dated Jul. 17, 2013 (with English translation).
Amendment (amending specification) for AU Patent Application No. 2012246490 dated Aug. 2, 2013.
Response to Office Action for EP Application No. 11798224.9 dated Aug. 2, 2013.
Nishio et al., "Phase 1 study of lenvatinib combined with carboplatin and paclitaxel in patients with non-small-cell lung cancer", British Journal of Cancer (2013), 109:538-544.
Amendment submitted for Korean Application No. 10-2008-7013685 dated Jul. 5, 2013 (with English translation).

(56) References Cited

OTHER PUBLICATIONS

Voluntary amendment for CA Patent Application No. 2704000 dated Aug. 6, 2013.
Amendment filed for JP Patent Application 2008-532141 dated Jul. 5, 2013 (with English translation).
Demand for Appeal Trial for JP Patent Application 2008-532141 dated Jul. 5, 2013 (with English translation).
Notice of Allowance for IL Patent Application No. 175363 dated Aug. 13, 2013 (with English translation).
Amendment filed for EP Application No. 12774278.1 dated Aug. 13, 2013.
Office Action for IL Patent Application No. 200090 dated Jul. 24, 2013 (with English translation).
Response to Office Action for U.S. Appl. No. 12/439,339 dated Aug. 22, 2013.
Communication to the Patent Office for CL Application No. 2012-00412 dated Aug. 31, 2012 (with English translation).
Communication to the Patent Office for AR Application No. P110100513 dated Aug. 27, 2013 (with English translation).
Notice of Allowance for U.S. Appl. No. 12/741,682 dated Jun. 19, 2013.
RCE and IDS filed for U.S. Appl. No. 13/083,338, filed Aug. 28, 2013.
Office Action for U.S. Appl. No. 13/238,085 dated Sep. 6, 2013.
Corrected English Translation for Office Action for JP Patent Application No. 2007-529565 dated Aug. 7, 2012.
Response to Office Action for MX Patent Application No. MX/a/2012/002011 dated Aug. 29, 2013 (with English Translation).
Final Office Action for U.S. Appl. No. 12/039,381 dated Sep. 12, 2013.
Preliminary Amendment for U.S. Appl. No. 14/002,018, filed Aug. 28, 2013.
Amended Claims for RU Patent Application No. 2013140169 dated Aug. 29, 2013 (with English translation).
Notice of Allowance for CN Application No. 200880115011.7 dated Aug. 5, 2013 (with English translation).
Amendment filed for JP Patent Application No. 2009-551518 dated Aug. 6, 2013 (with English translation).
Argument filed for JP Patent Application No. 2009-551518 dated Aug. 6, 2013 (partial English translation).
Response to Office Action for CA Patent Application No. 2652442 dated Sep. 5, 2013.
Amendment to claims for IN Patent Application No. 7026/CHENP/2013 dated Sep. 5, 2013.
Amendment filed for JP Patent Application No. 2009-540099 dated Aug. 13, 2013 (with English translation).
Argument filed for JP Patent Application No. 2009-540099 dated Aug. 13, 2013 (with partial English translation).
Preliminary Amendment filed for U.S. Appl. No. 13/805,826 dated Sep. 9, 2013.
Request for Continued Examination and Information Disclosure Statement for U.S. Appl. No. 13/205,328 dated Sep. 10, 2013.
Notice of Allowance for JP Patent Application No. P2008-532141 dated Sep. 10, 2013 (with English translation).
Amendments for CN Patent Application No. 201280010898.X dated Aug. 29, 2013 (with English translation).
Notice of Allowance for EP Patent Application No. 04818213.3 dated Sep. 19, 2013.
Request for Continued Examination and Information Disclosure Statement for U.S. Appl. No. 12/741,682, filed Sep. 19, 2013.
Amendment of Specification for AU Patent Application No. 2011270165 dated Sep. 23, 2013.
Office Action for PH Application No. 1-2011-502441 dated Oct. 1, 2013.
Amendment for IN Patent Application No. 10502/CHENP/2012 dated Oct. 1, 2013.
Response to Opposition for CL Patent Application No. 2012-00412 dated Oct. 2, 2013 (with English translation).
Office Action for KR 10-2008-7029472 dated Sep. 30, 2013 (in Korean).
Office Action for KR 10-2008-7029472 dated Sep. 30, 2013 (with English translation).
Ezzat et al., "Dual Inhibition of RET and FGFR4 Restraints Medullary Thyroid Cancer Cell Growth", Clinical Cancer Research, 11:1336-1341 (2005).
Sattler et al., "Targeting c-Kit mutations: basic science to novel therapies", Leukemia Research, 28S1:S11-S20 (2004).
Office Action for KR 10-2009-7005657 dated Sep. 30, 2013 (English translation).
Office Action for 10-2009-70056572 dated Sep. 30, 2013 (in Korean).
Notice of Allowance for U.S. Appl. No. 13/205,328 dated Oct. 3, 2013.
Response to Restriction Requirement for U.S. Appl. No. 13/238,085, filed Oct. 4, 2013.
Amendment for KR Patent Application No. 10-2012-7033886 dated Sep. 27, 2013 (with English translation).
Office Action for U.S. Appl. No. 11/997,543 dated Sep. 30, 2013.
Office Action for U.S. Appl. No. 12/022,608 dated Oct. 7, 2013 (with English translation).
Notice of Allowance for U.S. Appl. No. 13/083,338 dated Sep. 26, 2013.
Amendment for IL Patent Application No. 200090 dated Oct. 2, 2013 (with English translation).
St. Bernard et al., "Fibroblast Growth Factor Receptors as Molecular Targets in Thyroid Carcinoma", Endocrinology, 146(3):1145-1153 (2005).
Amendment filed for CA Patent Application No. 2828946 dated Aug. 30, 2013.
Notice of Allowance for U.S. Appl. No. 11/997,719 dated Sep. 13, 2013.
Amendment filed for RU Patent Application No. 2012158142 dated Oct. 17, 2013 (with English translation).
Amendment filed for MX Patent Application No. MX/a/2012/014776 dated Oct. 21, 2013.
Office Action for IN Application No. 6415/CHENP/2008 dated Oct. 3, 2013.
Request for Re-examination for CN Patent Application No. 200780017371.9 dated Oct. 11, 2013 (with English translation).
Office Action for MX Patent Application No. MX/a/2010/008187 dated Aug. 21, 2013 (with English translation).
RCE filed for U.S. Appl. No. 12/524,754, filed Oct. 18, 2013.
Request for Examination and Voluntary Amendment for CA Patent Application No. 2713930 dated Oct. 21, 2013.
Notice of Allowance for U.S. Appl. No. 12/741,682 dated Oct. 21, 2013.
Response to Office Action for IN Application No. 1571/CHENP/2007 dated Oct. 30, 2013.
RCE and Response to Final Office Action for U.S. Appl. No. 12/039,381 dated Oct. 23, 2013.
Response to Office Action for MX Patent Application No. MX/a/2010/008187 dated Nov. 4, 2013 (with English Translation).
Response to Office Action for PH Application No. 1-2011-502441 dated Nov. 4, 2013.
IPRP for PCT/JP2012/060279 dated Oct. 31, 2013.
Notice of Allowance for U.S. Appl. No. 12/439,339 dated Nov. 7, 2013.
Notice of Allowance for JP Patent Application No. P2009-551518 dated Oct. 22, 2013 (with English translation).
Office Action for U.S. Appl. No. 13/238,085 dated Nov. 12, 2013.
Office Action for CA Patent Application No. 2652442 dated Oct. 4, 2013.
Response to Office Action for CO Patent Application No. 12-022608 dated Nov. 13, 2013 (with English translation).
Amendment for BR Patent Application No. 112012032462-4 dated Nov. 4, 2013 (with English translation).
Wang, Y., "Drugs of Today, Everolimus in renal cell carcinoma", Journals of the Web, 46(8):Abstract, Aug. 2010.
Office Action for CN Patent Application No. 201180030568.2 dated Oct. 12, 2013 (with English translation).
Office Action for IN Patent Application No. 1571/CHENP/2007 dated Oct. 23, 2013.

(56) References Cited

OTHER PUBLICATIONS

Office Action for IL Patent Application No. 205512 dated Oct. 28, 2013 (with English translation).
Notice of Allowance for U.S. Appl. No. 12/524,754 dated Nov. 22, 2013.
Preliminary Amendment filed for U.S. Appl. No. 14/117,276, filed Nov. 12, 2013.
Preliminary Amendment filed for EP Patent Application No. 12786619.2 dated Nov. 13, 2013.
Voluntary Amendment filed for CA Patent Application No. 2802644 dated Nov. 22, 2013.
Amendment filed for KR Patent Application No. 10-2008-7029472 dated Nov. 20, 2013 (with English translation).
Amendment filed for EP Application No. 12793322.4 dated Nov. 28, 2013.
Request for Continued Examination and Information Disclosure Statement filed for U.S. Appl. No. 13/083,338 dated Dec. 2, 2013.
Almarsson et al., "High-Throughput Surveys of Crystal Form Diversity of Highly Polymorphic Pharmaceutical Compounds", Crystal Growth & Design, pp. 927-933 (2003).
Amendment for CO Application No. 12-022608 dated Jan. 28, 2014 (with English translation).
Amendment for IN Patent Application No. 1571/CHENP/2007 dated Jan. 23, 2014.
Amendment for KR Patent Application No. 10-2013-7020616 dated Nov. 22, 2013 (with English translation).
Amendment to Specification for KR Patent Application No. 10-2009-7017694 dated Feb. 28, 2014 (with English translation).
Argument for KR Patent Application No. 10-2009-7017694 dated Feb. 28, 2014 (with English translation).
Associate's comments about the Board of Appeal for EP Patent Application No. 04807580.8 dated Jul. 7, 2014.
Besson et al., "PTEN/MMAC1/TEP1 in signal transduction and tumorigenesis", European Journal of Biochemistry, 263:605-611 (1999).
Dankort et al., "Braf$^{V600E}$ cooperates with Pten loss to induce metastatic melanoma", Nature Genetics, 41(5):544-552 (2009).
Davies et al., "Mutations of the BRAF gene in human cancer", Nature 417:949-954 (2002).
Decision of Patent Grant for KR Patent Application No. 10-2008-7013685 dated Nov. 29, 2013 with English translation.
European Search Report for EP 09705712.9 dated Aug. 7, 2014.
European Search Report for EP 11798224.9 dated Mar. 4, 2014.
European Search Report for EP Patent Application No. 12774278.1 dated Aug. 14, 2014.
Final Office Action for U.S. Appl. No. 12/039,381 dated May 29, 2014.
Final Office Action for U.S. Appl. No. 11/997,543 dated Mar. 11, 2014.
Finn et al., "A multicenter, open-label, phase 3 trial to compare the efficacy and safety of lenvatinib (E7080) versus sorafenib in first-line treatment of subjects with unresectable hepatocellular carcinoma. ", American Society of Clinical Oncology, Annual Meeting Abstract, May 31, 2014.
Fuji et al., Angiogenesis Inhibitor/Kekkan Shinsei Sogaiyaku, Clinical Gastroenterology, 19:220-227 (2004) (with English translation).
Havel et al., "E7080 (lenvatinib) in addition to best supportive care (BSC) versus BSC alone in third-line or greater nonsquamous, non-small cell lung cancer (NSCLC).", American Society of Clinical Oncology, Annual Meeting Abstract, May 31, 2014.
Ikuta et al., "E7080, a Multi-Tyrosine Kinase Inhibitor, Suppresses the Progression of Malignant Pleural Mesothelioma with Different Proangiogenic Cytokine Production Profiles", Clinical Cancer Research, 15(23):7229-7237 (2009).
International Preliminary Report (IPRP) for PCT/US2012/040183 dated Apr. 3, 2014.
IPRP of International Patent Application No. PCT-JP2012-062509 dated Nov. 28, 2013.
Matsui et al., "Mechanism of antitumor activity of E70780, a selective VEGFR and FGFR tyrosine kinase inhibitor (TKI), in combination with selective mutant BRAF inhibition", Journal of Clinical Oncology, 29(15) (2011).
Matsui et al., "Multi-Kinase" Inhibitor E7080 Suppresses Lymph Node and Lung Metastases of Human Mammary Breast Tumor MDA-MB-231 via Inhibition of Vascular Endothelial Growth Factor•Receptor (VEGF-R) 2 and VEGF-R3 Kinase, Clinical Cancer Research, 14:459-465 (2008).
Nakagawa et al., E7050:A dual c-Met and VEGFR-2 tyrosine kinase inhibitor promotes tumor regression and prolongs survival in mouse xenograft models, Cancer Science 101(1):210-215 (2009).
Nakazawa et al., "Miximizing the efficacy of anti-angiogenesis cancer therapy: A multi-targeting strategy by tyrosine kinase inhibitors", Abstract No. 2980 Hall E-E, Poster Section 2 printed May 13, 2014.
Nakazawa et al., "Miximizing the efficacy of anti-angiogenesis cancer therapy: A multi-targeting strategy by tyrosine kinase inhibitors", AACR Annual Meeting, Abstract, Apr. 5-9, 2014.
Nakazawa, "Combination strategy of lenvatinib: Maximizing its anti-angiogenesis efficacy", Tsukuba Research Laboratory, Eisai Co., Ltd., Ibaraki, Japan, Jun. 27, 2014.
Notice of Allowance for U.S. Appl. No. 13/624,278 dated Jun. 25, 2014.
Notice of Allowance for CA Application No. 2652442 dated Apr. 16, 2014.
Notice of Allowance for IL Patent Application No. 200090 dated Nov. 18, 2013 (with English translation).
Notice of Allowance for Israel Patent Application No. 195282 dated Aug. 11, 2014.
Notice of allowance for Korean Patent Application No. 10-2009-7017694 dated Jul. 28, 2014 (with English translation).
Notice of Allowance for Mexican Patent Application MX/a/2010/008187 dated Jul. 17, 2014 (with English translation).
Notice of Allowance for U.S. Appl. No. 11/997,719 dated Jun. 5, 2014.
Notice of Allowance for U.S. Appl. No. 12/439,339 dated Apr. 1, 2014.
Notice of Allowance for U.S. Appl. No. 12/741,682 dated May 15, 2014.
Notice of Allowance for U.S. Appl. No. 13/083,338 dated Jul. 10, 2014.
Notice of Allowance for U.S. Appl. No. 13/205,328 dated Jan. 30, 2014.
Notice of Allowance for U.S. Appl. No. 13/205,328 dated May 8, 2014.
Notice of Allowance for UA Patent Application No. a201203132 dated Mar. 21, 2014 (with English translation).
Notice of Allowance for U.S. Appl. No. 12/741,682 dated Feb. 7, 2014.
Notice of Allowance for U.S. Appl. No. 13/083,338 dated Feb. 6, 2014.
Notice of Allowance for U.S. Appl. No. 12/524,754 dated Feb. 13, 2014.
Notice of Allowance for VN Application No. 1-2011-03484 dated Apr. 28, 2014 (with English translation).
Office Action for MX/a/2012/014776 dated Apr. 4, 2014 (with English translation).
Office Action for CA Application No. 2676796 dated Dec. 30, 2013.
Office Action for CA Patent Application No. 2771403 dated Jul. 16, 2014.
Office Action for CN Application No. 200680020317.5 dated Mar. 4, 2014 (with English translation).
Office Action for CN Application No. 201180030568.2 dated Mar. 24, 2014 (with English translation).
Office Action for CN Patent Application No. 200680020317.5 dated Nov. 28, 2013 dated Nov. 28, 2013 (with English translation).
Office Action for EP Application No. 03791389.4 dated Jun. 10, 2014.
Office Action for EP Application No. 04807580.8 dated Mar. 18, 2014.
Office Action for EP Application No. 08846814.5 dated Jun. 4, 2014.
Office Action for European Patent Application No. 08704376.6 dated Feb. 24, 2014.

(56) References Cited

OTHER PUBLICATIONS

Office Action for IN Patent Application No. 1571/CHENP/2007 dated Dec. 9, 2013.
Office Action for JP Application No. P2009-540099 dated Mar. 25, 2014 (with English translation).
Office Action for KR Application No. 10-2008-7029472 dated Mar. 28, 2014 (with English translation).
Office Action for KR Application No. 10-2009-7005657 dated Mar. 28, 2014 (with English translation).
Office Action for KR Application No. 10-2009-7017694 dated Jan. 29, 2014 (with English translation).
Office Action for MX Application No. MX/a/2010/008187 dated Apr. 28, 2014 (with Engish tranlsation).
Office Action for MX Application No. MX/a/2012/002011 dated Apr. 28, 2014 (with Engish tranlsation).
Office Action for MX Patent Application No. MX/a/2012/002011 dated Nov. 21, 2013 (with English translation).
Office Action for PH Application No. 1-2011-502441 dated Feb. 19, 2014.
Office Action for RU Application No. 2012103471 dated May 20, 2014 (with English translation).
Office Action for U.S. Appl. No. 11/662,425 dated Jun. 5, 2014.
Office Action for U.S. Appl. No. 12/039,381 dated Jan. 9, 2014.
Office Action for U.S. Appl. No. 12/864,817 dated Aug. 15, 2014.
Office Action for U.S. Appl. No. 13/805,826 dated Apr. 2, 2014.
Office Action for U.S. Appl. No. 13/805,826 dated Jul. 1, 2014.
Office Action for U.S. Appl. No. 13/923,858 dated Apr. 18, 2014.
Office Action for U.S. Appl. No. 14/002,018 dated Apr. 14, 2014.
Office Action for U.S. Appl. No. 14/002,018 dated Jul. 25, 2014.
Office Action for U.S. Appl. No. 14/002,018 dated Jun. 9, 2014.
Office Action for U.S. Appl. No. 11/662,425 dated Feb. 27, 2014.
Office Action for VN Application No. 1-2011-03484 dated Dec. 31, 2013 (with English translation).
Office Action of CO Patent Application No. 12-022608 Dec. 17, 2013 (with English translation).
Office Action of IL Patent Application No. 207089 dated Nov. 25, 2013 (with English translation).
Office Action of MX Patent Application No. MX-a-2010-008187 dated Dec. 5, 2013 (with English translation).
Official Notification for EP 04807580.8 dated Jun. 16, 2014.
Official Notification for EP 04807580.8 dated Jun. 27, 2014.
O'Reilly et al., "Hydrolysis of tert-Butyl Methyl Ether(MTBE) in Dilute -Aqueous Acid", Environ.Sci.Technol; 35, 2001, pp. 3954-3961.
Patel et al, "The effect of excipients on the stability of levothyroxine sodium pentahydrate tables", International Journal of Pharmaceutics; 264, pp. 35-43 (2003).
Preliminary Amendment filed for U.S. Appl. No. 14/122,339 dated Nov. 26, 2013.
Request for Continued Examination filed for U.S. Appl. No. 13/205,328 dated Dec. 30, 2013.
Response filed for SG Patent Application No. 201108602-2 dated May 22, 2014.
Request for Continued Examination filed for U.S. Appl. No. 11/997,719 dated Dec. 11, 2013.
Request for Continued Examination filed for U.S. Appl. No. 13/083,338 dated May 6, 2014.
Request for Continued Examination filed for U.S. Appl. No. 12/741,682 dated May 6, 2014.
Request for Continued Examination for U.S. Appl. No. 13/205,328 dated Apr. 28, 2014.
Request for Continued Examination for U.S. Appl. No. 12/741,682 dated Aug. 14, 2014.
Request for Continued Examination for U.S. Appl. No. 12/439,339 dated Jan. 27, 2014.
Request for Continued Examination for U.S. Appl. No. 12/741,682 dated Jan. 17, 2014.
Request for Continued Examination for U.S. Appl. No. 12/524,754 dated Feb. 3, 2014.
Request for Continued Examination for U.S. Appl. No. 12/524,754 dated May 13, 2014.
Response filed for EP Patent Application No. 04807580.8 dated May 16, 2014.
Response filed for IN Patent Application No. 6415/CHENP/2008 dated Jan. 17, 2014.
Response filed for KR Application No. 10-2009-7005657 dated Nov. 21, 2013 (with English translation).
Response filed for KR Patent Application No. 10-2008-7029472 dated May 1, 2014 (with English translation).
Response filed for KR Patent Application No. 10-2009-7005657 dated May 7, 2014 (with English translation).
Response to CN Application No. 201180030568.2 dated Jan. 13, 2014 (with English translation).
Response to Office Action and Information Disclosure Statement filed for U.S. Appl. No. 11/997,543 dated Dec. 19, 2013).
Response to Office Action for CA Patent Application No. 2652442 dated Jan. 8, 2014.
Response to Office Action for CN 2006800203175 filed on Jan. 9, 2014 (with English translation).
Response to Office Action for CN Application No. 201180030568.2 dated May 14, 2014 (with English translation).
Response to Office Action for EP Application No. 08704376.6 dated Apr. 30, 2014.
Response to Office Action for JP2009-540099 dated Apr. 28, 2014, (with English translation).
Response to Office Action for MX Patent Application No. MX/a/2010008187 dated Feb. 17, 2014 (with English translation).
Response to Office Action for MX-a-2012-002011 dated Jan. 16, 2014 (with English translation).
Response to Office Action for Philippines Patent Application No. 1-2011-502441 dated Feb. 28, 2014.
Response to Office Action for U.S. Appl. No. 11/662,425 dated May 20, 2014.
Response to Office Action for U.S. Appl. No. 12/039,381 dated Apr. 3, 2014.
Response to Office Action for U.S. Appl. No. 13/805,826 dated Aug. 8, 2014.
Response to Office Action for U.S. Appl. No. 13/923,858 dated Aug. 8, 2014.
Response to Office Action for U.S. Appl. No. 14/002,018 dated May 28, 2014.
Response to Office Action for U.S. Appl. No. 14/002,018 dated Jul. 18, 2014.
Search Report for EP Patent Application No. 11798224.9 dated Mar. 21, 2014.
Sehlumberger et aI, "A phase 3, multicenter, double-blind, placebo•controlled trial of lenvatinib (E7080) in patients with 1311 refractory differentiated thyroid cancer (SELECT).", American Society of Clinical Oncology, Annual Meeting Abstract, Jun. 2, 2014.
Shumaker et al., "Effect of lenvatinib (E7080) on the QTc interval: results from a thorough QT study in healthy volunteers", Cancer Chemother Pharmacol, Springer-Verlag Berlin Heidelberg (2014) (online).
Søndergaard et al., "Differential sensitivity of melanoma cell lines with BRAFV600E mutation to the specific Raf inhibitor PLX4032", Journal of Translational Medicine, Biomed, Central London, GB 8(1):39 (2010).
Stahl and Wermuth, Handbook of Pharmaceutical Salts: Properties, Selection and Use, pp. 117-122 (2002).
Submission of Documents for EP Patent Application No. 08846814.5 dated Jul. 24, 2014.
Submission of Documents for RU Patent Application No. 2012103471 dated Jul. 21, 2014.
Submission for EP 04807580.8 dated Jun. 13, 2014.
Submission for EP 04807580.8 dated Jun. 16, 2014.
Submission for VN Application No. 1-2011-03484 dated Feb. 28, 2014 (with English translation).
Submission of documents for EP Patent Application No. 03791389.4 dated Jul. 25, 2014.
Submission of Document for CA Application No. 2676796 dated Jun. 27, 2014.

(56) References Cited

OTHER PUBLICATIONS

Submission of Document for U.S. Appl. No. 13/205,328 dated Jul. 8, 2014.
Submission of Documents for Korean Patent Application No. 10-2012-7003846 dated Jun. 18, 2014 (with English translation).
Submission of Documents for MX Application No. MX/a/2010/008187 dated Jun. 25, 2014 (with English translation).
Submission of Documents for MX Application No. MX/a/2012/014776 dated Jun. 20, 2014 (with English translation).
Submission of Documents for MY Patent Application No. P12011700172 dated Jul. 3, 2014 (in English).
Submission of Documents for U.S. Appl. No. 13/805,826 dated Jun. 2, 2014.
Tahara et al., "Lenvatinib in radioactive-iodine-refractory differentiated thyroid cancer. Results of the Phase 3 trial (SELECT trial ), 1-81-1, Abstract and Presentation Document", The 12th Annual Meeting of Japanese Society of Medical Oncology, Jul. 17, 2014.
Vergote et al., "Prognostic and predictive role of circulating angiopoietin-2 in multiple solid tumors; An analysis of approximately 500 patients treated with lenvatinib across tumor types.", American Society of Clinical Oncology, Annual Meeting Abstract, May 31, 2014.
Wang et al., "KRAS, BRAF, PIK3CA Mutations and PTEN Expression in Human Colorectal Cancer-Relationship With Metastatic Colorectal Cancer", Ann. Oncol. 21(Supp 6), p. 64, Jan. 2010.
Winkler et al., "Kinetics of vascular normalization by VEGFR2 blockade governs brain tumor response to radiation: Role of oxygenation, angiopoietin-1, and matrix metalloproteinases", Cancer Cell vol. 6:553-563 (2004).
Yamori et al., Current Treatment of Solid Tumors New Approaches of Treatment, Drug Treatment Kinase Inhibitors/Kokeigan no Saishin Chiryo Chiryo no Aratana Torikumi Yakubutsu Ryoho Kinase Inhibitors, Japanese Journal of Clinical Medicine 68(6):1059-1066 (2010) (with English translation).
Yang et al., "RG7204(PLX4032), a Selective BRAFv600E Inhibitor, Displays Potent Antitumor Activity in Preclinical Melanoma Models", Cancer Research 70(13):5518-5527 (2010).
Yokota, "ASCO report: Gastrointestinal Cancer field/ASCO Hokoku Shokakigan Ryoiki", Gan Bunshi Hyoteki Chiryo, 8(4):271-283 (2010) (with English translation).
Zhang et al. "Synergic antiproliferative effect of DNA methyltransferase inhibitor in combination with anticancer drugs in gastric carcinoma", Cancer Science, vol. 97, No. 9, Sep. 2006, pp. 938-944.

METHOD FOR ASSAY ON THE EFFECT OF VASCULARIZATION INHIBITOR

CROSS REFERENCE TO RELATED APPLICATIONS

This is a divisional of co-pending U.S. patent application Serial No. 11/997,719 which was filed in the United States Patent and Trademark Office on Feb. 28, 2008 in accordance with 35 U.S.C. § 371, as the U.S. National Phase of International patent application No. PCT/JP2006/315698 filed on Aug. 2, 2006. Said International patent application No. PCT/JP2006/315698 claims priority to application nos. JP 2006-164700 and 2005-224173 filed in Japan on Jun. 14, 2006 and Aug. 2, 2005, respectively. The contents of these prior applications are incorporated herein by reference in their entireties.

TECHNICAL FIELD

The present invention relates to a novel method for predicting the effect of angiogenesis inhibitors, such as substances having vascular endothelial growth factor (hereinafter, sometimes referred to as "VEGF") inhibitory activity (hereinafter, sometimes referred to as "VEGF inhibitors").

The present invention also relates to a pharmaceutical composition comprising a combination of a VEGF receptor kinase inhibitor and a substance having EGF inhibitory activity (hereinafter, sometimes referred to as "EGF inhibitor"); a kit comprising the composition; and a method of treating cancers.

BACKGROUND ART

Clinical trials have made it clear that angiogenesis inhibitors are useful as antitumor agents. For example, bevacizumab that is an antibody neutralizing VEGF, one of the most important angiogenic processes, is reported to have shown an antitumor effect against colorectal cancer in clinical trials (Reference 5).

As an angiogenesis inhibitor, 4-(3-chloro-4-(cyclopropylaminocarbonyl)aminophenoxy)-7-methoxy-6-quinolinecarboxamide is known (References 1, 2 and 3).

Evaluating the effect of angiogenesis inhibitors, determining the effective dose of angiogenesis inhibitors and predicting the effect of angiogenesis inhibitors prior to administration thereof are very useful for efficiently performing treatment with angiogenesis inhibitors and for contributing to the improvement of patients' QOL (Reference 6). With respect to the former two matters, a great number of researches are now being carried out (Reference 7). Specifically, methods such as dynamic contrast-enhanced magnetic resonance imaging (DCE-MRI), positron emission tomograpy (PET), interstitial fluid pressure and serum VEGF are known. Among all, DCE-MRI is believed to be effective as a method for evaluating the effect of angiogenesis inhibitors (Reference 8).

On the other hand, predicting the effect of angiogenesis inhibitors is very beneficial and important to patients for avoiding the administration of inefficient medicine and reducing adverse effect (Reference 6). However, no effective method for predicting the effect of angiogenesis inhibitors prior to administration thereof has been found yet.

Recently, methods of cancer treatment using a substance with VEGF inhibitory activity and a substance with EGF inhibitory activity in combination have been reported (References 4 and 9 to 11). However, it has not been elucidated yet what specific substances with VEGF inhibitory activity and EGF inhibitory activity are effective for cancer treatment.

REFERENCES

1. WO 02/32872
2. WO 2004/080462
3. WO 2005/063713
4. WO 2002/041882
5. Bevacizumab plus irinotecan, fluorouracil, and leucovorin for metastatic colorectal cancer, New England Journal of Medicine. 2004, 350, 2335-2342.
6. Inhibition of vascular endothelial growth factor (VEGF) signaling in cancer causes loss of endothelial fenestrations, regression of tumor vessels, and appearance of basement membrane ghosts. American Journal of Pathology., 2004, 165, 35-52.
7. Direct evidence that the VEGF-specific antibody bevacizumab has antivascular effects in human rectal cancer, Nature Medicine, 2004, 10, 145-147.
8. Dynamic contrast-enhanced magnetic resonance imaging as a biomarker for the pharmacological response of PTK787/ZK 222584, an inhibitor of the vascular endothelial growth factor receptor tyrosine kinases, in patients with advanced colorectal cancer and liver metastases: results from two phase I studies, Journal of Clinical Oncology., 2003, 21, 3955-3964.
9. The Antitumor and Antiangiogenic Activity of Vascular Endothelial Growth Factor Receptor Inhibition Is Potentiated by ErbB1 Blockade. Clinical Cancer Research. 2005, 1, 4521-4532.
10. Effects of combination anti-vascular endothelial growth factor receptor and anti-epidermal growth factor receptor therapies on the growth of gastric cancer in a nude mouse model, European Journal of Cancer. 2002, 38, 1133-1140.
11. Blockade of Vascular Endothelial Growth Factor Receptor and Epidermal Growth Factor Receptor Signaling for Therapy of Metastatic Human Pancreatic Cancer, Cancer Research. 2002, 62, 1996-2003.

DISCLOSURE OF THE INVENTION

Under such circumstances, the present invention has been made. It is an object of the invention to find a method for predicting the effect of angiogenesis inhibitors.

It is another object of the present invention to find a pharmaceutical composition having excellent antitumor effect, a kit having the same, and a method of treating cancers.

As a result of extensive and intensive researches toward the solution of the above problems, the present inventors have found that the antitumor effect of an angiogenesis inhibitor 4-(3-chloro-4-(cyclopropylaminocarbonyl)aminophenoxy)-7-methoxy-6-quinolinecarboxamide correlates with the expression level and/or the degree of phosphorylation of epidermal growth factor (hereinafter, sometimes abbreviated to "EGF") receptor.

More specifically, the inventors have examined the antitumor effect of 4-(3-chloro-4-(cyclopropylaminocarbonyl)aminophenoxy)-7-methoxy-6-quinolinecarboxamide against in vivo models in which 15 types of human cancer cell lines were subcutaneously transplanted, and then classified the 15 types of human cancer cell lines into high sensitive lines (3), medium sensitive lines (4) and low sensitive lines (8) based on the degree of antitumor effect against them.

Subsequently, the expression level and the degree of phosphorylation of EGF receptor in individual cell lines proliferated subcutaneously in the human cancer cell line transplanted models were analyzed by Western blotting.

When the expression level and the degree of phosphorylation of EGF receptor in individual cell lines were compared with the sensitivity to 4-(3-chloro-4-(cyclopropylaminocarbonyl)aminophenoxy)-7-methoxy-6-quinolinecarboxamide in those cell lines, a significant amount of expression and/or a significant degree of phosphorylation of EGF receptor was recognized in 6 cell lines out of the 7 lines of high sensitivity and medium sensitivity. However, in low sensitivity lines, a significant amount of expression and/or a significant degree of phosphorylation of EGF receptor was recognized in only one cell line out of the 8 lines.

Since it is believed that the expression level and/or the degree of phosphorylation of EGF receptor in tumor cells reveals the EGF dependency of individual cell lines when they proliferate and/or survive, it has become clear that cancer cell lines with higher EGF dependency have higher sensitivity to 4-(3-chloro-4-(cyclopropylaminocarbonyl)aminophenoxy)-7-methoxy-6-quinolinecarboxamide.

Therefore, the inventors have found that it is possible to predict the antitumor effect of angiogenesis inhibitors, without administration to patients, by evaluating the EGF dependency of a tumor cell for proliferation and/or survival and using the evaluated EGF dependency for proliferation and/or survival as an indicator.

Further, since the antitumor effect of angiogenesis inhibitors correlates with the EGF dependency of tumor cells for proliferation and/or survival, it has been found that angiogenesis inhibitors manifest superior antitumor effect when used in combination with EGF inhibitors.

It has been confirmed that 4-(3-chloro-4-(cyclopropylaminocarbonyl)aminophenoxy)-7-methoxy-6-quinolinecarboxamide shows excellent antitumor effect when used in combination with an EGF inhibitor 4-(3-ethylnylphenylamino)-6,7-bis(2-methoxyethoxy)-quinazoline (hereinafter, sometimes referred to as "erlotinib").

The present invention relates to the following.
1. A method of predicting the antitumor effect of an angiogenesis inhibitor, comprising a step of evaluating the EGF dependency of a tumor cell for proliferation and/or survival and a step of judging whether or not a cancer patient is highly sensitive to the angiogenesis inhibitor by using the evaluated EGF dependency as an indicator.

In the present invention, the tumor cell may be a cell collected from the cancer patient.

In the present invention, the evaluation of EGF dependency may be performed using, as an indicator, the expression level of at least one substance selected from the group consisting of TGF-α, HB-EGF, EGF, epiregulin and EGF receptor. Alternatively, the evaluation may be performed using, as an indicator, the degree of phosphorylation of EGF receptor. The determination of the phosphorylation of EGF receptor may be performed by an immunochemical method such as Western blotting.

The angiogenesis inhibitors which is a target of the method of the present invention is, for example, a VEGF receptor kinase inhibitor. Examples of VEGF receptor kinase inhibitors may be given as follows.

A compound represented by the following general formula (I), a pharmacologically acceptable salt thereof, or a solvate of the compound or the salt:

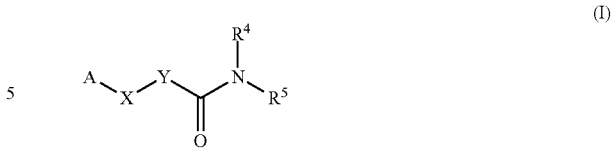

wherein A is a group represented by one of the following formulas:

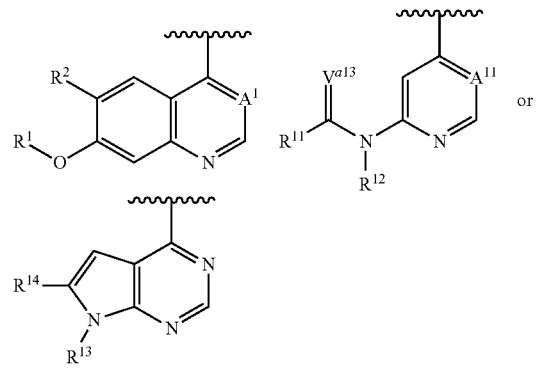

(wherein $R^1$ is a group represented by a formula —$V^1$—$V^2$—$V^3$ (where $V^1$ is a $C_{1-6}$ alkylene group which may have a substituent(s); $V^2$ is a single bond, an oxygen atom, a sulfur atom, a carbonyl group, a sulfinyl group, a sulfonyl group, a group represented by a formula —$CONR^6$—, a group represented by a formula —$SO_2NR^6$—, a group represented by a formula —$NR^6SO_2$—, a group represented by a formula —$NR^6CO$— or a group represented by a formula —$NR^6$— (where $R^6$ is a hydrogen atom, a $C_{1-6}$ alkyl group which may have a substituent(s) or a $C_{3-8}$ cycloalkyl group which may have a substituent(s)); and $V^3$ is a hydrogen atom, a $C_{1-6}$ alkyl group which may have a substituent(s), a $C_{2-6}$ alkenyl group which may have a substituent(s), a $C_{2-6}$ alkynyl group which may have a substituent(s), a $C_{3-8}$ cycloalkyl group which may have a substituent(s); a $C_{6-10}$ aryl group which may have a substituent(s), a 5- to 10-membered heteroaryl group which may have a substituent(s) or a 3- to 10-membered non-aromatic heterocyclic group which may have a substituent(s)); $R^2$ is a cyano group, a $C_{1-6}$ alkoxy group which may have a substituent(s), a carboxyl group, a $C_{2-7}$ alkoxycarbonyl group which may have a substituent(s) or a group represented by a formula —$CONV^{a11}V^{a12}$ (where $V^{a11}$ is a hydrogen atom, a $C_{1-6}$ alkyl group which may have a substituent(s), a $C_{2-6}$ alkenyl group which may have a substituent(s), a $C_{2-6}$ alkynyl group which may have a substituent(s), a $C_{3-8}$ cycloalkyl group which may have a substituent(s); a $C_{6-10}$ aryl group which may have a substituent(s), a 5- to 10-membered heteroaryl group which may have a substituent(s) or a 3- to 10-membered non-aromatic heterocyclic group which may have a substituent(s); and $V^{a12}$ is a hydrogen atom, a $C_{1-6}$ alkyl group which may have a substituent(s), a $C_{2-6}$ alkenyl group which may have a substituent(s), a $C_{2-6}$ alkynyl group which may have a substituent(s), a $C_{3-8}$ cycloalkyl group which may have a substituent(s); a $C_{6-10}$ aryl group which may have a substituent(s), a 5- to 10-membered heteroaryl group which may have a substituent(s), a 3- to 10-membered non-aromatic heterocyclic group which may have a substituent(s), a hydroxyl group, a alkoxy group which may have a substituent(s) or a $C_{3-8}$ cycloalkoxy group which may have a substituent(s));

$A^1$ is a carbon atom which may have a substituent or a nitrogen atom;

$R^{11}$ is a hydrogen atom, a alkyl group which may have a substituent(s), a $C_{2-6}$ alkenyl group which may have a substituent(s), a $C_{2-6}$ alkynyl group which may have a substituent(s), a $C_{3-8}$ cycloalkyl group which may have a substituent(s); a $C_{6-10}$ aryl group which may have a substituent(s), a 5- to 10-membered heteroaryl group which may have a substituent(s), a 3- to 10-membered non-aromatic heterocyclic group which may have a substituent(s) or a mono-$C_{1-6}$ alkylamino group which may have a substituent(s);

$R^{12}$ is a hydrogen atom or a $C_{1-6}$ alkyl group which may have a substituent(s);

$V^{a13}$ is an oxygen atom or a sulfur atom;

$A^{11}$ is a carbon atom which may have a substituent or a nitrogen atom;

$R^{13}$ is a hydrogen atom, a Cu alkyl group which may have a substituent(s) or a $C_{3-8}$ cycloalkyl group which may have a substituent(s);

$R^{14}$ is a group represented by a formula —$V^{a14}$—$V^{a15}$ (where $V^{a14}$ is a single bond or a carbonyl group; and $V^{a15}$ is a hydrogen atom, a hydroxyl group, a $C_{1-6}$ alkyl group which may have a substituent(s), a $C_{2-6}$ alkenyl group which may have a substituent(s), a $C_{2-6}$ alkynyl group which may have a substituent(s), a $C_{3-8}$ cycloalkyl group which may have a substituent(s): a $C_{6-10}$ aryl group which may have a substituent(s), a 5- to 10-membered heteroaryl group which may have a substituent(s), a 3- to 10-membered non-aromatic heterocyclic group which may have a substituent(s), an amino group, a mono-$C_{1-6}$ alkylamino group which may have a substituent(s), a di-$C_{1-6}$ alkylamino group which may have a substituent(s), a formyl group, a carboxyl group or a $C_{2-7}$ alkoxycarbonyl group which may have a substituent(s));

X is an oxygen atom or a sulfur atom;
Y is a group represented by one of the following formulas:

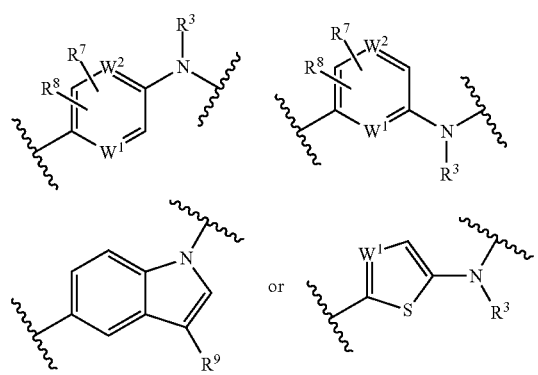

(wherein $R^3$ is a hydrogen atom, a $C_{1-6}$ alkyl group which may have a substituent(s), a $C_{2-6}$ alkenyl group which may have a substituent(s), a $C_{2-6}$ alkynyl group which may have a substituent(s), a $C_{3-8}$ cycloalkyl group which may have a substituent(s), a $C_{2-7}$ acyl group which may have a substituent(s) or a $C_{2-7}$ alkoxycarbonyl group which may have a substituent(s);

$R^7$ and $R^8$ independently of each other represent a hydrogen atom, a halogen atom, a cyano group, a nitro group, an amino group, a $C_{1-6}$ alkyl group which may have a substituent(s), a $C_{3-8}$ cycloalkyl group which may have a substituent(s), a $C_{1-6}$ alkoxy group which may have a substituent(s), a $C_{1-6}$ alkylthio group which may have a substituent(s), a formyl group, a $C_{2-7}$ acyl group which may have a substituent(s), a $C_{2-7}$ alkoxycarbonyl group which may have a substituent(s) or a group represented by a formula —$CONV^{d1}V^{d2}$ (where $V^{d1}$ and $V^{d2}$ independently of each other represent a hydrogen atom or a $C_{1-6}$ alkyl group which may have a substituent(s));

$R^9$ is a hydrogen atom, a halogen atom or a $C_{1-6}$ alkyl group which may have a substituent(s); and $W^1$ and $W^2$ independently of each other represent a carbon atom which may have a substituent or a nitrogen atom);

$R^4$ is a hydrogen atom, a $C_{1-6}$ alkyl group which may have a substituent(s), a $C_{2-6}$ alkenyl group which may have a substituent(s), a $C_{2-6}$ alkynyl group which may have a substituent(s), a $C_{3-8}$ cycloalkyl group which may have a substituent(s), a $C_{2-7}$ acyl group which may have a substituent(s) or a $C_{2-7}$ alkoxycarbonyl group which may have a substituent(s); and $R^5$ is a hydrogen atom, a $C_{1-6}$ alkyl group which may have a substituent(s), a $C_{2-6}$ alkenyl group which may have a substituent(s), a $C_{2-6}$ alkynyl group which may have a substituent(s), a $C_{3-8}$ cycloalkyl group which may have a substituent(s), a $C_{6-10}$ aryl group which may have a substituent(s), a 5- to 10-membered heteroaryl group which may have a substituent(s) or a 3- to 10-membered non-aromatic heterocyclic group which may have a substituent(s).

Further, in the present invention, the following compounds may be enumerated as examples of VEGF receptor kinase inhibitors.

At least one compound selected from the group consisting of:

(1) N-(4-bromo-2-fluorophenyl)-6-methoxy-7-[2-(1H-1,2,3-triazole-1-yl)ethoxy]-quinazoline-4-amine
(2) N-(4-bromo-2-fluorophenyl)-6-methoxy-7-[(1-methylpiperidine-4-yl)methoxy]-quinazoline-4-amine
(3) 3-[(2,4-dimethylpyrrol-5-yl)methylene]-2-indolinone
(4) (Z)-3-[(2,4-dimethyl-5-(2-oxo-1,2-dihydroindole-3-ylidenemethyl)-1H-pyrrole-3-yl)propionic acid
(5) 5-(5-fluoro-2-oxo-1,2-dihydro indole-3-ylidenemethyl)-2,4-dimethyl-1H-pyrrole-3-carboxylic acid (2-diethylaminoethyl)amide
(6) N,N-dimethylglycine-3-{5,6,7,13-tetrahydro-9-[(1-methylethoxy)methyl]-5-oxo-12H-indeno (2,1-a)pyrrolo[3,4-c]carbazole-12-yl}propylester
(7) 3-(4-bromo-2,6-difluoro-benzyloxy)-5-[3-(4-pyrrolizine-1-yl-butyl)-ureido]-isothiazole-4-carboxylic acid amide
(8) N-{2-chloro-4-[(6,7-dimethoxy-4-quinazolinyl)oxy]phenyl}-N'-propylurea
(9) 1-(4-chloroanilino)-4-(4-pyridylmethyl)phthalazine
(10) N-{2-chloro-4-[(6,7-dimethoxy-4-quinolyl)oxy]phenyl}-N'-[5-methyl-3-isoxazolyl]-urea
(11) 4-[(4-fluoro-2-methylindole-5-yl)oxy]-6-methoxy-7-[3-(pyrrolizine-1-yl)propoxy]-quinazoline
(12) 6-[2-(methylcarbamoyl)phenylsulphanyl]-3-E-[2-(pyridine-2-yl)ethenyl]indazole
(13) 5-((Z)-(5-fluoro-2-oxo-1,2-dihydro-3H-indole-3-ylidene)methyl)-N-((2S)-2-hydroxy-3-morpholine-4-yl-propyl)-2,4-dimethyl-1H-pyrrole-3-carboxamide
(14) 3-((quinoline-4-ylmethyl)amino)-N-(4-(trifluoromethoxy)phenyl)thiophene-2-carboxamide
(15) 6-(2,6-dichlorophenyl)-8-methyl-2-phenylamino-8H-pyrido[2,3-d]pyrimidine-7-one
(16) 2-((1,6-dihydro-6-oxo-pyridine-3-ylmethyl)amino)-N-(3-(trifluoromethyl)phenyl)-3-pyridine-carboxamide
(17) 4-(4-(4-chloro-phenylamino)-furo[2,3-d]pyridazine-7-yloxymethyl)-pyridine-2-carboxylic acid methylamide
(18) N-(3-trifluoromethyl-4-chlorophenyl)-N'-(4-(2-methyl-carbamoylpyridine-4-yl)oxyphenyl)urea

(19) 4-amino-5-fluoro-3-(6-(4-methyl-piperazine-1-yl)-1H-benzimidazole-2-yl)-1H-quinoline-2-one
(20) 4-(4-(1-amino-methyl-ethyl)-phenyl)-2-(4-(2-morpholine-4-yl-ethyl)-phenylamino)pyrimidine-5-carbonitrile
(21) [6-[4-[(4-ethylpiperazine-1-yl)methyl]phenyl]-7H-pyrrolo[2,3-d]pyrimidine-4-yl]-((R)-1-phenylethyl)amine
(22) 9-(1-methylethoxy)methyl-12-(3-hydroxypropyl)-6H,7H,13H-indeno[2,1-a]-pyrrole[3,4-c]carbazole-5-one
(23) N-(2,4-difluorophenyl)-N'-{4-[(6,7-dimethoxy-4-quinolyl)-oxy]-2-fluorophenyl}urea
(24) N-[4-(3-amino-1H-imidazole-4-yl)phenyl]-N'-(2-fluoro-5-methylphenyl)urea
(25) 2-methyl-6-[2-(1-methyl-1H-imidazole-2-yl)-thieno[3,2-b]pyridine-7-yloxy]-benzo[b]thiophene-3-carboxylic acid methylamide
(26) (R)-1-(4-(4-fluoro-2-methyl-1H-indole-5-yloxy)-5-methylpyrrolo[1,2-f]-[1,2,4]triazine-6-yloxy)propane-2-ol
(27) (S)—((R)-1-(4-(4-fluoro-2-methyl-1H-indole-5-yloxy)-5-methylpyrrolo[1,2-f]-[1,2,4]triazine-6-yloxy)propane-2-ol)2-aminopropanoate
(28) 3-[(4-morpholine-4-yl-phenylamino)-methylene]-1,3-dihydroindole-2-one
(29) 5-[[4-[(2,3-dimethyl-2H-indazole-6-yl)methylamino]pyrimidine-2-yl]amino]-2-methylbenzenesulfonamide
(30) (3Z)-3-[6-(2-morpholine-4-ylethoxy)quinoline-2(1H)-ylidene]-1,3-dihydro-2H-indole-2-one, and
(31) 2-((2-((4-(4-(4-(tert-butyl)anilino)phenoxy)-6methoxy-7-quinolyl)oxy)ethyl)amino)-1-ethanol;
or a pharmacologically acceptable salt of the compound, or a solvate of the compound or the salt.

The angiogenesis inhibitor of interest in the method of the present invention may be at least one selected from the group consisting of anti-VEGF receptor antibody, anti-VEGF antibody, FGF receptor kinase inhibitor, PDGF receptor kinase inhibitor, EGF receptor kinase inhibitor, anti-FGF receptor antibody, anti-PDGF receptor antibody, anti-EGF receptor antibody, anti-FGF antibody anti-PDGF antibody and anti-EGF antibody.

2. The present invention provides the following kits (1) to (4), which are for use in the method described in item 1 above.
(1) A kit comprising at least one antibody selected from the group consisting of anti-TGF-α antibody, anti-HB-EGF antibody, anti-EGF antibody, anti-epiregulin antibody, anti-EGF receptor antibody, anti-phosphorylated EGF receptor antibody and anti-phosphorylated antibody.
(2) A kit comprising an anti-EGF receptor antibody and/or an anti-phosphorylated EGF receptor antibody.
(3) A kit comprising a polynucleotide comprising a sequence complementary to at least a part of a transcript RNA from at least one gene selected from the group consisting of TGF-α gene, HB-EGF gene, EGF gene, epiregulin gene and EGF receptor gene.
(4) A kit comprising a polynucleotide comprising a sequence complementary to at least a part of a transcript RNA from EGF receptor gene.

3. A pharmaceutical composition comprising a VEGF receptor kinase inhibitor in combination with a substance having EGF inhibitory activity.

In the pharmaceutical composition of the present invention, those substances enumerated in 1 above may be used as the VEGF receptor kinase inhibitor. The substance having EGF inhibitory activity may be at least one substance selected from the group consisting of EGF receptor kinase inhibitor, anti-EGF receptor antibody and anti-EGF antibody.

Specific examples of EGF receptor kinase inhibitors may be given as follows.

At least one compound selected from the group consisting of:
(1) 4-(3-chloro-4-fluorophenylamino)-7-methoxy-6-(3-(4-morpholino)propoxy-quinazoline)
(2) 4-(3-ethynylphenylamino)-6,7-bis(2-methoxyethoxy)-quinazoline
(3) N-[3-chloro-4-[(3-fluorobenzyl)oxy]phenyl]-6-[5-[[[2-(methylsulfonyl)ethyl]-amino]methyl]furan-2-yl]quinazoline-4-amine
(4) N-[4-[N-(3-chloro-4-fluorophenyl)amino]-7-[3-(4-morpholinyl)propoxy]-quinazoline-6-yl]acrylamide
(5) (2E)-N-[4-[(3-chloro-4-fluorophenyl)amino]-3-cyano-7-ethoxy-6-quinolinyl]-4-(dimethylamino)-2-butenamide
(6) [6-[4-[(4-ethylpiperazine-1-yl)methyl]phenyl]-7H-pyrrolo[2,3-d]pyrimidine-4-yl]-((R)-1-phenylethyl)amine, and
(7) (E)-N-{4-[3-chloro-4-(2-pyridinylmethoxy)anilino]-3-cyano-7-ethoxy-6-quinolinyl}-4-(dimethylamino)-2-butenamide;
or a pharmacologically acceptable salt of the compound, or a solvate of the compound or the salt.

Preferably, the EGF receptor kinase inhibitor is 4-(3-ethynylphenylamino)-6,7-bis(2-methoxyethoxy)-quinazoline, a pharmacologically acceptable salt thereof, or a solvate of this compound or the salt.

As the EGF receptor antibody, at least one antibody selected from the group consisting of cetuximab, panitumumab, matuzumab, nimotuzunab, IMC-11F8 and MDX-447 may be given.

4. A kit comprising the following (a) and (b):
(a) at least one selected from the group consisting of a wrapping container, a handling instruction and an accompanying document, each of which is stating that a VEGF receptor kinase inhibitor and a substance having EGF inhibitory activity should be used in combination, and
(b) a pharmaceutical composition comprising a VEGF receptor kinase inhibitor.

In the kit of the present invention, the VEGF receptor kinase inhibitor and the substance having EGF inhibitory activity may be the substances illustrated in items 1 and 3 above, respectively.

5. A kit characterized by containing a combination of a preparation comprising a VEGF receptor kinase inhibitor and a preparation comprising a substance having EGF inhibitory activity.

In the kit of the present invention, the VEGF receptor kinase inhibitor and the substance having EGF inhibitory activity may be the substances illustrated in items 1 and 3 above, respectively.

6. A pharmaceutical composition comprising a VEGF receptor kinase inhibitor, which is to be administered in combination with a substance having EGF inhibitory activity.

In the pharmaceutical composition of the present invention, the VEGF receptor kinase inhibitor and the substance having EGF inhibitory activity may be the substances illustrated in items 1 and 3 above, respectively.

7. The present invention provides use of a VEGF receptor kinase inhibitor in preparing a pharmaceutical composition comprising a combination of a substance having EGF inhibitory activity and a VEGF receptor kinase inhibitor.

In the use of the present invention, the VEGF receptor kinase inhibitor and the substance having EGF inhibitory activity may be the substances illustrated in items 1 and 3 above, respectively.

8. The present invention also provides a method of treating a cancer, which is characterized by combined administration (e.g., administration to a patient simultaneously or separately) of a VEGF receptor kinase inhibitor and a substance having EGF inhibitory activity. In the cancer treating method of the present invention, the VEGF receptor kinase inhibitor and the substance having EGF inhibitory activity may be the substances illustrated in items 1 and 3 above, respectively.

According to the present invention, a method of predicting the antitumor effect of angiogenesis inhibitors is provided.

More specifically, it has become possible to predict the antitumor effect of angiogenesis inhibitors by evaluating the EGF dependency of a tumor cell for proliferation and/or survival and using the resultant EGF dependency as an indicator.

Since the method according to the present invention is capable of predicting the antitumor effect of angiogenesis inhibitors without administering those inhibitors to patients, it is possible to select and treat those patients who are expected to show higher antitumor effect. Thus, it has become possible to contribute to patients' QOL.

Further, according to the present invention, a pharmaceutical composition and/or a kit comprising a combination of a VEGF receptor kinase inhibitor and an EGF inhibitor, and a method of treating cancers are provided. It has become possible to use such a pharmaceutical composition and/or a kit in cancer treatment.

BRIEF DESCRIPTION OF DRAWINGS

In FIG. 2, compound A represents 4-(3-chloro-4-(cyclopropylaminocarbonyl)aminophenoxy)-7-methoxy-6-quinolinecarboxamide and compound B represents erlotinib.

In FIG. 3, compound A represents 4-(3-chloro-4-(cyclopropylaminocarbonyl)aminophenoxy)-7-methoxy-6-quinolinecarboxamide and compound B represents erlotinib.

In FIG. 4, compound A represents 4-(3-chloro-4-(cyclopropylaminocarbonyl)aminophenoxy)-7-methoxy-6-quinolinecarboxamide and compound B represents erlotinib.

In FIG. 5, compound A represents 4-(3-chloro-4-(cyclopropylaminocarbonyl)aminophenoxy)-7-methoxy-6-quinolinecarboxamide and compound B represents erlotinib.

BEST MODE FOR CARRYING OUT THE INVENTION

Figure 1:
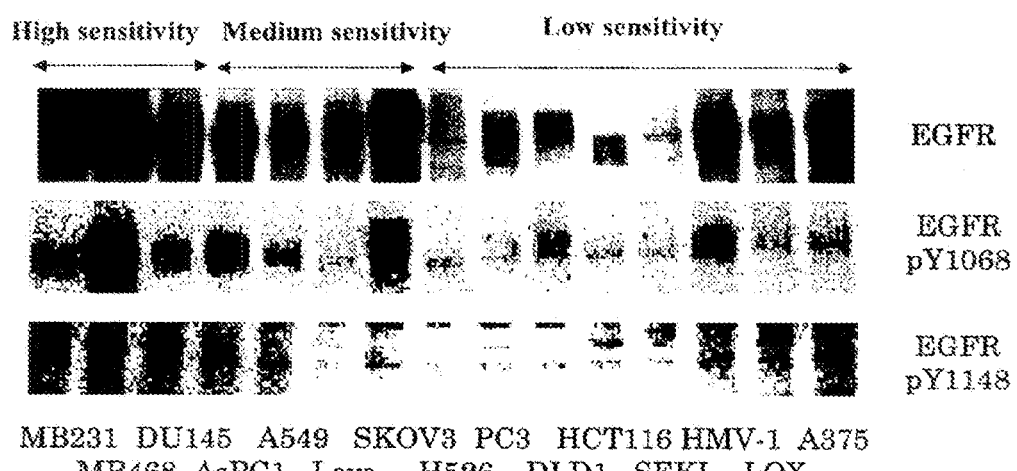
FIG. 1 shows the relations between the antitumor effect of 4-(3-chloro-4-(cyclopropylaminocarbonyl)aminocarbonyl) aminophenoxy)-7-methoxy-6-quinolinecarboxamide in human cancer cell line subcutaneous xenograft models and the degree of phosphorylation of EGF receptor in tumor tissues.

Hereinbelow, embodiments of the present invention will be described. The following embodiments are provided for the purpose of illustration only and should not be construed as limiting the present invention to those embodiments. The present invention may be practiced in various ways without departure of the gist of the present invention.

All publications, patent publications, patents and other patent documents cited herein are incorporated herein by reference in their entirety.

The present specification encompasses the contents of the specifications of Japanese Patent Applications Nos. 2005-224173 and 2006-164700 based on which the present patent application claims priority.

The present invention provides a method of predicting the antitumor effect of angiogenesis inhibitors, comprising a step of evaluating the EGF dependency of a tumor cell for proliferation and/or survival and a step of judging whether or not a cancer patient is highly sensitive to angiogenesis inhibitors by using the evaluated EGF dependency for proliferation and/or survival as an indicator.

The present invention also provides a novel pharmaceutical composition comprising a VEGF receptor kinase inhibitor in combination with an EGF inhibitor, a kit comprising the composition, and a method of treating cancers.

1. A Step of Evaluating the EGF Dependency of Tumor Cell for Proliferation and/or Survival In the present step, the tumor cell is preferably tumor cells taken from a cancer patient. The tumor cells from a cancer patient may be obtained by removing a tumor sample by surgical treatment (e.g., biopsy).

The size of tumor sample to be removed from a cancer patient is not particularly limited. Any size may be used as long as the tumor sample is capable of determination of the EGF dependency of the tumor cell for proliferation and/or survival. For example, if the tumor is a solid cancer, the size of tumor sample to be removed may be a size of a tumor sample taken by biopsy (e.g., 2-3 mm) or a size of a tissue section removed with a surgical knife (e.g., the size of grain of rice).

The type of tumor used in the present invention is not particularly limited. For example, brain tumor, head&neck cancer, esophageal cancer, tongue cancer, lung cancer, breast cancer, pancreatic cancer, gastric cancer, cancer of the small intestine or duodenum, large bowel cancer (colon cancer, rectal cancer), bladder cancer, renal cancer, liver cancer, prostate cancer, uterine cancer, ovary cancer, thyroid cancer, gallbladder cancer, pharyngeal cancer, sarcoma (e.g., osteosarcoma, chondrosarcoma, Kaposi sarcoma, myosarcoma, angiosarcoma, fibrosarcoma or the like), leukemia (e.g., chronic myelogenous leukemia (CML), acute myelogenous leukemia (AML), chronic lymphocytic leukemia (CLL), acute lymphocytic leukemia (ALL), lymphoma, malignant lymphoma, multiple myeloma (MM) or the like), melanoma and so forth may be enumerated.

The EGF dependency of a tumor cell for proliferation and/or survival means the apoptosis inducing ability of the tumor cell which is caused by depletion of signals concerning proliferation and/or survival delivered by EGF and the like. In other words, EGF dependency means that the tumor cell can not survive without EGF. The survival of normal epithelial cells largely depends on adhesion-mediated survival signaling, and these cells have a mechanism of causing apoptosis induction when they have perceived depletion of survival signaling. On the other hand, a part of those cells which have already lost dependency on adhesion (such as immortalized cells and tumor cells) is known to cause apoptosis induction when perceived depletion of growth factor (such as EGF) signaling instead of adhesion signaling, via a mechanism similar to that seen in normal cells (J. Biol. Chem. Vol. 279, No. 40, pp. 41280-41285, 2004). In some types of cell lines in which EGF receptors are activated in a ligand dependent manner, apoptosis induction by promoting EGF signal depletion (e.g., removal of ligands or treatment with EGF signal inhibitors) is reported (Oncogene. 2003 May 8; 22(18):2812-22). Briefly, the mechanism of apoptosis induction is the same in both normal cells and tumor cells, but the cause of apoptosis induction is depletion of adhesion signaling in normal cells, whereas the cause is depletion of EGF signaling in tumor cells.

EGF signaling is activated by biological substances that stimulate EGF signaling, e.g. EGF, heparin-binding EGF like growth factor (hereinafter, sometimes abbreviated to "HB-EGF"), transforming growth factor-α (hereinafter, sometimes abbreviated to "TGF-α", epiregulin (β-cellulin, amphiregulin (Nature Reviews Molecular Cell Biology 2, pp. 127-137, 2001)), etc. It is believed that the expression levels of EGF, HB-EGF, TGF-α, epiregulin and the like are increased in organisms which have tumor cells with high EGF dependency. Therefore, it is possible to evaluate the EGF dependency of tumor cells for proliferation and/or survival by using the expression levels of EGF, HB-EGF, TGF-α, epiregulin and the like as indicators. Not only the expression levels of EGF, HB-EGF, TGF-α and epiregulin in minor cells but also their expression levels in biological fluids (such as blood, spinal fluid, infiltrate, urine, saliva, lymph or celomic fluid) may be used as indicators. The expression levels of these substances in tumor cells or biological fluids may serve as indicators for evaluating the EGF dependency of each tumor cell for proliferation and/or survival.

The expression levels of EGF, HB-EGF, TGF-α and epiregulin may be analyzed by measuring the proteins and/or mRNAs of EGF, HB-EGF, TGF-α and epiregulin.

Further, the EGF dependency of tumor cells for proliferation and/or survival may be evaluated, for example, by using the expression level of EGF receptor (Proc Am Assoc Cancer Res 2002; 43:A3901) in the tumor cells. The expression level of EGF receptor may be analyzed by measuring the protein and/or mRNA of EGF receptor.

Measurement of proteins may be performed by known methods, e.g., immunochemical methods (such as ELISA, EIA, RIA, immunohistochemical methods, Western blotting, or flowcytometry), methods by mass spectrometric analysis, or the like. Preferably, immunochemical methods may be used. Among all, ELISA is particularly preferable. These methods may be performed according to conventional procedures.

Measurement of mRNAs may be performed by known methods. For example, in situ hybridization, Northern blotting, DNA microarray, RT-PCR, quantitative RT-PCR and the like may be enumerated. Preferably, quantitative RT-PCR may be used. These methods may be performed according to conventional procedures.

The expression level or the degree of phosphorylation of EGF receptor in tumor cells indicates the EGF dependency of individual tumor cells for proliferation and/or survival. Therefore, the EGF dependency of a tumor cell for proliferation and/or survival may be evaluated by using, for example, the degree of phosphorylation of the EGF receptor expressed in the tumor cell as an indicator.

Measurement of the phosphorylation of EGF receptor may be performed by known methods. For example, immunochemical methods (such as immunohistochemical methods or Western blotting), methods by mass spectrometric analysis, or the like. Preferably, immunochemical methods may be used. Among all, Western blotting is particularly preferable. These methods may be performed according to conventional procedures.

Hereinbelow, one example of a method for measuring the degree of phosphorylation of EGF receptor expressed in tumor cells will be described.

The degree of phosphorylation of EGF receptor expressed in tumor cells may be measured by immunoprecipitation and Western blotting.

Immunoprecipitation and Western blotting may be performed according to conventional procedures (Special Issue of Cell Engineering, Visual Experimental Note Series, Illustrated Biological Experiments, Vol. 5 "Who's Afraid of Proteins", Chapter 1, SDS-PAGE pp. 13-62, Chapter 4, Western Blotting pp. 105-126, Chapter 7, Immunoprecipitation pp. 171-182, published by Shujunsha Co., Ltd., 1997).

First, a cell lysate is prepared from tumor cells collected from a patient. A tumor cell lysate may be prepared by conventional procedures. Briefly, a tumor cell lysate may be obtained by adding to the tumor cells a cell lysis solution containing various protease inhibitors (Leupeptin, p-APMSF, EDTA and o-NaVO4) and 10% glycerol.

Then, immunoprecipitation may be performed on the resultant tumor cell lysate.

In one example, the tumor cell lysate is contacted with anti-EGF receptor antibody, anti-phosphorylation antibody or the like and incubated for a specific period of time. Subsequently, protein A-adsorbed agarose beads, protein A-adsorbed Sepharose beads or the like are added to the tumor cell lysate, which is incubated again for a specific period of time. Subsequently, the tumor cell lysate to which a carrier (to be bound to the antibody) was added is subjected to centrifugation or the like according to conventional procedures to thereby separate the antibody-binding carrier. Various conditions of reactions (such as reaction solution, antibody concentration, reaction time, reaction temperature, washing procedure, etc.) may be appropriately selected depending on the protein to be measured and the antibody to be used.

Subsequently, a sample obtained from immunoprecipitation may be subjected to Western blotting.

In one example, first, a buffer such as SDS sample buffer is added to the sample obtained from immunoprecipitation to thereby separate the sample from the immunoprecipitated carrier. Then, the resultant sample is electrophoresed by conventional procedures. Examples of electrophoresis include sodium dodecyl sulfate-polyacrylamide gel electrophoresis (SDS-PAGE), non-reduced SDS-PAGE, native-PAGE, isoelectric focusing and two-dimensional electrophoresis. Preferably, SDS-PAGE is used. After electrophoresis, the sample is transferred onto a membrane by conventional procedures. As the membrane, nitrocellulose membrane, nylon membrane, PVDF membrane or the like may be used. Preferably, nitrocellulose membrane is used.

The membrane is pretreated with a solution containing BSA, Triton-X100, tween 20, skim milk, casein or the like. The method of pretreatment is not particularly limited and may be appropriately selected depending on the protein to be measured and the antibody to be used.

Subsequently, the pretreated membrane is contacted with an antibody such as anti-EGF receptor antibody, anti-phosphorylation EGF receptor antibody, anti-phosphorylation antibody or the like (hereinafter, sometimes referred to as the "primary antibody"). When anti-EGF receptor antibody is used in immunoprecipitation, the primary antibody may be, for example, anti-phosphorylation EGF receptor antibody, anti-phosphorylation antibody or anti-phosphorylation tyrosine antibody. Preferably, anti-phosphorylation tyrosine antibody is used. When anti-phosphorylation antibody is used in immunoprecipitation, the primary antibody may be, for example, anti-phosphorylation EGF receptor antibody or anti-EGF receptor antibody. Preferably, anti-phosphorylation EGF receptor antibody is used. The primary antibody may be a commercially available antibody. Alternatively, the primary antibody may be prepared. The primary antibody may be labeled with a labeling agent or may not be labeled. When the primary antibody is not labeled, an antibody that recognizes the primary antibody (hereinafter, sometimes referred to as the "secondary antibody") may be contacted therewith.

The secondary antibody is preferably labeled with a labeling agent. Examples of the labeling agent include enzymes (such as alkaline phosphatase, peroxidase, glucose oxidase, β-galactosidase), fluorescent substances (such as FITC (fluorescein isothiocyanate), Alexa488, PE, Rhodamin, Texas Red, Cy3, Cy5, allophycocyanin, PharRed, DsRed, AmCyan, ZsGreen, ZsYellow, AsRed, HcRed) and biotin. When the labeling agent is biotin, avidin or streptavidin may be contacted further. Such avidin or streptavidin is preferably labeled with a labeling agent. Examples of the labeling agent include enzymes (such as alkaline phosphatase, peroxidase, glucose oxidase, β-galactosidase) and fluorescent substances (such as FITC, Alexa488, PE, Rhodamin, Texas Red, Cy3, Cy5, allophycocyanin, PharRed, DsRed, AmCyan, ZsGreen, ZsYellow, AsRed, HcRed). Various conditions of reactions (such as reaction solution, antibody concentration, reaction time, reaction temperature, washing procedure, etc.) may be appropriately selected depending on the protein to be measured and the antibody to be used.

When the labeling agent is an enzyme, a substrate and/or a coloring reagent is contacted with the membrane for coloring. By observing this coloring, it is possible to measure the phosphorylation of EGF receptor.

When the enzyme is peroxidase, a substrate such as $H_2O_2$ and a coloring reagent such as diaminobenzidine (DAB) may be contacted with the membrane. When the enzyme is peroxidase, it is also possible to perform a chemiluminescence reaction by contacting a substrate such as $H_2O_2$ and a coloring reagent such as luminol with the membrane.

When the enzyme is alkaline phosphatase, a substrate such as 5-bromo-4-chloro-3-indolyl phosphate and a coloring reagent such as nitrobluetetrazorium may be contacted with the membrane. When the enzyme is alkaline phosphatase, it is also possible to perform a chemiluminescent reaction by contacting a coloring substrate such as CSPD (disodium 3-(4-methoxyspiro {1,2-dioxetane-3,2'-(5'-chloro)tricyclo [$3.3.1.1^{3,7}$]-decan}-4-yl)phenylphosphate) with the membrane.

For detection, x-ray films may be used. Image analyzers which detect luminescence with a CCD camera may also be used.

When the labeling agent is a fluorescent substance, the phosphorylation of EGF receptor may be measured by irradiating the membrane with excitation light for luminescence and observing the resultant fluorescence.

Thus, it is possible to measure the phosphorylation of the EGF receptor expressed in tumor cells.

Hereinbelow, one example of another method for measuring the phosphorylation of the EGF receptor expressed in tumor cells will be described.

The phosphorylation of EGF receptor in tumor cells may be measured by an immunohistochemical method using anti-phosphorylation antibody.

The immunohistochemical method may be performed according to conventional procedures (Special Issue of Cell Engineering, Visual Experimental Note Series, Illustrated Biological Experiments, Vol. 5 "Who's Afraid of Proteins", Chapter 5, Immunostaining pp. 127-163, published by Shujunsha Co., Ltd., 1997).

First, tissue sections are prepared from tumor samples taken from patients. Examples of tissue sections include frozen sections and paraffin sections.

Tumor samples taken from patients may be either untreated or treated for fixation. The tumor samples may be embedded with OCT compound or the like.

Fixation treatment may be performed with formaldehyde, preferably 4% PFA/PBS(−). Then, the formaldehyde may be replaced with 20% sucrose/phosphate buffer or the like.

Various conditions for these operations may be selected appropriately depending on the protein to be measured and the antibody to be used.

The tissue section may be retained on a slide glass and pretreated to make staining possible. The method of this pretreatment is not particularly limited and may be appropriately selected depending on the protein to be measured and the antibody to be used. For example, the tissue section may be pretreated with a solution containing xylene, formaldehyde, acetone, methanol, etc. Alternatively, the tissue section may be pretreated with a solution containing BSA, Triton-X100, tween 20, skim milk, casein, etc.

Subsequently, anti-phosphorylation EGF receptor antibody (hereinafter, sometimes referred to as the "primary antibody") is contacted with the pretreated tissue section. The primary antibody may be a commercially available antibody or may be prepared. The primary antibody may be labeled with a labeling agent or may not be labeled. When the primary antibody is not labeled, an antibody that recognizes the primary antibody (hereinafter, sometimes referred to as the "secondary antibody") may be contacted therewith. The secondary antibody is preferably labeled with a labeling agent. Examples of the labeling agent include enzymes (such as alkaline phosphatase, peroxidase, glucose oxidase. β-galactosidase), fluorescent substances (such as FITC (fluorescein isothiocyanate), Alexa488, PE, Rhodamin, Texas Red, Cy3, Cy5, allophycocyanin, PharRed, DsRed, AmCyan, ZsGreen, ZsYellow, AsRed, HcRed) and biotin. When the labeling agent is biotin, avidin or streptavidin may be contacted further. Such avidin or streptavidin is preferably labeled with a labeling agent. Examples of the labeling agent include enzymes (such as alkaline phosphatase, peroxidase, glucose oxidase, β-galactosidase) and fluorescent substances (such as FITC, Alexa488, PE, Rhodamin, Texas Red, Cy3, Cy5, allophycocyanin, PharRed, DsRed, AmCyan, ZsGreen, ZsYellow, AsRed, HcRed). Various conditions of reactions (such as reaction solution, antibody concentration, reaction time, reaction temperature, washing procedure, etc.) may be appropriately selected depending on the protein to be measured and the antibody to be used.

When the labeling agent is an enzyme, a substrate and/or a coloring reagent is contacted with the tissue section for coloring. By observing this coloring, it is possible to measure the phosphorylation of EGF receptor expressed in tumor cells.

When the enzyme is peroxidase, a substrate such as $H_2O_2$ and a coloring reagent such as diaminobenzidine (DAB) may be contacted with the tissue section.

When the enzyme is alkaline phosphatase, a substrate such as 5-bromo-4-chloro-3-indolyl phosphate and a coloring reagent such as nitrobluetetrazorium may be contacted with the tissue section. When the enzyme is alkaline phosphatase, it is also possible to perform a chemiluminescent reaction by contacting a coloring substrate such as CSPD (disodium 3-(4- methoxyspiro {1,2-dioxetane-3,2'-(5'-chloro)tricyclo [3.3.1.1$^{3,7}$]-decan}-4-yl)phenylphosphate) with the tissue section.

When the labeling agent is a fluorescent substance, the phosphorylation of EGF receptor may be measured by irradiating the tissue section with excitation light for luminescence and observing the resultant fluorescence.

Thus, it is possible to measure the phosphorylation of the EGF receptor expressed in tumor cells.

Further, the pretreated tissue section may be nuclear stained with hematoxylin or methyl green.

Further, the pretreated tissue section may be mounted with an aqueous mounting medium.

Further, it is possible to evaluate the EGF dependency of tumor cells for proliferation and/or survival by using, as an indicator, the proliferation and/or survival of tumor cells induced by EGF. Methods for measuring the proliferation and/or survival of tumor cells induced by EGF include cell proliferation assay and survival assay. Cell proliferation assay includes, for example, by the tritium-thymidine uptake method, the MTT method, the XTT method (Cell Counting Kit-8; Dojindo Co.), the Alamar Blue method, the neutral red method, the BrdU method, the Ki67 staining method and the PCNA staining method. Preferably, the PCNA staining method is used. Survival assay includes, for example, the TUNNEL staining method, the Caspase-3 cleavage detection method and the PARP cleavage detection method. Preferably, the Caspase-3 cleavage detection method is used. These methods may be performed according to conventional procedures.

2. A Step of Judging Whether or not Cancer Patients are Highly Sensitive to Angiogenesis Inhibitors In this step, whether or not cancer patients are highly sensitive to angiogenesis inhibitors is judged by using, as an indicator, the EGF dependency of a tumor cell for proliferation and/or survival. The EGF dependency of a tumor cell for proliferation and/or survival may be evaluated by using, as an indicator, the results of measuring the protein and/or mRNA of EGF receptor expressed in the tumor cell, the phosphorylation of EGF receptor expressed in the tumor cell, the proliferation and/or survival of the tumor cell induced by EGF, and the like. When the EGF dependency of the tumor cell for proliferation and/or survival is high, it is judged that the cancer patient is highly sensitive to angiogenesis inhibitors.

Examples of cases where the EGF dependency of tumor cells for proliferation and/or survival are high include those cases where a significant amount of EGF receptor is expressed in tumor cells (e.g., EGF receptor expression is positive); those cases where EGF receptor is phosphorylate; and those cases where EGF, HB-EGF, TGF-α, epiregulin, etc. are expressed highly. The case where EGF, HB-EGF, TGF-α, epiregulin, etc. are expressed highly refers to, for example, a case where the expression levels of EGF, HB-EGF, TGF-α, epiregulin, etc. in a target tumor cell are 1.5-fold or more, preferably 2-fold or more, more preferably 3-fold or more, still preferably 4-fold or more, compared to the corresponding expression levels in normal cells (non-tumor cells) or average tumor cells. The case where EGF, HB-EGF, TGF-α, epiregulin, etc. are expressed highly also refers to a case, for example, where the expression levels of EGF, HB-EGF, TGF-α, epiregulin, etc. in body fluids of a patient of interest are 1.5-fold or more, preferably 2-fold or more, more preferably 3-fold or more, still preferably 4-fold or more, compared to the corresponding expression levels in body fluids of normal persons or average patients.

As another embodiment of the present invention, a method is provided in which patients who will show high sensitivity to angiogenesis inhibitors are selected by using the EGF dependency of a target tumor cell for proliferation and/or survival as an indicator. From the results of evaluation of EGF dependency, it is possible to judge that when the EGF dependency of a target tumor cell for proliferation and/or survival is high, patients having that tumor cell will show high sensitivity to angiogenesis inhibitors, as described above. Therefore, these patients may be selected as patients who will show high sensitivity to angiogenesis inhibitors.

As another embodiment of the present invention, a method is provided in which patients to be administered angiogenesis inhibitors are selected by using the EGF dependency of a target tumor cell for proliferation and/or survival as an indicator. Those patients with high EGF dependency of the tumor cell for proliferation and/or survival are selected as patients to be administered angiogenesis inhibitors.

As another embodiment of the present invention, a method is provided in which the therapeutic effects of angiogenesis inhibitors in patients are predicted by using the EGF dependency of a target tumor cell for proliferation and/or survival as an indicator. In the method of the present invention, since it is possible to judge that patients having a target tumor cell will show high sensitivity to angiogenesis inhibitors when the EGF dependency of the target tumor cell was found high upon evaluation of EGF dependency, the therapeutic effects of angiogenesis inhibitors on the tumor cell or patients with the tumor cell can be predicted high.

Further, the present invention encompasses a method of evaluating the EGF dependency of a patient-derived tumor cell for proliferation and/or survival, in order to predict the degree of sensitivity of the patient to angiogenesis inhibitors. The evaluation method is as described in item 1 above.

In the present step, the angiogenesis inhibitor is as described previously. Preferably, the angiogenesis inhibitor is 4-(3-chloro-4-(cyclopropylaminocarbonyl)aminophenoxy)-7-methoxy-6-quinolinecarboxamide, a pharmacologically acceptable salt thereof, or a solvate of the compound or the salt.

The methods according to the present invention may be used prior to administration of angiogenesis inhibitors to patients in order to predict the degree of efficacy of angiogenesis inhibitors in patients. Then, those patients in whom larger effect of angiogenesis inhibitors can be expected may be selected and treated. Therefore, the present invention is clinically very useful.

3. Angiogenesis Inhibitors

In the present invention, angiogenesis inhibitors are not particularly limited. Any substance may be used as long as it has inhibitory activity against angiogenesis.

Examples of angiogenesis inhibitors include:

VEGF inhibitors (e.g., VEGF receptor kinase inhibitor, anti-VEGF receptor antibody, anti-VEGF antibody (Cancer Research, 55, 5296-5301, 1995));

FGF (fibroblast growth factor) inhibitors (e.g., FGF receptor kinase inhibitor, anti-FGF receptor antibody, anti-FGF antibody (Cancer Research, 51, 6180-4, 1991));

PDGF (platelet-derived growth factor) inhibitors (e.g., PDGF receptor kinase inhibitor (J. Clinical Investigation, 111, 1287-95), anti-PDGF receptor antibody, anti-PDGF antibody);

EGF (epidermal growth factor) inhibitors (e.g., EGF receptor kinase inhibitor (Cancer Research, 51, 6180-4, 1991), anti-FGF receptor antibody, anti-EGF antibody);

Integrin inhibitors (e.g., αvβ3 integrin inhibitor, αvβ5 integrin inhibitor (Clinical Cancer Research, 6, 3056-61, 2000));

Endogenous inhibitors (e.g., IL-12, trombospondin-1, endostatin, angiostatin (International J. Cancer., 78, 361-5, 1998), COX-2 inhibitor (Annuals of N.Y. Acad. Science., 84-6, 1999));

Matrix metalloprotein inhibitors (International J. Pancreatol., 21, 1-12, 1997);

Other inhibitors (e.g., farnesyltransferase inhibitor, nitric oxide inhibitor, antiotensin-converting enzyme inhibitor, HMG-CoA reductase inhibitor, vascular target inhibitor, methionine aminopeptidase inhibitor (Science, 282, 1324-1327, 1998)); and so on.

Among all, VEGF inhibitors are preferable. More preferable is VEGF receptor kinase inhibitor, anti-VEGF receptor antibody or anti-VEGF antibody. Particularly preferable is VEGF receptor kinase inhibitor.

(A) Definitions of Groups in Compounds

The term "halogen atom" used in the present specification means fluorine atom, chlorine atom, bromine atom or iodine atom.

Preferable examples of "halogen atom" are fluorine atom and chlorine atom.

The term "$C_{1-6}$ alkyl group" used in the present specification means a straight-chain or branched-chain alkyl group with 1 to 6 carbon atoms. Specific examples include methyl group, ethyl group, 1-propyl group (n-propyl group), 2-propyl group (i-propyl group), 2-methyl-1-propyl group (i-butyl group), 2-methyl-2-propyl group (t-butyl group), 1-butyl group (n-butyl group), 2-butyl group (s(sec)-butyl group), 1-pentyl group, 2-pentyl group, 3-pentyl group, 2-methyl-1-butyl group, 3-methyl-1-butyl group, 2-methyl-2-butyl group, 3-methyl-2-butyl group, 2,2-dimethyl-1-propyl group, 1-hexyl group, 2-hexyl group, 3-hexyl group, 2-methyl-1-pentyl group, 3-methyl-1-pentyl group, 4-methyl-1-pentyl group, 2-methyl-2-pentyl group, 3-methyl-2-pentyl group, 4-methyl-2-pentyl group, 2-methyl-3-pentyl group, 3-methyl-3-pentyl group, 2,3-dimethyl-1-butyl group, 3,3-dimethyl-1-butyl group, 2,2-dimethyl-1-butyl group, 2-ethyl-1-butyl group, 3,3-dimethyl-2-butyl group, 2,3-dimethyl-2-butyl group, or the like.

As preferable examples of "$C_{1-6}$ alkyl group", methyl group, ethyl group, 1-propyl group, 2-propyl group, 2-methyl-1-propyl group, 2-methyl-2-propyl group, 1-butyl group, 2-butyl group, 1-pentyl group, 2-pentyl group, 3-pentyl group, 2-methyl-1-butyl group, 3-methyl-1-butyl group, 2-methyl-2-butyl group, 3-methyl-2-butyl group and 2,2-dimethyl-1-propyl group may be enumerated. As more preferable examples, methyl group, ethyl group, 1-propyl group, 2-propyl group, 2-methyl-1-propyl group, 2-methyl-2-propyl group, 1-butyl group and 2-butyl group may be enumerated. As still more preferable examples, methyl group, ethyl group, 1-propyl group and 2-propyl group may be enumerated. As most preferable example, methyl group and ethyl group may be enumerated.

The term "$C_{1-6}$ alkylene group" used in the present specification means a divalent group which is derived from the above-defined "$C_{1-6}$ alkyl group" by removing any one hydrogen atom. Specific examples include methylene group, 1,2-ethylene group, 1,1-ethylene group, 1,3-propylene group, tetramethylene group, pentamethylene group, hexamethylene group, or the like.

The term "$C_{2-6}$ alkenyl group" used in the present specification means a straight-chain or branched-chain alkenyl group with 2 to 6 carbon atoms, having one double bond. Specific examples include ethenyl group (vinyl group), 1-propenyl group, 2-propenyl group (allyl group), 1-butenyl group, 2-butenyl group, 3-butenyl group, pentenyl group, hexenyl group or the like.

The term "$C_{2-6}$ alkynyl group" used in the present specification means a straight-chain or branched-chain alkynyl group with 2 to 6 carbon atoms, having one triple bond. Specific examples include ethynyl group, 1-propynyl group, 2-propynyl group, 1-butynyl group, 2-butynyl group, 3-butynyl group, pentynyl group, hexynyl group or the like.

The term "$C_{3-8}$ cycloalkyl group" used in the present specification means a monocyclic or bicyclic saturated aliphatic hydrocarbon group with 3 to 8 carbon atoms. Specific examples include cyclopropyl group, cyclobutyl group, cyclopentyl group, cyclohexyl group, cycloheptyl group, cyclooctyl group, bicyclo[2.1.0]pentyl group, bicyclo[3.1.0]hexyl group, bicyclo[2.1.1]hexyl group, bicyclo[4.1.0]heptyl group, bicyclo[2.2.1]heptyl group (norbornyl group), bicyclo[3.3.0]octyl group, bicyclo[3.2.1]octyl group, bicyclo[2.2.2]octyl group, or the like.

As preferable examples of "$C_{3-8}$ cycloalkyl group", cyclopropyl group, cyclobutyl group and cyclopentyl group may be enumerated. As a more preferable example, cyclopropyl group may be given.

The term "$C_{6-10}$ aryl group" used in the present specification means an aromatic hydrocarbon cyclic group with 6 to 10 carbon atoms. Specific examples include phenyl group, 1-naphthyl group, 2-naphthyl group, indenyl group, azulenyl group, or the like.

As a preferable example of "$C_{6-10}$ aryl group", phenyl group may be given.

The term "heteroatom" used in the present specification means nitrogen atom, oxygen atom or sulfur atom.

The term "5- to 10-membered heteroaryl group" used in the present specification means an aromatic cyclic group in which the ring is composed of 5 to 10 atoms comprising 1 to 5 heteroatoms. Specific examples include furyl group, thienyl group, pyrrolyl group, imidazolyl group, triazolyl group, tetrazolyl group, thiazolyl group, pyrazolyl group, oxazolyl group, isooxazolyl group, isothiazolyl group, furazanyl group, thiadiazolyl group, oxadiazolyl group, pyridyl group, pyrazinyl group, pyridazinyl group, pyrimidinyl group, triazinyl group, purinyl group, pteridinyl group, quinolyl group, isoquinolyl group, naphthyridinyl group, quinoxalinyl group, cinnolinyl group, quinazolinyl group, phthalazinyl group, imidazopyridyl group, imidazothiazolyl group, imidazooxazolyl group, benzothiazolyl group, benzoxazolyl group, benzimidazolyl group, indolyl group, isoindolyl group, indazolyl group, pyrrolopyridyl group, thienopyridyl group, furopyridyl group, benzothiadiazolyl group, benzoxadiazolyl group, pyridopyrimidinyl group, benzofuryl group, benzothienyl group, thienofuryl group, or the like.

As preferable examples of "5- to 10-membered heteroaryl group", furyl group, thienyl group, pyrrolyl group, imidazolyl group, thiazolyl group, pyrazolyl group, oxazolyl group, isooxazolyl group, isothiazolyl group, pyridyl group and pyrimidinyl group may be enumerated.

The term "3- to 10-membered non-aromatic heterocyclic group" used in the present specification is defined as follows:
(1) the ring thereof is composed of 3 to 10 atoms;
(2) 1 to 2 heteroatoms are included in those atoms;
(3) the ring may contain 1 to 2 double bonds;
(4) the ring may contain 1 to 3 carbonyl groups, sulfinyl groups or sulfonyl groups;
(5) the term means a monocyclic or heterocyclic, non-aromatic cyclic group; and when the atoms constituting its ring contain nitrogen atom(s), the nitrogen atom(s) may have a bond extended therefrom.

Specific examples of "3- to 10-membered non-aromatic heterocyclic group" include aziridinyl group, azetidinyl group, pyrrolidinyl group, piperidinyl group, azepanyl group, azocanyl group, piperadinyl group, diazepanyl group, diazocanyl group, diazabicyclo[2.2.1]heptyl group, morpholinyl group, thiomorpholinyl group, 1,1-dioxothiomorpholinyl group, oxiranyl group, oxetanyl group, tetrahydrofuryl group, dioxoranyl group, tetrahydropyranyl group, dioxanyl group, tetrahydrothienyl group, tetrahydrothiopyranyl group, oxazolidinyl group, thiazolidinyl group or the like.

As preferable examples of "3- to 10-membered non-aromatic heterocyclic group", aziridinyl group, azetidinyl group, pyrrolidinyl group, piperidinyl group, azepanyl group, piperadinyl group, diazepanyl group, morpholinyl group, thiomorpholinyl group, 1,1-dioxothiomorpholinyl group, tetrahydrofuryl group and tetrahydropyranyl group may be enumerated.

The term "$C_{1-6}$ alkoxy group" used in the present specification means the above-defined "$C_{1-6}$ alkyl group" to which an oxygen atom is attached at one end. Specific examples include methoxy group, ethoxy group, 1-propoxy group (n-propoxy group), 2-propoxy group (i-propoxy group), 2-methyl-1-propoxy group (i-butoxy group), 2-methyl-2-propoxy group (t-butoxy group), 1-butoxy group (n-butoxy group), 2-butoxy group (s-butoxy group), 1-pentyloxy group, 2-pentyloxy group, 3-pentyloxy group, 2-methyl-1-butoxy group, 3-methyl-1-butoxy group, 2-methyl-2-butoxy group, 3-methyl-2-butoxy group, 2,2-dimethyl-1-propoxy group, 1-hexyloxy group, 2-hexyloxy group, 3-hexyloxy group, 2-methyl-1-pentyloxy group, 3-methyl-1-pentyloxy group, 4-methyl-1-pentyloxy group, 2-methyl-2-pentyloxy group, 3-methyl-2-pentyloxy group, 4-methyl-2-pentyloxy group, 2-methyl-3-pentyloxy group, 3-methyl-3-pentyloxy group, 2,3-dimethyl-1-butoxy group, 3,3-dimethyl-1-butoxy group, 2,2-dim ethyl-1-butoxy group, 2-ethyl-1-butoxy group, 3,3-dimethyl-2-butoxy group, 2,3-dimethyl-2-butoxy group, or the like.

As preferable examples of "$C_{1-6}$ alkoxy group", methoxy group, ethoxy group, 1-propoxy group, 2-propoxy group, 2-methyl-1-propoxy group, 2-methyl-2-propoxy group, 1-butoxy group, 2-butoxy group, 1-pentyloxy group, 2-pentyloxy group, 3-pentyloxy group, 2-methyl-1-butoxy group, 3-methyl-1-butoxy group, 2-methyl-2-butoxy group, 3-methyl-2-butoxy group and 2,2-dimethyl-1-propoxy group may be enumerated. As more preferable examples, methoxy group, ethoxy group, 1-propoxy group, 2-propoxy group, 2-methyl-1-propoxy group, 2-methyl-2-propoxy group, 1-butoxy group and 2-butoxy group, may be enumerated. As still more preferable examples, methoxy group, ethoxy group, 1-propoxy group and 2-propoxy group may be enumerated. As most preferable examples, methoxy group and ethoxy group may be enumerated.

The term "$C_{1-6}$ alkylthio group" used in the present specification means the above-defined "$C_{1-6}$ alkyl group" to which a sulfur atom is attached to at one end. Specific examples include methylthio group, ethylthio group, 1-propylthio group (n-propylthio group), 2-propylthio group (i-propylthio group), 2-methyl-1-propylthio group (i-butylthio group), 2-methyl-2-propylthio group (t-butylthio group), 1-butylthio group (n-butylthio group), 2-butylthio group (s-butylthio group), 1-pentylthio group, 2-pentylthio group, 3-pentylthio group, 2-methyl-1-butylthio group, 3-methyl-1-butylthio group, 2-methyl-2-butylthio group, 3-methyl-2-butylthio group, 2,2-dimethyl-1-propylthio group, 1-hexylthio group, 2-hexylthio group, 3-hexylthio group, 2-methyl-1-pentylthio group, 3-methyl-1-pentylthio group, 4-methyl-1-pentylthio group, 2-methyl-2-pentylthio group, 3-methyl-2-pentylthio group, 4-methyl-2-pentylthio group, 2-methyl-3-pentylthio group, 3-methyl-3-pentylthio group, 2,3-dimethyl-1-butylthio group, 3,3-dimethyl-1-butylthio group, 2,2-dimethyl-1-butylthio group, 2-ethyl-1-butylthio group, 3,3-dimethyl-2-butylthio group, 2,3-dimethyl-2-butylthio group, or the like.

As preferable examples of "$C_{1-6}$ alkylthio group", methylthio group, ethylthio group, 1-propylthio group (n-propylthio group), 2-propylthio group (i-propylthio group), 2-methyl-1-propylthio group (i-butylthio group), 2-methyl-2-propylthio group (t-butylthio group), 1-butylthio group (n-butylthio group) and 2-butylthio group (s-butylthio group) may be enumerated.

The term "$C_{3-8}$ cycloalkoxy group" used in the present specification means the above-defined "$C_{3-8}$ cycloalkyl group" to which an oxygen atom is attached at one end. Specific examples include cyclopropoxy group, cyclobutoxy group, cyclopentyloxy group, cyclohexyloxy group, cycloheptyloxy group, cyclooctyloxy group, bicyclo[2.1.0]pentyloxy group, bicyclo[3.1.0]hexyloxy group, bicyclo[2.1.1]hexyloxy group, bicyclo[4.1.0]heptyloxy group, bicyclo[2.2.1]heptyloxy group (norbornyloxy group), bicyclo[3.3.0]octyloxy group, bicyclo[3.2.1]octyloxi group, bicyclo[2.2.2]octyloxy group, or the like.

As preferable examples of "$C_{3-8}$ cycloalkoxy group", cyclopropoxy group, cyclobutoxy group and cyclopentyloxy group may be enumerated. As a more preferable example, cyclopropoxy group may be given.

The term "mono-$C_{1-6}$ alkylamino group" used in the present specification means an amino group in which one hydrogen atom is replaced with the above-defined "$C_{1-6}$ alkyl group". Specific examples include methylamino group, ethylamino group, 1-propylamino group (n-propylamino group), 2-propylamino group (i-propylamino group), 2-methyl-1-propylamino group (i-butylamino group), 2-methyl-2-propylamino group (t-butylamino group), 1-butylamino group (n-butylamino group), 2-butylamino group (s-butylamino group), 1-pentylamino group, 2-pentylamino group, 3-pentylamino group, 2-methyl-1-butylamino group, 3-methyl-1-butylamino group, 2-methyl-2-butylamino group, 3-methyl-2-butylamino group, 2,2-dimethyl-1-propylamino group, 1-hexylamino group, 2-hexylamino group, 3-hexylamino group, 2-methyl-1-pentylamino group, 3-methyl-1-pentylamino group, 4-methyl-1-pentylamino group, 2-methyl-2-pentylamino group, 3-methyl-2-pentylamino group, 4-methyl-2-pentylamino group, 2-methyl-3-pentylamino group, 3-methyl-3-pentylamino group, 2,3-dimethyl-1-butylamino group, 3,3-dimethyl-1-butylamino group, 2,2-dimethyl-1-butylamino group, 2-ethyl-1-butylamino group, 3,3-dimethyl-2-butylamino group, 2,3-dimethyl-2-butylamino group, or the like.

The term "di-$C_{1-6}$ alkylamino group" used in the present specification means an amino group in which two hydrogen atoms are replaced with two of the above-defined "$C_{1-6}$ alkyl group", respectively. These two $C_{1-6}$ alkyl groups may be the same or different. Specific examples include N,N-dimethylamino group, N,N-diethylamino group, N,N-di-n-propylamino group, N,N-di-i-propylamino group, N,N-di-n-butylamino group, N,N-di-i-butylamino group, N,N-di-s-butylamino group, N,N-di-t-butylamino group, N-ethyl-N-methylamino group, N-n-propyl-N-methylamino group, N-i-propyl-N-methylamino group, N-n-butyl-N-methylamino group, N-i-butyl-N-methylamino group, N-s-butyl-N-methylamino group, N-t-butyl-N-methylamino group, or the like.

The term "$C_{2-7}$ acyl group" used in the present specification means a carbonyl group to which the above-defined "$C_{1-6}$ alkyl group" is attached. Specific examples include acetyl group, propionyl group, isopropionyl group, butylyl group, isobutylyl group, valeryl group, isovaleryl group, pivaloyl group, or the like.

The term "$C_{2-7}$ alkoxycarbonyl group" used in the present specification means a carbonyl group to which the above-defined "$C_{1-6}$ alkoxy group" is attached. Specific examples include methoxycarbonyl group, ethoxycarbonyl group, 1-propyloxycarbonyl group, 2-propyloxycarbonyl group, 2-methyl-2-propoxycarbonyl, or the like.

The expression "may have a substituent(s)" means "may have one or a plurality of substituents in any combination at a position(s) capable of substitution". Specific examples of substituents include halogen atoms, hydroxyl group, thiol group, nitro group, cyano group, formyl group, carboxyl group, amino group, silyl group, methanesulfonyl group, $C_{1-6}$ alkyl group, $C_{2-6}$ alkenyl group, $C_{2-6}$ alkynyl group, $C_{3-8}$ cycloalkyl group, $C_{6-10}$ aryl group, 5- to 10-membered heteroaryl group, 3- to 10-membered non-aromatic heterocyclic group, $C_{1-6}$ alkoxy group, $C_{1-6}$ alkylthio group, $C_{3-8}$ cycloalkoxy group, mono-$C_{1-6}$ alkylamino group, di-$C_{1-6}$ alkylamino group, $C_{2-7}$ acyl group, $C_{2-7}$ alkoxycarbonyl group or the like (provided that $C_{1-6}$ alkyl group, $C_{2-6}$ alkenyl group, $C_{2-4}$ alkynyl group, $C_{3-8}$ cycloalkyl group, $C_{6-10}$ aryl group, 5- to 10-membered heteroaryl group, 3- to 10-membered non-aromatic heterocyclic group, $C_{1-6}$ alkoxy group, $C_{1-6}$ alkylthio group, $C_{3-8}$ cycloalkoxy group, mono-$C_{1-6}$ alkylamino group, di-$C_{1-6}$ alkylamino group, $C_{2-7}$ acyl group and $C_{2-7}$ alkoxycarbonyl group independently of each other may have 1 to 3 groups selected from the group of substituents described below).

<Group of Substitutents>

Halogen atom, hydroxyl group, thiol group, nitro group, cyano group, $C_{1-6}$ alkyl group, $C_{3-8}$ cycloalkoxy group, $C_{2-6}$ alkenyl group, $C_{2-6}$ alkynyl group, $C_{6-10}$ aryl group, 5- to 10-membered heteroaryl group, 3- to 10-membered non-aromatic heterocyclic group, $C_{14}$ alkoxy group and $C_{1-6}$ alkylthio group.

(B) VEGF Receptor Kinase Inhibitors (B-1) General Formula (I)

In the present invention, the VEGF receptor kinase inhibitor may be, for example, a compound represented by the following general formula (I):

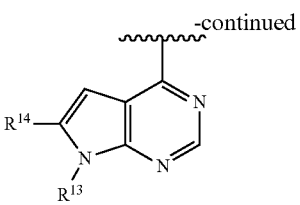
(I)

(i) A

A in general formula (I) is a group represented by one of the following formulas:

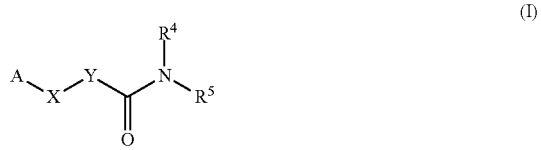

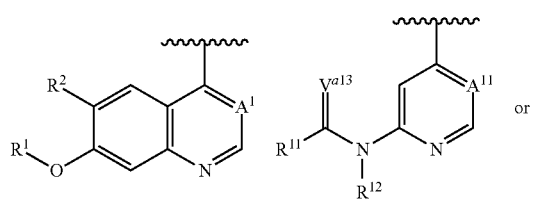

In the above formulas, $R^1$ is a group represented by a formula —$V^1$—$V^2$—$V^3$ (where $V^1$ is a $C_{1-6}$ alkylene group which may have a substituent(s); $V^2$ is a single bond, an oxygen atom, a sulfur atom, a carbonyl group, a sulfinyl group, a sulfonyl group, a group represented by a formula —CONR$^6$—, a group represented by a formula —SO$_2$NR$^6$—, a group represented by a formula —NR$^6$SO$_2$—, a group represented by a formula —NR$^6$CO— or a group represented by a formula —NR$^6$— (where $R^6$ is a hydrogen atom, a $C_{1-6}$ alkyl group which may have a substituent(s) or a $C_{3-8}$ cycloalkyl group which may have a substituent(s)); and $V^3$ is a hydrogen atom, a $C_{1-6}$ alkyl group which may have a substituent(s), a $C_{2-6}$ alkenyl group which may have a substituent(s), a $C_{2-6}$ alkynyl group which may have a substituent(s), a $C_{3-8}$ cycloalkyl group which may have a substituent(s); a $C_{6-10}$ aryl group which may have a substituent(s), a 5- to 10-membered heteroaryl group which may have a substituent(s) or a 3- to 10-membered non-aromatic heterocyclic group which may have a substituent(s)).

$R^2$ is a cyano group, a $C_{1-6}$ alkoxy group which may have a substituent(s), a carboxyl group, a $C_{2-7}$ alkoxycarbonyl group which may have a substituent(s) or a group represented by a formula —CONV$^{a11}$V$^{a12}$ (where V$^{a11}$ is a hydrogen atom, a $C_{1-6}$ alkyl group which may have a substituent(s), a $C_{2-6}$ alkenyl group which may have a substituent(s), a $C_{2-6}$ alkynyl group which may have a substituent(s), a $C_{3-8}$ cycloalkyl group which may have a substituent(s); a $C_{6-10}$ aryl group which may have a substituent(s), a 5- to 10-membered heteroaryl group which may have a substituent(s) or a 3- to 10-membered non-aromatic heterocyclic group which may have a substituent(s); and V$^{a12}$ is a hydrogen atom, a $C_{2-6}$ alkyl group which may have a substituent(s), a $C_{2-6}$ alkenyl group which may have a substituent(s), a $C_{2-6}$ alkynyl group which may have a substituent(s), a $C_{3-8}$ cycloalkyl group which may have a substituent(s); a $C_{6-10}$ aryl group which may have a substituent(s), a 5- to 10-membered heteroaryl group which may have a substituent(s), a 3- to 10-membered non-aromatic heterocyclic group which may have a substituent(s), a hydroxyl group, a $C_{1-6}$ alkoxy group which may have a substituent(s) or a $C_{3-8}$ cycloalkoxy group which may have a substituent(s)).

$A^1$ is a carbon atom which may have a substituent or a nitrogen atom.

$R^{11}$ is a hydrogen atom, a $C_{1-6}$ alkyl group which may have a substituent(s), a $C_{2-6}$ alkenyl group which may have a substituent(s), a $C_{2-6}$ alkynyl group which may have a substituent(s), a $C_{3-8}$ cycloalkyl group which may have a substituent(s); a $C_{6-10}$ aryl group which may have a substituent(s), a 5- to 10-membered heteroaryl group which may have a substituent(s), a 3- to 10-membered non-aromatic heterocyclic group which may have a substituent(s) or a mono-$C_{1-6}$ alkylamino group which may have a substituent(s).

$R^{12}$ is a hydrogen atom or a $C_{1-6}$ alkyl group which may have a substituent(s).

$V^{a13}$ is an oxygen atom or a sulfur atom.

$A^{11}$ is a carbon atom which may have a substituent or a nitrogen atom.

$R^{13}$ is a hydrogen atom, a $C_{1-6}$ alkyl group which may have a substituent(s) or a $C_{3-8}$ cycloalkyl group which may have a substituent(s).

$R^{14}$ is a group represented by a formula —$V^{a14}$—$V^{a15}$ (where $V^{a14}$ is a single bond or a carbonyl group; and $V^{a15}$ is a hydrogen atom, a hydroxyl group, a $C_{1-6}$ alkyl group which may have a substituent(s), a $C_{2-6}$ alkenyl group which may have a substituent(s), a $C_{2-6}$ alkynyl group which may have a substituent(s), a $C_{3-8}$ cycloalkyl group which may have a substituent(s); a $C_{6-10}$ aryl group which may have a substituent(s), a 5- to 10-membered heteroaryl group which may have a substituent(s), a 3- to 10-membered non-aromatic heterocyclic group which may have a substituent(s), an amino group, a mono-$C_{1-6}$ alkylamino group which may have a substituent(s), a di-$C_{1-6}$ alkylamino group which may have a substituent(s), a formyl group, a carboxyl group or a $C_{2-7}$ alkoxycarbonyl group which may have a substituent(s)).

(ii) X

X in general formula (I) is an oxygen atom or a sulfur atom.

(iii) Y

Y in general formula (I) is a group represented by one of the following formulas:

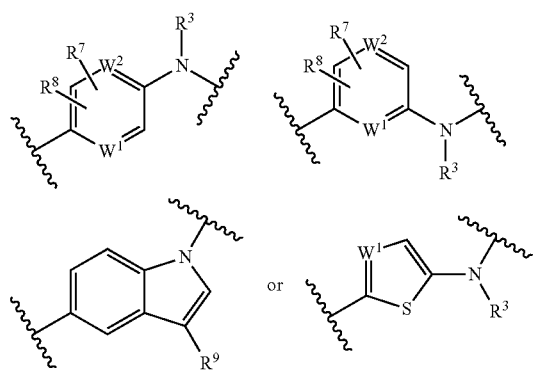

In the above formulas, $R^3$ is a hydrogen atom, a $C_{1-6}$ alkyl group which may have a substituent(s), a $C_{2-6}$ alkenyl group which may have a substituent(s), a $C_{2-6}$ alkynyl group which may have a substituent(s), a $C_{3-8}$ cycloalkyl group which may have a substituent(s), a $C_{2-7}$ acyl group which may have a substituent(s) or a $C_{2-7}$ alkoxycarbonyl group which may have a substituent(s).

$R^7$ and $R^8$ independently of each other represent a hydrogen atom, a halogen atom, a cyano group, a nitro group, an amino group, a $C_{1-6}$ alkyl group which may have a substituent(s), a $C_{3-8}$ cycloalkyl group which may have a substituent(s), a $C_{1-6}$ alkoxy group which may have a substituent(s), a $C_{1-6}$ alkylthio group which may have a substituent(s), a formyl group, a $C_{2-7}$ acyl group which may have a substituent(s), a $C_{2-7}$ alkoxycarbonyl group which may have a substituent(s) or a group represented by a formula —$CONV^{d1}V^{d2}$ (where $V^{d1}$ and $V^{d2}$ independently of each other represent a hydrogen atom or a $C_{1-6}$ alkyl group which may have a substituent(s)).

$R^9$ is a hydrogen atom, a halogen atom or a $C_{1-6}$ alkyl group which may have a substituent(s).

$W^1$ and $W^2$ independently of each other represent a carbon atom which may have a substituent or a nitrogen atom.

(iv) $R^4$ $R^4$ in general formula (I) is a hydrogen atom, a $C_{1-6}$ alkyl group which may have a substituent(s), a $C_{2-6}$ alkenyl group which may have a substituent(s), a $C_{2-6}$ alkynyl group which may have a substituent(s), a $C_{3-8}$ cycloalkyl group which may have a substituent(s), a $C_{2-7}$ acyl group which may have a substituent(s) or a $C_{2-7}$ alkoxycarbonyl group which may have a substituent(s).

(v) $R^5$ $R^5$ in general formula (I) is a hydrogen atom, a $C_{1-6}$ alkyl group which may have a substituent(s), a $C_{2-6}$ alkenyl group which may have a substituent(s), a $C_{2-6}$ alkynyl group which may have a substituent(s), a $C_{3-8}$ cycloalkyl group which may have a substituent(s), a $C_{6-10}$ aryl group which may have a substituent(s), a 5- to 10-membered heteroaryl group which may have a substituent(s) or a 3- to 10-membered non-aromatic heterocyclic group which may have a substituent(s).

Those compounds represented by general formula (I) may be prepared by known methods. For example, those compounds may be prepared by the method described in any of the following references: WO 02/32872, WO 2004/020434 and WO 2005/063713.

(B-2) General Formula (II)

In the present invention, preferably, the VEGF receptor kinase inhibitor is a compound represented by the following general formula (II):

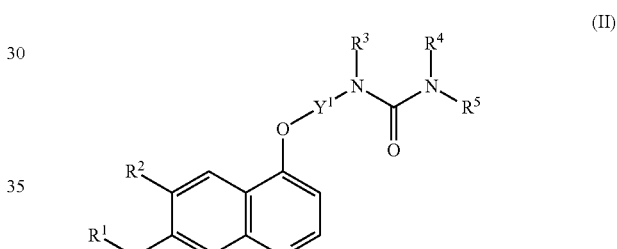

General formula (II) represents preferable examples in the compounds represented by general formula (I).

(i) $R^1$ $R^1$ is as defined above.

As preferable examples of $R^1$, $C_{1-6}$ alkyl groups may be given. For example, when $V^1$ is a $C_{1-6}$ alkylene group, $V^2$ is a single bond; and $V^3$ is a hydrogen atom in the definition of $R^1$, $R^1$ is a $C_{1-6}$ alkyl group. In this case, however, $R^1$ may have a substituent(s) selected from 3- to 10-membered non-aromatic heterocyclic group which may have $C_{1-6}$ alkyl group(s), hydroxyl group, $C_{1-6}$ alkoxy group, amino group, mono-$C_{1-6}$ alkylamino group and di-$C_{1-6}$ alkylamino group.

As more preferable examples of $R^1$, methyl group or a group represented by any of the following formulas may be given:

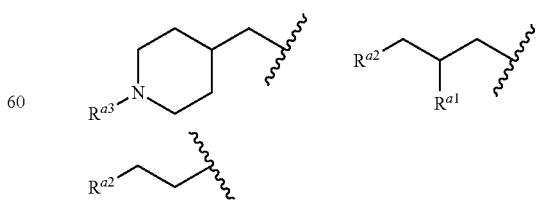

In the above formulas, $R^{a3}$ is a methyl group; $R^{a1}$ is a hydrogen atom or a hydroxyl group; and $R^{a2}$ is a methoxy group, an ethoxy group, a 1-pyrrolidinyl group, a 1-piperidinyl group, a 4-morpholinyl group, a dimethylamino group or a diethylamino group.

A still more preferable example of $R^1$ is methyl group or 2-methoxyethyl group.

(ii) $R^2$ $R^2$ is as defined above.

As preferable examples of $R^2$, cyano group or a group represented by a formula $CONV^{a11}V^{a12}$ (where $V^{a11}$ and $V^{a12}$ are as defined above) may be given.

As more preferable examples of $R^2$, cyano group or a group represented by a formula —$CONHV^{a16}$ (where $V^{a16}$ is a hydrogen atom, a $C_{1-6}$ alkyl group, a $C_{3-8}$ cycloalkyl group, a $C_{1-6}$ alkoxy group or a $C_{3-8}$ cycloalkoxy group, provided that $V^{a16}$ may have at least one substituent selected from the group consisting of halogen atoms, cyano group, hydroxyl group and $C_{1-6}$ alkoxy group) may be given.

As a still more preferable example of $R^2$, a group represented by a formula —$CONHV^{a17}$ (where $V^{a17}$ is a hydrogen atom, a $C_{1-6}$ alkyl group or a $C_{1-6}$ alkoxy group) may be given.

As a most preferable example of $R^2$, a group represented by a formula —$CONHV^{a18}$ (where $V^{a18}$ is a hydrogen atom, a methyl group or a methoxy group) may be given.

(iii) $Y^1$ $Y^1$ in general formula (II) is a group represented by one of the following formulas:

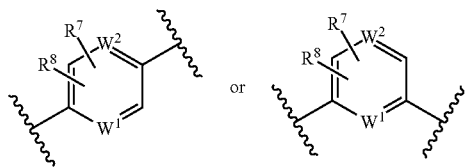

In the above formulas, $R^7$, $R^8$, $W^1$ and $W^2$ are as defined above.

As a preferable example of $Y^1$, a group represented by the following formula may be given.

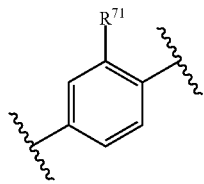

In the above formula, $R^{71}$ is a hydrogen atom or a halogen atom.

(iv) $R^3$ and $R^4$ $R^3$ and $R^4$ in general formula (II) are as defined above.

As a preferable example of $R^3$ and $R^4$, a hydrogen atom may be given for each of them.

(v) $R^5$ $R^5$ in general formula (II) is as defined above.

As preferable examples of $R^5$, a hydrogen atom, a $C_{1-6}$ alkyl group, a $C_{3-8}$ cycloalkyl group or a $C_{6-10}$ aryl group may be given, provided that $R^5$ may have a substituent(s) selected from the group consisting of halogen atoms and methanesulfonyl group.

As a more preferable example of $R^5$, a methyl group, an ethyl group or a cyclopropyl group may be given.

Preferable examples of the compounds represented by general formula (II) include the following compounds.

N-(4-(6-cyano-7-(2-methoxyethoxy)-4-quinolyl)oxy-2-fluorophenyl)-N'-(4-fluorophenyl)urea.

N-(2-chloro-4-((6-cyano-7-((1-methyl-4-piperidyl)methoxy)-4-quinolyl)oxy)phenyl)-N'-cyclopropylurea, N-(4-((6-cyano-7-(((2R)-3-(diethylamino)-2-hydroxypropyl)oxy)-4-quinolyl)oxy)phenyl)-N'-(4-fluorophenyl)urea, N-(4-((6-cyano-7-(((2R)-2-hydroxy-3-(1-pyrrolizino)propyl)oxy)-4-quinolyl)oxy)phenyl)-N'-(4-fluorophenyl)urea, 4-(3-chloro-4-(cyclopropylaminocarbonyl)aminophenoxy)-7-methoxy-6-quinolinecarboxamide, 4-(3-chloro-4-(cyclopropylaminocarbonyl)aminophenoxy)-7-(2-methoxyethoxy)-6-quinolinecarboxamide, N6-cyclopropyl-4-(3-chloro-4-(((cyclopropylamino)carbonyl)amino)phenoxy)-7-methoxy-6-quinolinecarboxamide, N6-(2-methoxyethyl)-4-(3-chloro-4-(((cyclopropylamino)carbonyl)amino)phenoxy)-7-methoxy-6-quinolinecarboxamide, N6-(2-fluoroethyl)-4-(3-chloro-4-(((cyclopropylamino)carbonyl)amino)phenoxy)-7-methoxy-6-quinolinecarboxamide, N6-methoxy-4-(3-chloro-4-(((cyclopropylamino)carbonyl)amino)phenoxy)-7-methoxy-6-quinolinecarboxamide, N6-methyl-4-(3-chloro-4-(((cyclopropylamino)carbonyl)amino)phenoxy)-7-methoxy-6-quinolinecarboxamide, N6-ethyl-4-(3-chloro-4-(((cyclopropylamino)carbonyl)amino)phenoxy)-7-methoxy-6-quinolinecarboxamide, 4-(3-fluoro-4-(cyclopropylaminocarbonyl)aminophenoxy)-7-(2-methoxyethoxy)-6-quinolinecarboxamide, 4-(3-chloro-4-(cyclopropylaminocarbonyl)aminophenoxy)-7-(2-hydroxyethoxy)-6-quinolinecarboxamide, 4-(3-chloro-4-(cyclopropylaminocarbonyl)aminophenoxy)-7-((2S)-2,3-dihydroxypropyl)oxy-6-quinolinecarboxamide, 4-(3-chloro-4-(methylaminocarbonyl)aminophenoxy)-7-methoxy-6-quinolinecarboxamide, 4-(3-chloro-4-(ethylaminocarbonyl)aminophenoxy)-7-methoxy-6-quinolinecarboxamide, N6-methoxy-4-(3-chloro-4-(((ethylamino)carbonyl)amino)phenoxy)-7-methoxy-6-quinolinecarboxamide, 4-(3-chloro-4-(cyclopropylaminocarbonyl)aminophenoxy)-7-(2-ethoxyethoxy)-6-quinolinecarboxamide, 4-(4-((cyclopropylamino)carbonyl)aminophenoxy)-7-(2-methoxyethoxy)-6-quinolinecarboxamide, N-(2-fluoro-4-((6-carbamoyl-7-methoxy-4-quinolyl)oxy)phenyl)-N'-cyclopropylurea, N6-(2-hydroxyethyl)-4-(3-chloro-4-(((cyclopropylamino)carbonyl)amino)phenoxy)-7-methoxy-6-quinolinecarboxamide, 4-(3-chloro-4-(1-propylaminocarbonyl)aminophenoxy)-7-methoxy-6-quinolinecarboxamide, 4-(3-chloro-4-(cis-2-fluoro-cyclopropylaminocarbonyl)aminophenoxy)-7-methoxy-6-quinolinecarboxamide, N6-methyl-4-(3-chloro-4-(((cyclopropylamino)carbonyl)amino)phenoxy)-7-(2-methoxyethoxy)-6-quinolinecarboxamide, N6-methyl-4-(3-chloro-4-(((ethylamino)carbonyl)amino)phenoxy)-7-methoxy-6-quinolinecarboxamide, 4-(3-chloro-4-(cyclopropylaminocarbonyl)aminophenoxy)-7-(2-(4-morpholino)ethoxy)-6-quinolinecarboxamide, 4-(3-chloro-4-(2-fluoroethylaminocarbonyl)aminophenoxy)-7-methoxy-6-quinolinecarboxamide, N6-((2R)tetrahydro-2-furanylmethyl)-4-(3-chloro-4-(((methylamino)carbonyl)amino)phenoxy)-7-methoxy-6-quinolinecarboxamide, 4-(3-fluoro-4-(ethylaminocarbonyl)aminophenoxy)-7-methoxy-6-quinolinecarboxamide, 4-(3-chloro-4-(((cyclopropylamino)carbonyl)amino)phenoxy)-7-((2R)-2-hydroxy-3-(1-pyrrolizino)propoxy)-6-quinolinecarboxamide, N6-methyl-4-(3-chloro-4-(((methylamino)carbonyl)amino)phenoxy)-7-((2R)-3-diethylamino-2-hydroxypropoxy)-6-quinolinecarboxamide, N6-methyl-4-(3-chloro-4-(((methylamino)carbonyl)amino)phenoxy)-7-((2R)-3-diethylamino-2-hydroxypropoxy)-6-quinolinecarboxamide, N6-methyl-4-(3-chloro-4-(((methylamino)carbonyl)amino)phenoxy)-7-((2R)-2-hydroxy-3-(1-pyrrolizino)propoxy)-6-quinolinecarboxamide, N6-methyl-4-(3-chloro-4-(((ethylamino)carbonyl)amino)phenoxy)-7-((2R)-2-hydroxy-3-(1-pyrrolizino)propoxy)-6-quinolinecarboxamide, N6-methyl-4-(3-chloro-4-(((methylamino)carbonyl)amino)phenoxy)-7-((1-methyl-4-piperidyl)methoxy)-6-quinolinecarboxamide, N6-methyl-4-(3-chloro-4-(((ethylamino)carbonyl)amino)phenoxy)-7-((1-methyl-4-piperidyl)methoxy)-6-quinolinecarboxamide, N-(4-(6-cyano-7-(2-methoxyethoxy)-4-quinolyl)oxy-2-fluorophenyl)-N'-cyclopropylurea, N-(4-(6-cyano-7-(3-(4-morpholino)propoxy)-4-quinolyl)oxyphenyl)-N'-(3-methylsulfonyl)phenyl)urea, 4-(4-((cyclopropylamino)carbonyl)aminophenoxy)-7-methoxy-6-quinolinecarboxamide, 4-(3-fluoro-4-((2-fluoroethylamino)carbonyl)aminophenoxy)-7-methoxy-6-quinolinecarboxamide, N6-(2-ethoxyethyl)-4-(3-chloro-4-(((methylamino)carbonyl)amino)phenoxy)-7-methoxy-6-quinolinecarboxamide, 4-(4-(3-ethylureido)-3-fluoro-phenoxy)-7-methoxyquinoline-6-carboxylic acid (2-cyanoethyl)amide, and N-(4-(6-(2-cyanoethyl)carbamoyl-7-methoxy-4-quinolyl)oxy-2-fluorophenyl)-N'-cyclopropylurea.

As more preferable examples of the compound represented by general formula (II) include the following compounds.

4-(3-chloro-4-(cyclopropylaminocarbonyl)aminophenoxy)-7-methoxy-6-quinolinecarboxamide, 4-(3-chloro-4-(ethylaminocarbonyl)aminophenoxy)-7-methoxy-6-quinolinecarboxamide, N6-methoxy-4-(3-chloro-4-(((cyclopropylamino)carbonyl)amino)phenoxy)-7-methoxy-6-quinolinecarboxamide, 4-(3-chloro-4-(methylaminocarbonyl)aminophenoxy)-7-methoxy-6-quinolinecarboxamide, and N6-methoxy-4-(3-chloro-4-(((ethylamino)carbonyl)amino)phenoxy)-7-methoxy-6-quinolinecarboxamide.

Further, as a still more preferable example of the compound represented by general formula (II), 4-(3-chloro-4-(cyclopropylaminocarbonyl)aminophenoxy-7-methoxy-6-quinolinecarboxamide (see formula (IV)) may be given. As one of the most preferable examples of VEGF receptor kinase inhibitors, the methanesulfonic acid salt of 4-(3-chloro-4-(cyclopropylaminocarbonyl)aminophenoxy-7-methoxy-6-quinolinecarboxamide may be given.

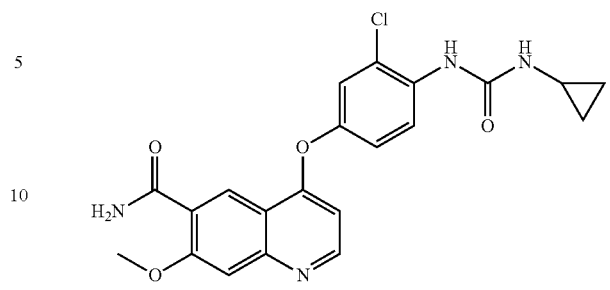

(IV)

Those compounds represented by general formula (II) may be prepared by known methods. For example, those compounds may be prepared by the method described in WO 02/32872 or WO 2005/063713.

(B-3) General Formula (III)

In the present invention, preferably, the VEGF receptor kinase inhibitor is a compound represented by the following general formula (III):

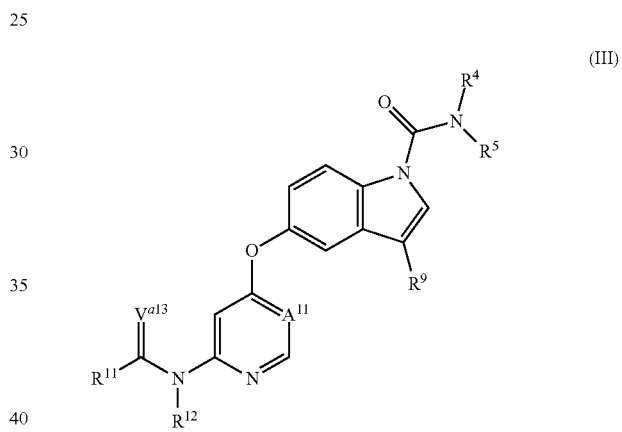

(III)

General formula (III) represents preferable examples in the compounds represented by general formula (I).

(i) $R^{11}$ $R^{11}$ is as defined above.

As preferable examples of $R^{11}$, 3- to 10-membered non-aromatic heterocyclic groups which may have a substituent(s) or mono-$C_{1-6}$ alkylamino groups which may have a substituent(s) may be given.

As a more preferable example of $R^{11}$, any one group selected from the groups represented by the following formulas may be given:

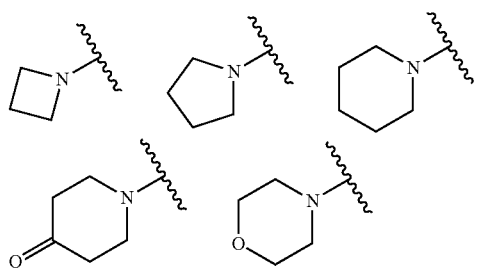

-continued

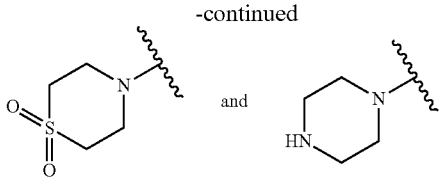
and

The above group may have a substituent(s) selected from the group of substituents described below.
[Group of Substituents]
Hydroxyl group, $C_{1-6}$ alkyl group, $C_{3-8}$ cycloalkyl group and groups represented by the formulas:

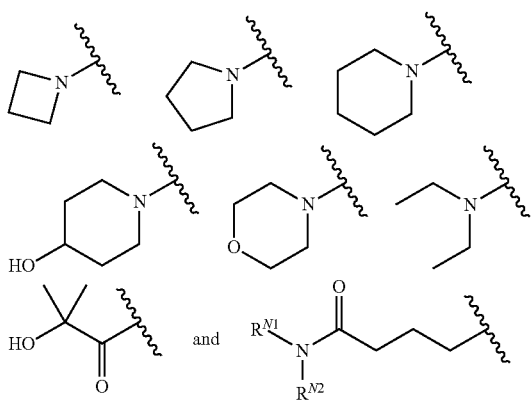
and wherein $R^{N1}$ and $R^{N2}$ independently of each other represent a hydrogen atom or a $C_{1-6}$ alkyl group which may have a substituent(s).

As a still more preferable example of $R^{11}$, any one group selected from the groups represented by the following formulas may be given:

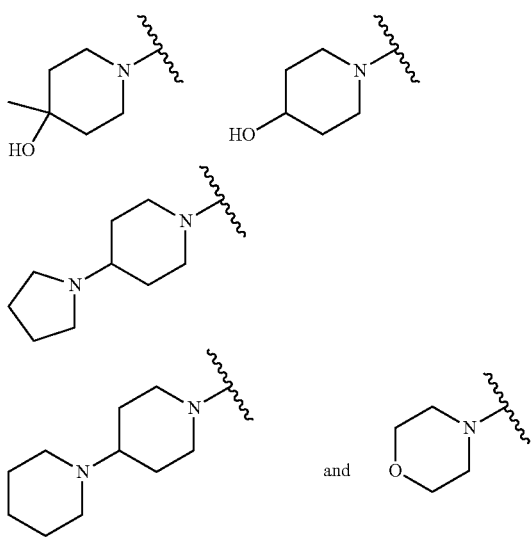
and (ii) $R^{12}$
$R^{12}$ is as defined above.
As a preferable example of $R^{12}$, a hydrogen atom may be given.

(iii) $V^{a13}$
$V^{a13}$ is as defined above.
As a preferable example of $V^{a13}$, an oxygen atom may be given.
(iv) $A^{11}$
$A^{11}$ is as defined above.
As a preferable example of $A^{11}$, a carbon atom may be given.
(v) $R^4$
$R^4$ is as defined above.
As a preferable example of $R^4$, a hydrogen atom may be given.
(vi) $R^5$
$R^5$ is as defined above.
As a preferable example of $R^5$, a $C_{1-6}$ alkyl group or a $C_{3-8}$ cycloalkyl group may be given.
As a more preferable of $R^5$, a methyl group may be given.
(vii) $R^9$
$R^9$ is as defined above.
As a preferable example of $R^9$, a hydrogen atom may be given.

Preferable examples of the compounds represented by general formula (III) include the following compounds.
5-(2-(((4-hydroxy-4-methylpiperidine-1-yl)carbonyl)amino)pyridine-4-yloxy)-1H-indole-1-carboxylic acid methylamide,
N1-methyl-5-(2-((4-hydroxypiperidino)carbonyl)amino-4-pyridyl)oxy-1H-1-indolecarboxamide,
N1-methyl-5-(2-(((4-pyrrolizine-1-yl)piperidine-1-yl)carbonyl)amino)pyridine-4-yloxy)-1H-1-indolecarboxamide,
N1-methyl-5-(2-(((4-piperidine-1-yl)piperidine-1-yl)carbonyl)amino)pyridine-4-yloxy)-1H-1-indolecarboxamide, and
N4-(4-(1-(methylamino)carbonyl-1H-5-indolyl)oxy-2-pyridyl)-4-morpholinecarboxamide.

The compounds represented by general formula (III) may be prepared by known methods, e.g., the method described in WO 2004/020434.
(B-4) Specific Examples of VEGF Receptor Kinase Inhibitors In the present invention, examples of the VEGF receptor kinase inhibitor include, but are not limited to, the following compounds.
(1) N-(4-bromo-2-fluorophenyl)-6-methoxy-7-[2-(1H-1,2,3-triazole-1-yl)ethoxy]quinazoline-4-amine (hereinafter, sometimes referred to as "ZD4190". Cancer Research., 60, 970-975, 2000, Journal of Medicinal Chemistry., 42: 5369-5389, 1999.) (See formula (V) below):

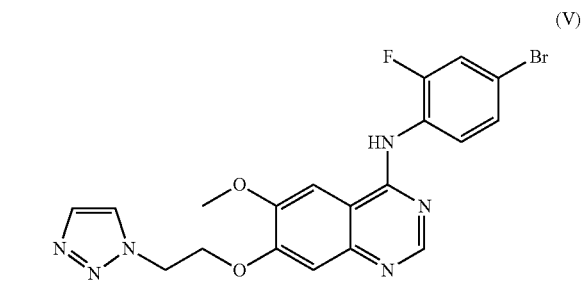 [SMILES: COc1cc2c(Nc3ccc(Br)cc3F)ncnc2cc1OCCn1ccnn1]

(V)

(2) N-(4-bromo-2-fluorophenyl)-6-methoxy-7-[(1-methylpiperidine-4-yl)methoxy]quinazoline-4-amine (hereinafter, sometimes referred to as "ZD6474" or "vandetanib".

Proc. Am. Assoc. Assoc. Cancer Research, 42, 583, 2001, Journal of Medicinal Chemistry, 45: 1300-1312, 2002.) (See formula (VI) below):

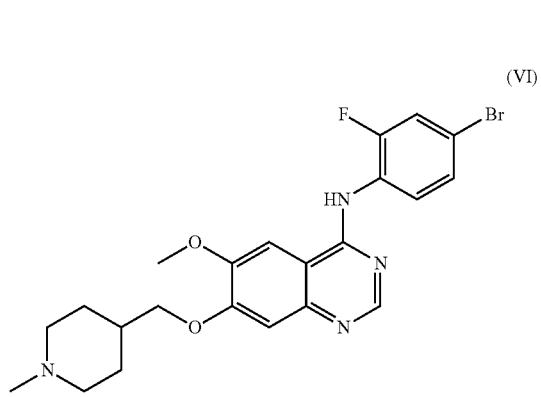 [SMILES: COc1cc2c(Nc3ccc(Br)cc3F)ncnc2cc1OCC1CCN(C)CC1]

(VI)

(3) 3-[(2,4-dimethylpyrrol-5-yl)methylene]-2-indolinone (hereinafter, sometimes referred to as "SU5416" or "semaxanib". Cancer Research., 59, 99-106, 1999, Journal of Medicinal Chemistry., 41: 2588-2603, 1998; U.S. Pat. No. 5,792,783.) (See formula (VII) below):

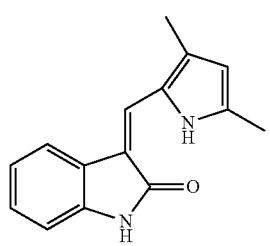

(VII)

(4) (Z)-3-[(2,4-dimethyl-5-(2-oxo-1,2-dihydroindole-3-ylidenemethyl)-1H-pyrrole-3-yl)-propionic acid (hereinafter, sometimes referred to as "SU6668". Cancer Research., 60, 4152-4160, 2000, Journal of Medicinal Chemistry, 42: 5120-5130, 1999.) (See formula (VIII) below):

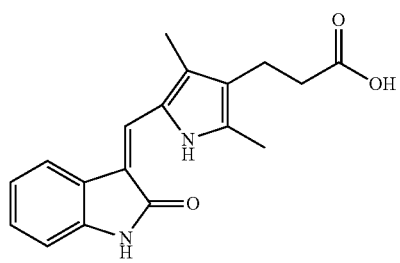

(VIII)

(5) 5-(5-fluoro-2-oxo-1,2-dihydroindole-3-ylidenemethyl)-2,4-dimethyl-1H-pyrrole-3-carboxylic acid (2-diethylaminoethyl)amide (hereinafter, sometimes referred to as "SU11248". Clinical Cancer Research, 9, 327-337, 2003, Journal of Medicinal Chemistry., 46: 1116-9, 2003.) (See formula (IX) below):

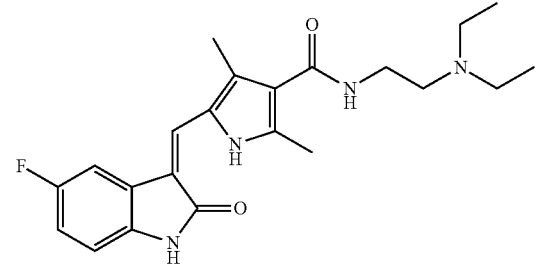

(IX)

(6) N,N-dimethylglycine-3-{5,6,7,13-tetrahydro-9-[(1-methylethoxy)methyl]-5-oxo-12H-indeno(2,1-a)pyrrolo[3,4-c]carbazole-12-yl}propylester (hereinafter, sometimes referred to as "CEP-7055". Pro. Am. Assoc. Cancer Research, 43, 1080, 2002, Journal of Medicinal Chemistry., 46: 5375-88, 2003.) (See formula (X) below):

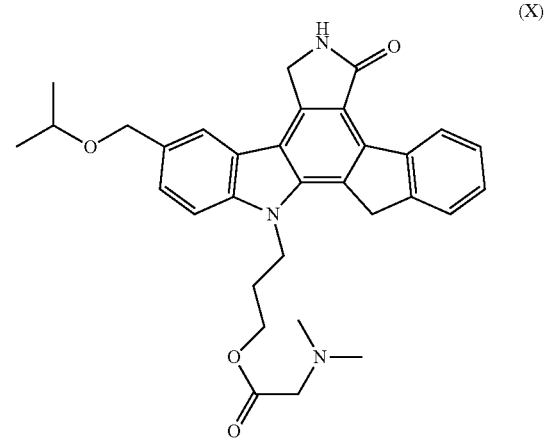 [SMILES: CC(C)OCc1ccc2c(c1)c1c3c(c4c(c1n2CCCOC(=O)CN(C)C)Cc1ccccc1-4)C(=O)NC3]

(X)

(7) 3-(4-bromo-2,6-difluoro-benzyloxy)-5-[3-(4-pyrrolizine-1-yl-butyl)-ureido]-isothiazole-4-carboxylic acid amide (hereinafter, sometimes referred to as "CP-547,632". Cancer Research. 63:7301-9, 2003, WO 99/62890.) (See formula (XI) below):

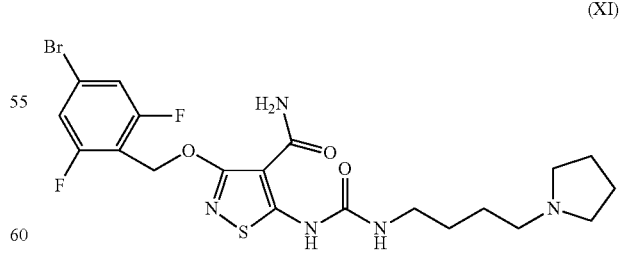

(XI)

(8) N-{2-chloro-4-[(6,7-dimethoxy-4-quinazolinyl)oxy]phenyl}-N'-propylurea (hereinafter, sometimes referred to as "KRN633". Molecular Cancer Therapeutics., 3:1639-49, 2004, WO 00/43366.) (See formula (XII) below):

(XII)

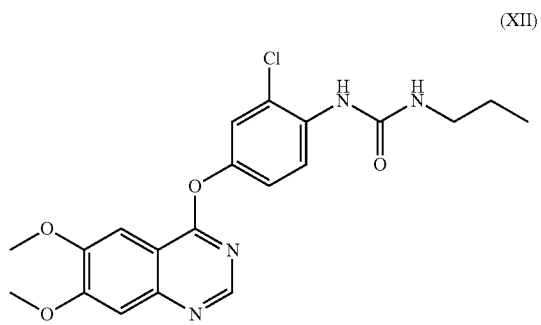 [SMILES: CCCNC(=O)Nc1ccc(Oc2ncnc3cc(OC)c(OC)cc23)cc1Cl]

(XV)

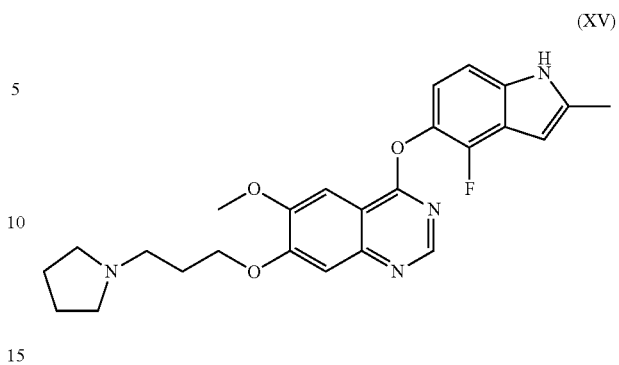

(9) 1-(4-chloroanilino)-4-(4-pyridylmethyl)phthalazine (hereinafter, sometimes referred to as "PTK787/ZK222584" or "vatalanib". Cancer Research. 60, 2179-2189, 2000, J. Med. Chem., 43:2310-23, 2000; WO 98/35958) (See formula (XIII) below):

(12) 6-[2-(methylcarbamoyl)phenylsulphanyl]-3-E-[2-(pyridine-2-yl)ethenyl]indazole (hereinafter, sometimes referred to as "AG013736". American Journal of Pathology. 165:35-52, 2004; WO 01/002369) (See formula (XVI) below):

(XIII)

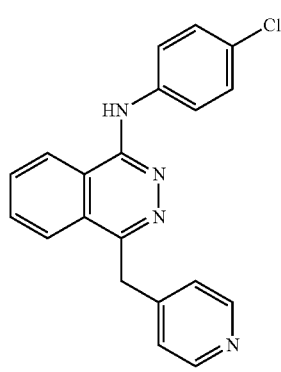

(XVI)

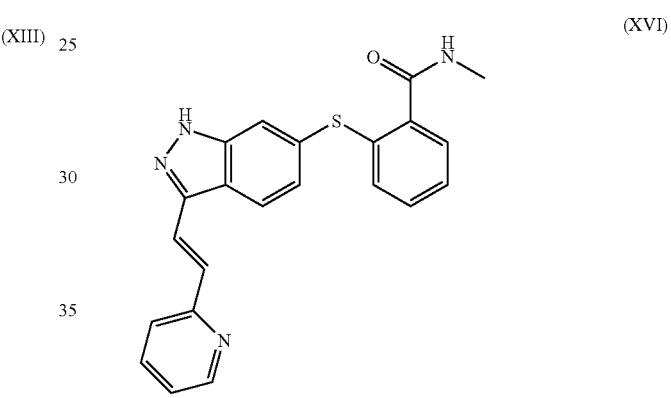

(10) N-{2-chloro-4-[(6,7-dimethoxy-4-quinolyl)oxy]phenyl}-N'-[5-methyl-3-isoxazolyl]urea (hereinafter, sometimes referred to as "KRN951"; WO 2002/088110) (See formula (XIV) below):

(13) 5-((Z)-(5-fluoro-2-oxo-1,2-dihydro-3H-indole-3-ylidene)methyl)-N-((2S)-2-hydroxy-3-morpholine-4-ylpropyl)-2,4-dimethyl-1H-pyrrole-3-carboxamide (hereinafter, sometimes referred to as "SU14813". Proceedings of the American Association for Cancer Research, 46, (Abstract 2031), 2005.) (See formula (XVII) below):

(XIV)

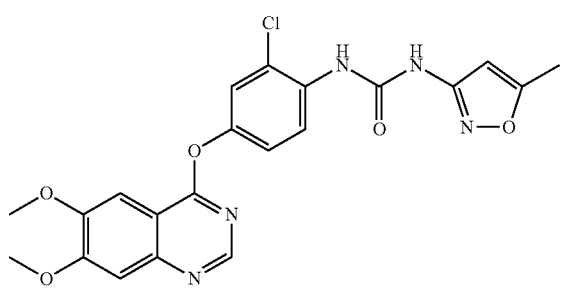

(XVII)

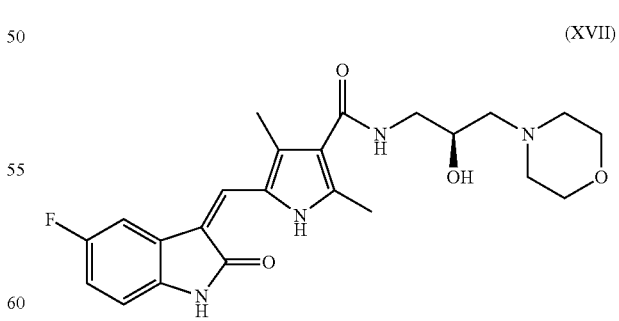

(11) 4-[(4-fluoro-2-methylindole-5-yl)oxy]-6-methoxy-7-[3-(pyrrolizine-1-yl)propoxy]quinazoline (hereinafter, sometimes referred to as "AZD2171". Cancer Research. 65:4389-400, 2005; WO 00/47212) (See formula (XV) below):

(14) 3-((quinoline-4-ylmethyl)amino)-N-(4-(trifluoromethoxy)phenyl)thiophene-2-carboxamide (hereinafter, sometimes referred to as "OSI930". Molecular Cancer Therapeutics., 4:1186-1197, 2005.) (See formula (XVIII) below):

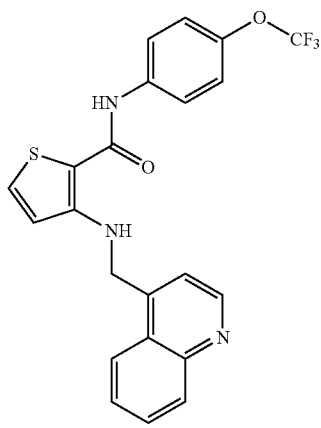

(XVIII)

(15) 6-(2,6-dichlorophenyl)-8-methyl-2-phenylamino-8H-pyrido[2,3-d]-pyrimidine-7-one (hereinafter, sometimes referred to as "TKI-28". Cancer Biol Ther., 4, 2005.) (See formula (XIX) below):

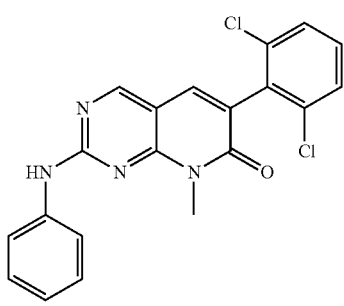

(XIX)

(16) 2-((1,6-dihydro-6-oxo-pyridine-3-ylmethyl)amino)-N-(3-(trifluoromethyl)phenyl)-3-pyridine-carboxamide (hereinafter, sometimes referred to as "ABP309". EORTC-NCI-AACR Symp Mol Targets Cancer Ther., 2, (Abstract 172), 2004.) (See formula (XX) below):

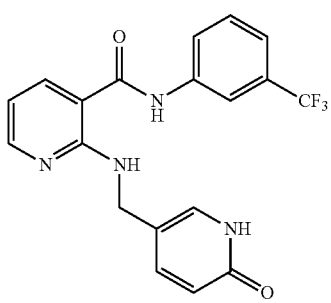

(XX)

(17) 4-(4-(4-chloro-phenylamino)-furo[2,3-d]pyridazine-7-yloxymethyl)pyridine-2-carboxylic acid methylamide (hereinafter, sometimes referred to as "BAY 57-9352". WO 01/23375) (See formula (XXI) below):

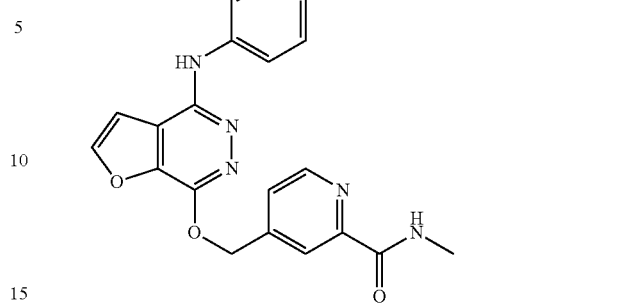

(XXI)

(18) N-(3-trifluoromethyl-4-chlorophenyl)-N'-(4-(2-methylcarbamoylpyridine-4-yl)oxyphenyl)urea (hereinafter, sometimes referred to as "BAY 43-9006" or "sorafenib". Cancer Research., 64, 7099-7109, 2004, Organic Process Res Dev., 6, 777-81, 2002.) (See formulas (XXII) below):

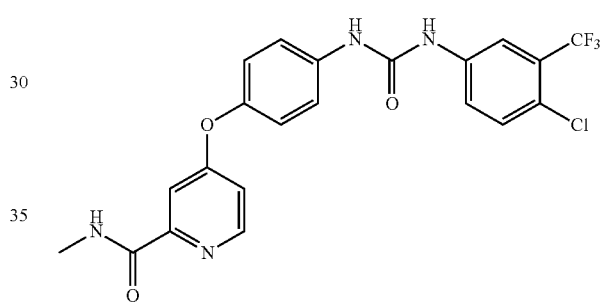

(XXII)

(19) 4-amino-5-fluoro-3-(6-(4-methyl-piperazine-1-yl)-1H-benzimidazole-2-yl)-1H-quinoline-2-one (hereinafter, sometimes referred to as "CHIR258". Clinical Cancer Research., 11, 3633-3641, 2005.) (See formula (XXIII) below):

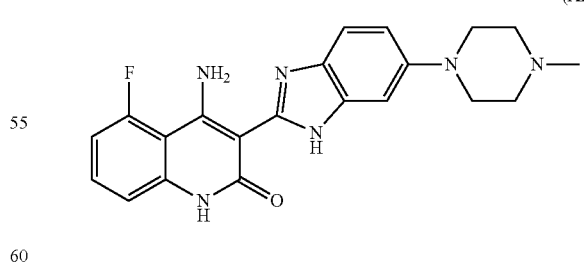

(XXIII)

(20) 4-(4-(1-amino-1-methyl-ethyl)-phenyl)-2-(4-(2-morpholine-4-yl-ethyl)phenylamino)-pyrimidine-5-carbonitrile (hereinafter, sometimes referred to as "JNJ17029259". Molecular Pharmacology., 66, 635-647, 2004.) (See formula (XXIV) below):

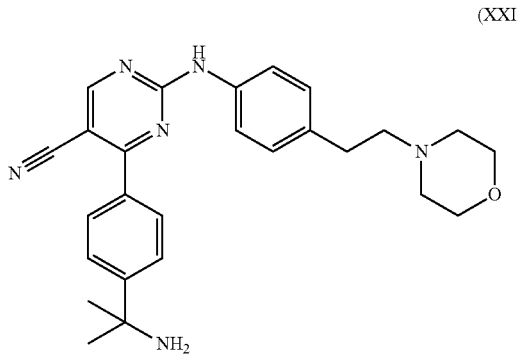

(21) [6-[4-[(4-ethylpiperazine-1-yl)methyl]phenyl]-7H-pyrrolo[2,3-d]pyrimidine-4-yl]-((R)-1-phenylethyl)amine (hereinafter, sometimes referred to as "AEE-788". Cancer Research., 64, 4931-4941, 2004; Cancer Research., 64, 7977-7984, 2004.) (See formula (XXV) below):

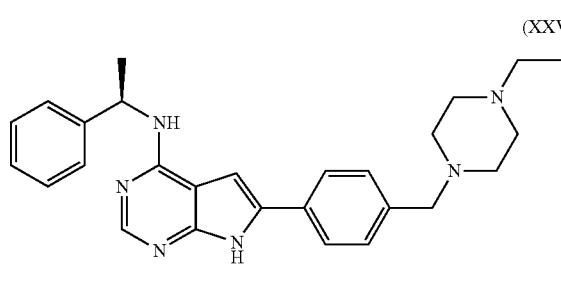

(22) 9-(1-methylethoxy)methyl-12-(3-hydroxypropyl)-6H,7H,13H-indeno[2,1-a]-pyrrole[3,4-c]carbazole-5-one (hereinafter, sometimes referred to as "CEP-5214". Journal of Medicinal Chemistry., 46, 5375-5388, 2003; Cancer Research, 63, 5978-5991, 2003.) (See formula (XXVI) below):

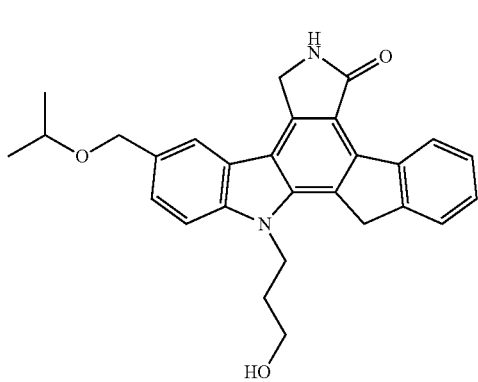

(23) N-(2,4-difluorophenyl)-N'-{4-[(6,7-dimethoxy-4-quinolyl)-oxy]-2-fluorophenyl}urea (hereinafter, sometimes referred to as "KI-8751". Journal of Medicinal Chemistry., 48, 1359-1366, 2005.) (See formula (XXVII) below):

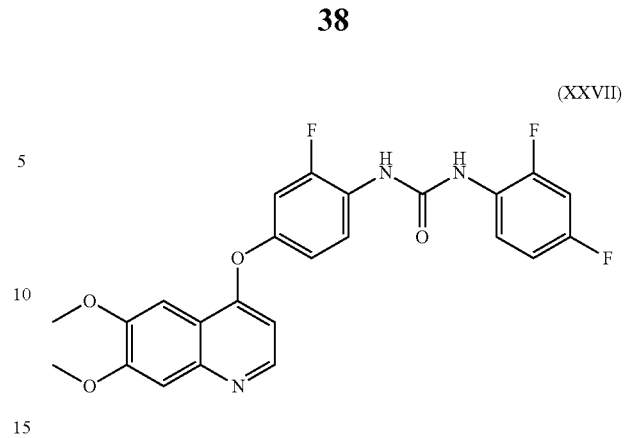

(24) N-[4-(3-amino-1H-indazole-4-yl)phenyl]-N'-(2-fluoro-5-methylphenyl)urea (hereinafter, sometimes referred to as "ABT-869". Proceedings of the American Association for Cancer Research., 46, 1407, (Abstract 5981), 2005.) (See formula (XXIX) below):

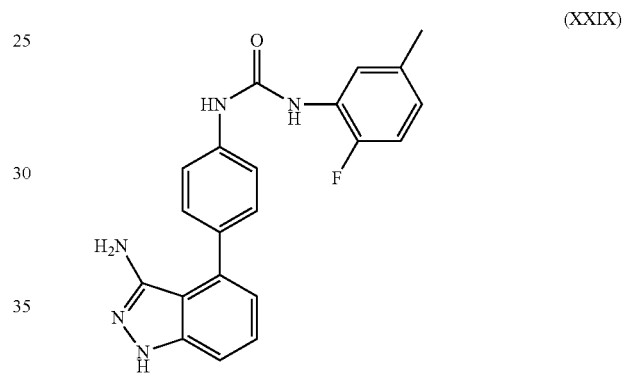

(25) 2-methyl-6-[2-(1-methyl-1-imidazole-2-yl)-thieno[3,2-b]pyridine-7-yloxy]-benzo[b]thiophene-3-carboxylic acid methylamide (hereinafter, sometimes referred to as "AG-028262". WO 03/06462; US Patent 2004/009965) (See formula (XXX) below):

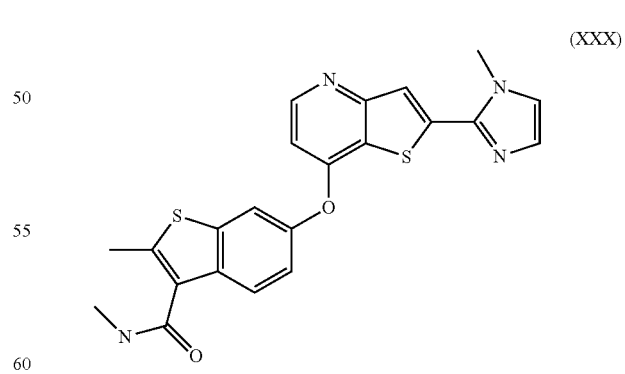

(26) (R)-1-(4-(4-fluoro-2-methyl-1H-indole-5-yloxy)-5-methylpyrrolo[1,2-f]-[1,2,4]triazine-6-yloxy)propane-2-ol (hereinafter, sometimes referred to as "BMS-540215" Proceedings of the American Association for Cancer Research, 46, (Abstract 3033), 2005.) (See formula (XXXI) below):

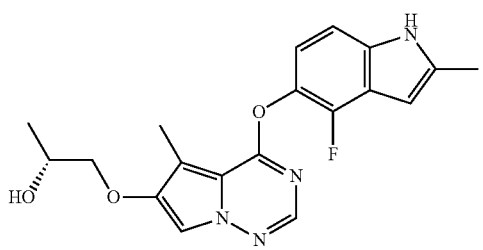

(27) (S)—((R)-1-(4-(4-fluoro-2-methyl-1H-indole-5-yloxy)-5-methylpyrrolo[1,2-f][1,2,4]triazine-6-yloxy)propane-2-ol)2-aminopropanoate (hereinafter, sometimes referred to as "BMS-582664". Proceedings of the American Association for Cancer Research., 46, (Abstract 3033), 2005.) (See formulas (XXXII) below):

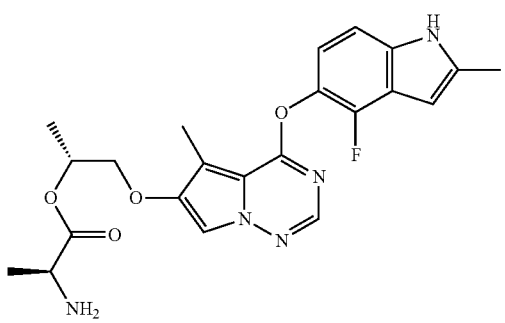

(28) 3-[(4-morpholine-4-yl-phenylamino)-methylene]-1,3-dihydroindole-2-one (hereinafter, sometimes referred to as "AGN-199659". WO 2003/027102) (See formula (XXXIII) below):

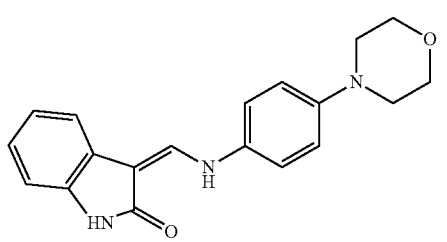

(29) 5-[[4-(2,3-dimethyl-2H-indazole-6-yl)methylamino]pyrimidine-2-yl]amino]-2-methylbenzenesulfonamide (hereinafter, sometimes referred to as "pazopanib" or "GW-786034". Proc. Am. Soc. Clin. Oncology, (Abstract 3054), 2004.) (See formula (XXXIV) below):

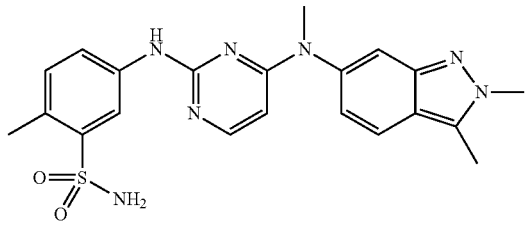

(30) (3Z)-3-[6-(2-morpholine-4-ylethoxy)quinoline-2(1H)-ylidene]-1,3-dihydro-2H-indole-2-one (hereinafter, sometimes referred to as "YM-231146". Biological and Pharmaceutical Bulletin. 28:2096-2101, 2005.) (See formula (XXXV) below):

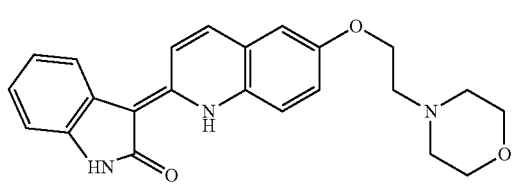

(31) 2-((2-((4-(4-(4-(tert-butyl)anilino)phenoxy)-6-methoxy-7-quinolyl)oxy)ethyl)amino)-1-ethanol (hereinafter, sometimes referred to as "KI-23057". WO 2003/033472) (See formula (XXXVI) below):

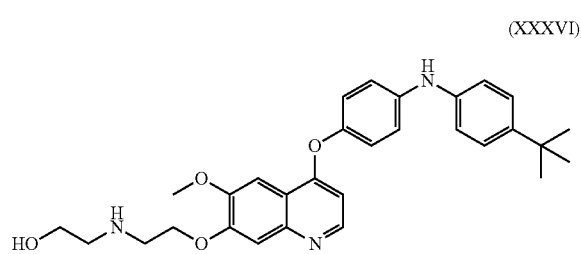 [SMILES: COc1cc2c(Oc3ccc(Nc4ccc(C(C)(C)C)cc4)cc3)ccnc2cc1OCCNCCO]

The above-described ZD4190, ZD6474, SU5416, SU6668, SU11248, CEP-7055, CP-547,632, KRN633, PTK787/ZK222584, KRN951, AZD2171, AG013736, SU14813, OSI930, TKI-28, ABP309, BAY 57-9352, BAY 43-9006, CHIR258, JNJ17029259, AEE-788, CEP-5214, KI-8751, ABT-869, AG-028262, BMS-540215, BMS-582664, AGN-199659, pazopanib, YM-231146 and KI-23057 may be prepared by known methods. For example, they may be prepared by the methods described in respective references.

In the present invention, other examples of the VEGF receptor kinase inhibitor include BIBF1120 (WO 01/27081), ZK304709 (Proceedings of the American Association for Cancer Research, 46, (Abstract 5842), 2005), Exel7647 (EORTC-NCI-AACR Symp Mol Targets Cancer Ther., (Abstract 134), 2004), AMG706 (EORTC-NCI-AACR Symp Mol Targets Cancer Ther., 2, (Abstract 151), 2004) and GW-654652 (Blood., 103, 3474-3479, 2004; Proceedings of the American Association for Cancer Research, 44, 9, (Abstract 39), 2003; Proceedings of the American Association for Cancer Research, 44, 9, (Abstract 40), 2003). BIBF1120, ZK304709, Exel7647, AMG706 and GW-654652 may be prepared by known methods.

(C) Anti-VEGF Receptor Antibody

In the present invention, as one example of the VEGF inhibitor, anti-VEGF receptor antibody may be given. Anti-VEGF receptor antibody is an antibody which has affinity for VEGF receptor or a partial fragment thereof. Preferably, this anti-VEGF receptor antibody is a neutralizing antibody that recognizes and binds to VEGF receptor and thereby inhibits the activity of VEGF (such as vascular endothelial cell growth activity). Anti-VEGF receptor antibody may be prepared in the same manner as described later for the preparation of anti-VEGF antibody Anti-VEGF receptor antibody may be either a polyclonal antibody or a monoclonal antibody. The isotype of the anti-VEGF receptor antibody is not particularly limited. Further, the anti-VEGF receptor antibody may be a fragment of an antibody or a single-chain antibody (see the description of anti-VEGF antibody provided later).

Preferable examples of the anti-VEGF receptor antibody include, but are not limited to, 2C3 antibody (U.S. Pat. No. 6,524,583, U.S. Pat. No. 6,676,941), IMC-1121b (U.S. Pat. No. 6,811,779), IMC-18F1 (Proceedings of the American Association for Cancer Research, 45, 694, (Abstract 3005), 2004), IMC-1C11 (U.S. Pat. No. 5,747,651) and IMC-2C6 (Proceedings of the American Association for Cancer Research, 44, 1479, (Abstract 6454), 2003). 2C3 antibody, IMC-1121b, IMC-18F1, IMC-1C11 and IMC-2C6 may be prepared by known methods. For example, they may be prepared by the methods described in respective references.

(D) Other VEGF Inhibitors

In the present invention, examples of the VEGF inhibitor include PI88, AVE-0005 (Proc. Am. Soc. Clin. Oncology, (Abstract 776), 2003), EG-3306 (Biochem Biophys Res Commun., 302, 793-799, 2003), RPI-4610 (Angiozyme™, U.S. Pat. No. 5,180,818, U.S. Pat. No. 6,346,398), 2-(8-hydroxy-6-methoxy-1-oxo-1H-benzopyran-3-yl)propionic acid (hereinafter, sometimes referred to as "NM-3"; WO 97/48693), 5-[N-methyl-N-(4-octadecyloxyphenyl)acetyl]amino-2-methylthiobenzoic acid (hereinafter, sometimes referred to as "VGA-1155"; Anticancer Research., 24, 3009-3017, 2004) (See formula (LII) below):

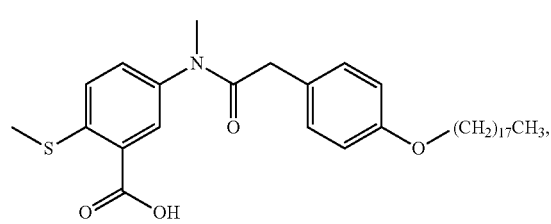

(LII)

VEGF trap (The Journal of Clinical Endocrinology & Metabolism. 86(7), 3377-3386, 2001) and pegaptanib sodium (Macugen™). PI88, AVE-0005, EG-3306, RPI-4610, NM-3, VGA-1155 and VEGF trap may be prepared by known methods. For example, they may be prepared by the methods described in respective references. Pegaptanib sodium may be obtained by purchasing Macugen™ from Pfizer.

(E) FGF Receptor Kinase Inhibitors

In the present invention, examples of the FGF receptor kinase inhibitor include, but are not limited to, the following compounds.

(1) 1-[2-amino-6-(3,5-dimethoxyphenyl)-pyrido(2,3-d)pyrimidine-7-yl]-3-tert-butylurea (hereinafter, sometimes referred to as "PD166866"; Journal of Medicinal Chemistry., 40, 2296-2303, 1997) (See formula (XXXVII) below):

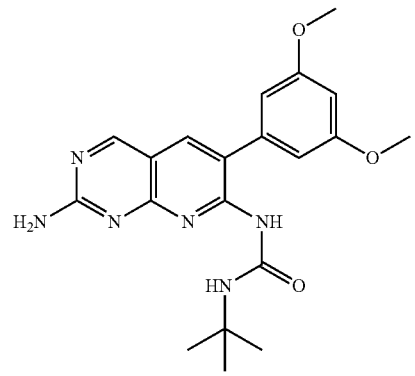

(XXXVII)

(2) 1-tert-butyl-3-[2-(4-diethylamino)butylamino-6-(3,5-dimethoxyphenyl)pyrido(2,3-d)pyrimidine-7-yl]urea (hereinafter, sometimes referred to as "PD173074"; EMBO J., 17, 5896-5904, 1998; U.S. Pat. No. 5,733,913) (See formula (XXXVIII) below):

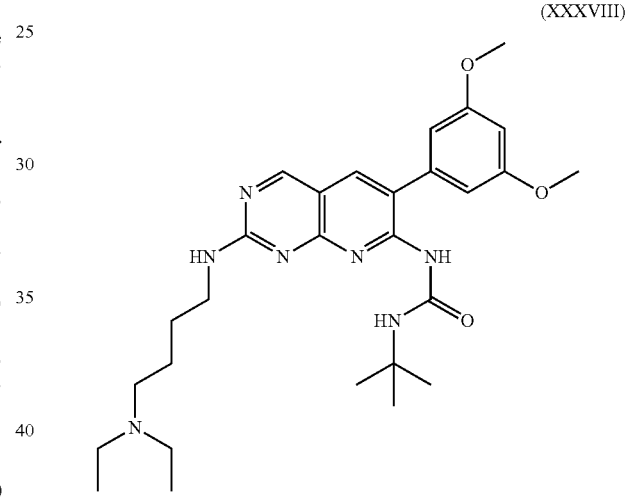

(XXXVIII)

(3) (S)—((R)-1-(4-(4-fluoro-2-methyl-1H-indole-5-yloxy)-5-methylpyrrolo[1,2-f]-[1,2,4]triazine-6-yloxy)propane-2-ol)2-aminopropanoate (BMS-582664) (See formula (XXXII))

(4) 4-[4-[N-(4-nitrophenyl)carbamoyl]-1-piperazinyl]-6,7-dimethoxyquinazoline (hereinafter, sometimes referred to as "CT-052923"; WO 98/14437) (See formula (XXXIX) below):

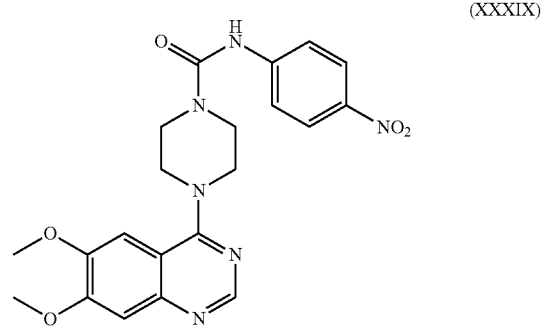 [SMILES: COc1cc2ncnc(N3CCN(C(=O)Nc4ccc([N+](=O)[O-])cc4)CC3)c2cc1OC]

(XXXIX)

(5) 4-amino-5-fluoro-3-(6-(4-methyl-piperazine-1-yl)-1H-benzimidazole-2-yl)-1H-quinoline-2-one (CHIR258) (See formula (XXIII))

(6) 2-((2-((4-(4-(4-(tert-butyl)anilino)phenoxy)-6-methoxy-7-quinolyl)oxy)ethyl)amino)-1-ethanol (KI-23057) (See formula (XXXVI))

(7) (Z)-3-[(2,4-dimethyl-5-(2-oxo-1,2-dihydroindole-3-ylidenemethyl)-1H-pyrrole-3-yl)-propionic acid (SU6668) (See formula (VIII))

PD166866, PD173074, BMS-582664, CT-052923, CHIR258, KI-23057 and SU6668 may be prepared by known methods. For example, they may be prepared by the methods described in respective references.

(F) Anti-FGF Receptor Antibody

In the present invention, as one example of the FGF inhibitor, anti-FGF receptor antibody may be givens Anti-FGF receptor antibody is an antibody which has affinity for FGF receptor or a partial fragment thereof. Preferably, this anti-FGF receptor antibody is a neutralizing antibody that recognizes and binds to FGF receptor and thereby inhibits the activity of FGF (such as vascular endothelial cell growth activity). Anti-FGF receptor antibody may be prepared in the same manner as described later for the preparation of anti-VEGF antibody. Anti-FGF receptor antibody may be either a polyclonal antibody or a monoclonal antibody. The isotype of the anti-FGF receptor antibody is not particularly limited. Further, the anti-FGF receptor antibody may be a fragment of an antibody or a single-chain antibody (see the description of anti-VEGF antibody provided later).

(G) PDGF Receptor Kinase Inhibitor

In the present invention, as one example of the PDGF inhibitor, PDGF receptor kinase inhibitor may be given. Examples of the PDGF receptor kinase inhibitor include, but are not limited to, the following compounds.

(1) 4-(4-methylpiperazine-1-ylmethyl)-N-[4-methyl-3-[4-(3-pyridyl)pyrimidine-2-ylamino]phenyl]benzeneamide (hereinafter, sometimes referred to as "imatinib") (See formula (XL) below):

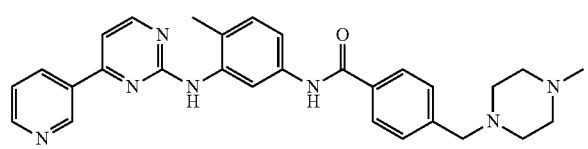

(2) 6-[2-(methylcarbamoyl)phenylsulphanyl]-3-E-[2-(pyridine-2-yl)ethenyl]-indazole (AG013736) (See formula (XVI))

(3) 1-{2-[5-(2-methoxy-ethoxy)-benzoimidazole-1-yl]-quinoline-8-yl}-piperidine-4-ylamine (hereinafter, sometimes referred to as "CP-673451"; WO 2001/040217; Cancer Research., 65, 957-966, 2005.) (See formula (XLI) below):

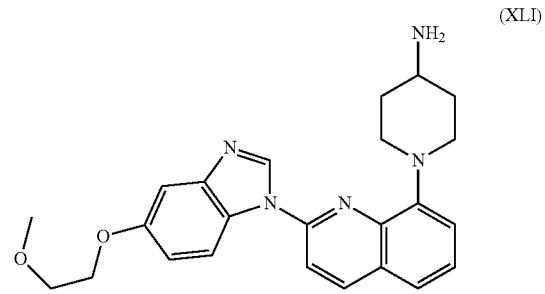 [SMILES: COCCOc1ccc2c(c1)ncn2-c1ccc2cccc(N3CCC(N)CC3)c2n1]

(4) 4-[4-[N-(4-nitrophenyl)carbamoyl]-1-piperazinyl]-6,7-dimethoxyquinazoline (CT-052923) (See formula (XXXIX))

(5) 4-amino-5-fluoro-3-(6-(4-methyl-piperazine-1-yl)-1H-benzimidazole-2-yl)-1H-quinoline-2-one (CHIR258) (See formula (XXIII))

(6) (4-tert-butylphenyl) {4-[(6,7-dimethoxy-4-quinolyl)oxy]phenyl}methaneone (hereinafter, sometimes referred to as "KI-6896"; Bioorganic and Medicinal Chemistry Letters., 7, 2935-2940, 1997.) (See formula (XLIII) below):

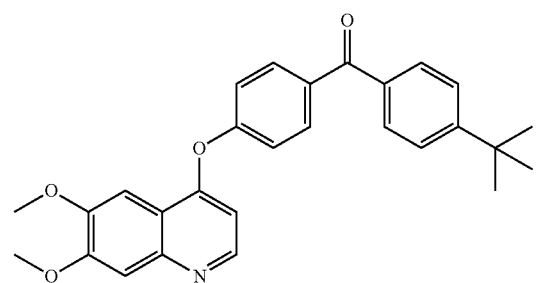

(7) 5-methyl-N-[4-(trifluoromethyl)phenyl]-4-isoxazolecarboxamide (hereinafter, sometimes referred to as "leflunomide".) (See formula (XLIV) below):

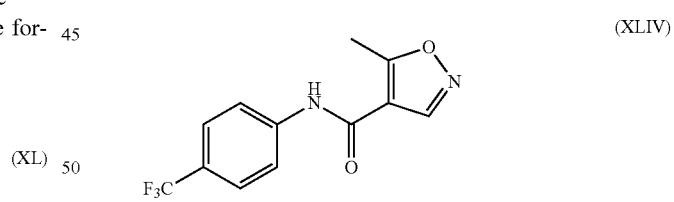

(8) trans-4-[(6,7-dimethoxyquinoxaline-2-yl)amino]cyclohexanol (hereinafter, sometimes referred to as "RPR-127963E".) (See formula (XLV) below):

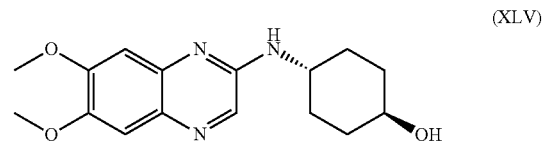 [SMILES: COc1cc2ncc(N[C@H]3CC[C@H](O)CC3)nc2cc1OC]

(9) (Z)-3-[(2,4-dimethyl-5-(2-oxo-1,2-dihydro indole-3-ylidenemethyl)-1H-pyrrole-3-yl)-propionic acid (SU6668) (See formula (VIII))

(10) 5-(5-fluoro-2-oxo-1,2-dihydroindole-3-ylidenemethyl)-2,4-dimethyl-1H-pyrrole-3-carboxylic acid (2-diethylaminoethyl)amide (SU11248) (See formula (IX))

(11) 1-(4-chloroanilino)-4-(4-pyridylmethyl)phthalazine (PTK787/ZK222584) (See formula (XIII))

(12) N-[4-(3-amino-1H-indazole-4-yl)phenyl-N'-(2-fluoro-5-methylphenyl)urea (ABT-869) (See formula (XXIX))

Imatinib, AG013736, CP-673451, CT-052923, CHIR258, KI-6896, leflunomide, RPR-127963E, SU6668, SU11248, PTK787/ZK222584 and ABT-869 may be prepared by known methods. For example, they may be prepared by the methods described in respective references.

Imatinib may be obtained by purchasing Glivec™ from Novartis.

(H) Anti-PDGF Receptor Antibody

In the present invention, as one example of the PDGF inhibitor, anti-PDGF receptor antibody may be given. Anti-PDGF receptor antibody is an antibody which has affinity for PDGF receptor or a partial fragment thereof. Preferably, this anti-PDGF receptor antibody is a neutralizing antibody that recognizes and binds to PDGF receptor and thereby inhibits the activity of PDGF (such as vascular endothelial cell growth activity). Anti-PDGF receptor antibody may be prepared in the same manner as described later for the preparation of anti-VEGF antibody. Anti-PDGF receptor antibody may be either a polyclonal antibody or a monoclonal antibody. The isotype of the anti-PDGF receptor antibody is not particularly limited. Further, the anti-PDGF receptor antibody may be a fragment of an antibody or a single-chain antibody (see the description of anti-VEGF antibody provided later).

(I) EGF Receptor Kinase Inhibitors

In the present invention, as one example of the EGF inhibitor, EGF receptor kinase inhibitor may be given. Specifically, examples of the EGF receptor kinase inhibitor include gefitinib and derivatives thereof. Gefitinib refers to 4-(3-chloro-4-fluorophenylamino)-7-methoxy-6-(3-(4-morpholino)propoxy-quinazoline). The structural formula thereof is shown in formula (XLVI) below:

(XLVI)

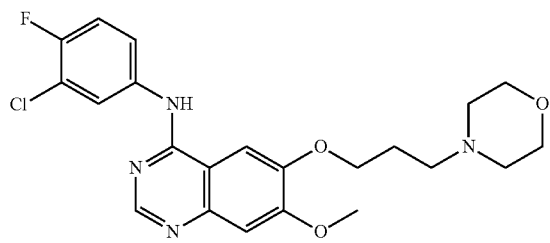

As derivatives of gefitinib, the compounds disclosed in WO 96/33980 may be given.

Gefitinib and derivatives thereof may be prepared by known methods. For example, they may be prepared by the method described in any one of WO 96/33980, Japanese Patent 3040486 and U.S. Pat. No. 5,770,599.

Alternatively, gefitinib may be obtained by purchasing Iressa™ from Astrazeneca.

In the present invention, further examples of the EGF receptor kinase inhibitor include erlotinib and derivatives thereof. Erlotinib refers to 4-(3-ethynylphenylamino)-6,7-bis(2-methoxyethoxy)-quinazoline. The structural formula thereof is shown in formula (XLVII) below:

(XLVII)

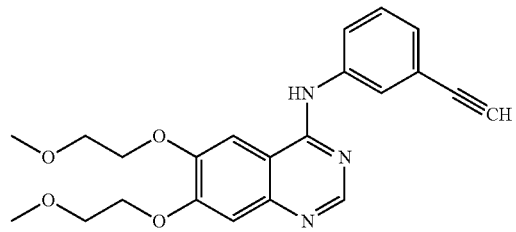

As derivatives of erlotinib, the compounds disclosed in WO 96/30347 may be given.

Erlotinib and derivatives thereof may be prepared by known methods. For example, they may be prepared by the method described in any one of WO 96/30347, Japanese Patent 3088018 and Japanese Patent 3420549.

Alternatively, erlotinib may be obtained by purchasing Tarceva™ from Genentech.

In the present invention, other examples of the EGF receptor kinase inhibitor include the following compounds.

(1) N-[3-chloro-4-[(3-fluorobenzyl)oxy]phenyl]-6-[5-[[[2-(methylsulfonyl)ethyl]-amino]methyl]furan-2-yl]quinazolin-4-amine (hereinafter, sometimes referred to as "lapatinib"; WO 99/35146; Cancer Research., 64, 6652-6659, 2004) (See formula (XLVIII) below):

(XLVIII)

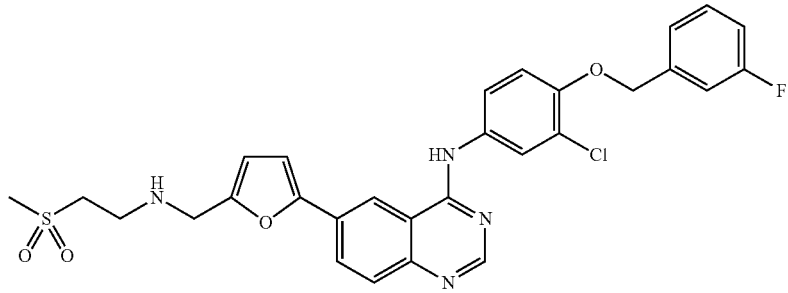

(2) N-[4-[N-(3-chloro-4-fluorophenyl)amino]-7-[3-(4-morpholinyl)propoxy]-quinazolin-6-yl]acrylamide (hereinafter, sometimes referred to as "canertinib"; Clinical Cancer Research, 10:691-700, 2004; WO 2000/31048) (See formula (XLIX) below):

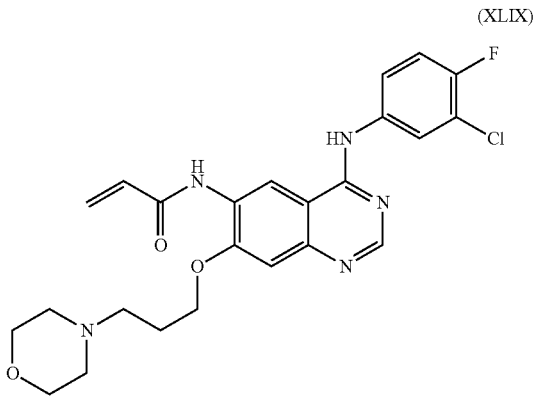 [SMILES: C=CC(=O)Nc1cc2c(Nc3ccc(F)c(Cl)c3)ncnc2cc1OCCCN1CCOCC1]

(XLIX)

(3) (2E)-N-[4-[(3-chloro-4-fluorophenyl)amino]-3-cyano-7-ethoxy-6-quinolinyl]-4-(dimethylamino)-2-butenamide (hereinafter, sometimes referred to as "pelitinib"; WO 2003/50090) (See formula (L) below):

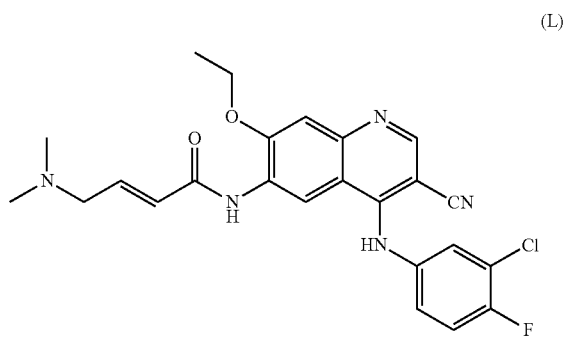 [SMILES: CCOc1cc2ncc(C#N)c(Nc3ccc(F)c(Cl)c3)c2cc1NC(=O)/C=C/CN(C)C]

(L)

(4) [6-[4-[(4-ethylpiperazine-1-yl)methyl]phenyl]-7H-pyrrolo[2,3-d]pyrimidine-4-yl]-((R)-1-phenylethyl)amine (AEE-788) (See formula (XXV))

(5) (E)-N-{4-[3-cloro-4-(2-pyridinylmethoxy)anilino]-3-cyano-7-ethoxy-6-quinolinyl}-4-(dimethylamino)-2-butenamide (hereinafter, sometimes referred to as "HKI-272"; Cancer Research., 64, 3958-3965, 2004; Journal of Medicinal Chemistry, 48, 1107-1131, 2005.) (See formula (LI) below):

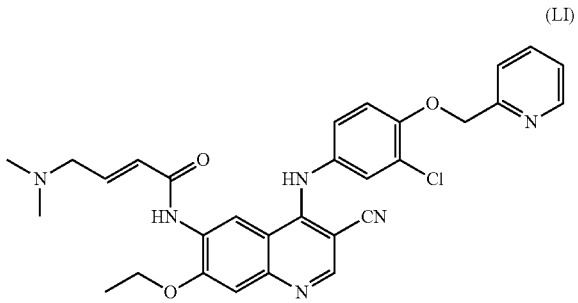 [SMILES: CCOc1cc2ncc(C#N)c(Nc3ccc(OCc4ccccn4)c(Cl)c3)c2cc1NC(=O)/C=C/CN(C)C]

(LI)

In the present invention, the EGF receptor kinase inhibitor is preferably 4-(3-ethynylphenylamino)-6,7-bis(2-methoxyethoxy)-quinazoline (erlotinib: formula (XLVII) above).

Lapatinib, canertinib, pelitinib, AEE-788 and HKI-272 may be prepared by known methods. For example, they may be prepared the methods described in respective references.

Further, in the present invention, examples of the EGF receptor kinase inhibitor also include ARRY-334543 (Am. Assoc. Cancer Research, A3399, 2005) and MP-412 (Am. Assoc. Cancer Research, A3394, 2005; Am. Assoc. Cancer Research, A3405, 2005). ARRY-334543 and MP-412 may be prepared by known methods.

(J) Anti-EGF Receptor Antibody

In the present invention, as one example of the EGF inhibitor, anti-EGF receptor antibody may be given. Anti-EGF receptor antibody is an antibody which has affinity for EGF receptor or a partial fragment thereof. Preferably, this anti-EGF receptor antibody is a neutralizing antibody that recognizes and binds to EGF receptor and thereby inhibits the activity of EGF (such as vascular endothelial cell growth activity). Anti-EGF receptor antibody may be prepared in the same manner as described later for the preparation of anti-VEGF antibody. Anti-EGF receptor antibody may be either a polyclonal antibody or a monoclonal antibody. The isotype of the anti-EGF receptor antibody is not particularly limited. Further, the anti-EGF receptor antibody may be a fragment of an antibody or a single-chain antibody (see the description of anti-VEGF antibody provided later).

In the present invention, a preferable example of the anti-EGF receptor antibody is cetuximab.

Cetuximab may be prepared by the method described in Japanese Unexamined Patent Publication No. 2002-114710 or No. Hei 2-291295.

Alternatively cetuximab may be obtained by purchasing Erbitux™ from Merck.

In the present invention, as another example of the anti-EGF receptor antibody, nimotuzumab may be given. Nimotuzumab may be prepared by the method described in European Patent 203126 or U.S. Pat. No. 5,891,996.

In the present invention, examples of the anti-EGF receptor antibody further include panitumumab (CAS 339177-26-3; Clinical Colorectal Cancer. 2005; 5(1):21-3), matuzumab (CAS 339186-68-4; Curr Opin Mol Ther. 2004; 6(1):96-103), IMC-11F8 (Am. Assoc. Cancer Research, A5353, 2005) and MDX-447 (ASCO 18: 433, 1999).

(K) Salts and Solvates of Angiogenesis Inhibitors

In the present invention, the angiogenesis inhibitor may form a pharmacologically acceptable salt with acid or base. The above-described angiogenesis inhibitor in the present invention includes such pharmacologically acceptable salts. Examples of salts formed with acid include, but are not limited to, inorganic acid salts such as hydrochlorides, hydrobromates, sulfates and phosphates; and organic acid salts such as formates, acetates, lactates, succinates, fumarates, maleates, citrates, tartrates, stearates, benzoates, methanesulfonates, benzenesulfonates, p-toluenesulfonates and trifluoroacetates. Examples of salts formed with base include, but are not limited to, alkali metal salts such as sodium salts and potassium salts; alkaline earth metal salts such as calcium salts and magnesium salts; organic base salts such as trimethylamine salts, triethylamine salts, pyridine salts, picoline salts, dicyclohexylamine salts, N',N'-dibenzylethylenediamine salts, arginine salts and lysine salts; and ammonium salts.

Further, in the present invention, the angiogenesis inhibitor includes the solvates of these compounds and, when these compounds have optical isomers, the solvates thereof and the optical isomers. Examples of the solvate include, but are not limited to, hydrates and non-hydrates. Hydrates are preferable. Examples of solvents include, but are not limited to, water, alcohols (such as methanol, ethanol, n-propanol) and dimethylformamide.

Further, in the present invention, the angiogenesis inhibitor may be in the form of crystal or non-crystal. When there is crystalline polymorphism, the angiogenesis inhibitor may be a single product of any one of the crystal forms or a mixture of such forms.

In the present invention, the angiogenesis inhibitor also includes those angiogenesis inhibitors which undergo metabolism (such as oxidation, reduction, hydrolysis or conjugation) in the body. Further, in the present invention, the angiogenesis inhibitor also includes those compounds which produce angiogenesis inhibitor in the body as a result of metabolism (such as oxidation, reduction of hydrolysis).

(L) Anti-VEGF Antibody, Anti-FGF Antibody, Anti-PDGF Antibody and Anti-EGF Antibody In the present invention, anti-VEGF antibody is an antibody which has affinity for VEGF or a partial fragment thereof. Preferably, this anti-VEGF antibody is a neutralizing antibody that recognizes and binds to VEGF and thereby inhibits the vascular endothelial cell growth activity of VEGF. In the present invention, anti-VEGF antibody may be, for example, a polyclonal antibody monoclonal antibody, chimeric antibody, single-chain antibody (scFV) (Huston et al. (1988) Proc. Natl. Acad. Sci. USA 85: 5879-83; The Pharmacology of Monoclonal Antibody, vol. 113, Rosenburg and Moore ed., Springer Verlag (1994) pp. 269-315), humanized antibody, multispecific antibody (LeDoussal et al. (1992) Int. J. Cancer Suppl. 7: 58-62; Paulus (1985) Behring Inst. Mitt. 78: 118-32; Millstein and Cuello (1983) Nature 305: 537-9; Zimmermann (1986) Rev. Physiol. Biochem. Pharmacol. 105: 176-260; Van Dijk et al. (1989) Int. J. Cancer 43: 944-9), human antibody or an antibody fragment such as Fab, Fab', $F(ab')^2$, Fc or Fv. Preferably, a monoclonal antibody is used. Further, the anti-VEGF antibody may be modified with polyethylene glycol (PEG) or the like, if necessary. Further, the anti-VEGF antibody may be prepared as a fusion protein with β-galactosidase, MBP, GST, GFP or the like. Thus, it is possible to detect the anti-VEGF antibody without using a secondary antibody in methods such as ELISA. Alternatively, the anti-VEGF antibody may be labeled and modified with a substance such as biotin so that the antibody can be recovered with avidin, streptavidin, or the like.

The anti-VEGF antibody may be prepared by conventional methods using VEGF, a partial fragment thereof or a cell expressing one of them as a sensitizing antigen (Current Protocols in Molecular Biology, John Wiley & Sons (1987), Section 11.4-11.13). VEGF or a partial fragment thereof may be a fusion protein with Fc region, GST, MBP, GFP, AP or the like.

Polyclonal antibodies and monoclonal antibodies may be prepared by methods well known to those skilled in the art (Antibodies: A Laboratory Manual, E. Harlow and D. Lane, ed., Cold Spring Harbor Laboratory, Cold Spring Harbor, N.Y., 1988).

Briefly, polyclonal antibodies may be obtained, for example, by administering an antigen to a mammal such as mouse, rabbit, rat, etc., collecting blood from the mammal, isolating antibodies from the collected blood and purifying the antibodies. Methods of immunization are known to those skilled in the art. For example, immunization may be performed by administering an antigen once or more. The antigen (VEGF or a partial fragment thereof) may be dissolved in an appropriate buffer containing a conventionally used adjuvant (such as complete Freund's adjuvant or aluminium hydroxide). However, sometimes, no adjuvant is used depending on the administration routes or other conditions.

One or two months after the final immunization, blood is collected from the mammal and subjected to conventional methods such as centrifugation, precipitation with ammonium sulfate or polyethylene glycol, various chromatographics or the like for separation and purification. As a result, polyclonal antibodies are obtained as polyclonal antisera.

As a method for producing monoclonal antibodies, the hybridoma method may be given. First, a mammal is immunized in the same manner as in the production of polyclonal antibodies. After an appropriate number of days from the immunization, it is preferable to collect some blood and to measure the antibody titer by known methods such as ELISA.

Subsequently, the spleen is removed from the immunized animal after sensitization to obtain B cells. The B cells are fused to myeloma cells according to conventional procedures to thereby prepare antibody-producing hybridomas. The myeloma cell used for this purpose is not particularly limited, and known myeloma cells may be used. As a cell fusion method, any of known methods in the art (such as the Sendai virus method, polyethylene glycol method or protoplast method) may be used. The resultant hybridomas may be cultured in HAT medium (medium containing hypoxanthine, aminopterin and thymidine) for an appropriate period according to conventional methods to thereby select appropriate hybridomas. Subsequently, screening for hybridomas producing the antibody of interest is performed. Then, the resultant hybridoma can be cloned.

As a screening method, a known method for antibody detection (such as ELISA or radioimmunoassay) may be used. As a cloning method, a method known in the art (such as the limiting dilution method or FACS method) may be used. The resultant hybridoma may be cultured in an appropriate culture broth or administered to, for example, mouse which is compatible with the hybridoma intraperitoneally. From the thus obtained culture broth or abdominal dropsy, the monoclonal antibody of interest may be isolated and purified by such methods as salting out, ion exchange chromatography, gel filtration, affinity chromatography or the like.

In the present invention, as a preferable example of the anti-VEGF antibody, bevacizumab may be given. Bevacizumab is a human anti-VEGF monoclonal antibody and is sold by Genentech as Avastin™.

Bevacizumab may be obtained by purchasing Avastin™ from Genentech.

In the present invention, anti-FGF antibody is an antibody which has affinity for FGF or a partial fragment thereof. Preferably, the anti-FGF antibody is a neutralizing antibody which recognizes and binds to FGF and thereby inhibits the vascular endothelial cell growth activity of FGF. The anti-FGF antibody may be prepared in the same manner as described above for the preparation of anti-VEGF antibody.

In the present invention, anti-PDGF antibody is an antibody which has affinity for PDGF or a partial fragment thereof. Preferably, the anti-PDGF antibody is a neutralizing antibody which recognizes and binds to PDGF and thereby inhibits the vascular endothelial cell growth activity of PDGF. The anti-PDGF antibody may be prepared in the same manner as described above for the preparation of VEGF antibody.

In the present invention, anti-EGF antibody is an antibody which has affinity for EGF or a partial fragment thereof. Preferably, the anti-EGF antibody is a neutralizing antibody which recognizes and binds to EGF and thereby inhibits the vascular endothelial cell growth activity of EGF. The anti-EGF antibody may be prepared in the same manner as described above for the preparation of VEGF antibody.

4. Kit

The present invention provides a kit for use in the method of predicting the antitumor effect of angiogenesis inhibitors, comprising at least one antibody selected from the group consisting of anti-TGF-α antibody, anti-HB-EGF antibody, anti-EGF antibody, anti-epiregulin antibody, anti-EGF receptor antibody, anti-phosphorylated EGF receptor antibody and anti-phosphorylation antibody. Preferably, the antibody is anti-EGF receptor antibody or anti-phosphorylated EGF receptor antibody. The antibody may be prepared in the same manner as described above for the preparation of VEGF antibody. The antibody contained in the kit may be used for measuring the EGF dependency of a tumor cell for its proliferation and/or survival. The kit of the present invention may also comprise other components conventionally used in common measurement, in addition to the above antibody.

Further, the present invention provides a kit for use in the method of predicting the antitumor effect of angiogenesis inhibitors, comprising a polynucleotide complementary to at least a part of a transcript RNA from at least one gene selected from the group consisting of TGF-αgene, HB-EGF gene, EGF gene, epiregulin gene and EGF receptor gene. Preferably, the gene is EGF receptor gene. The polynucleotide which is a component of the kit of the present invention is a primer and/or a probe used, for example, in in situ hybridization, Northern blot analysis, DNA microarray, RT-PCR or the like. Such a polynucleotide may be designed using, for example, Primer Expression (Perkin-Elmer Applied Biosystems). A desired polynucleotide may be prepared by known methods. The polynucleotide contained in the kit may be used for measuring the EGF dependency of a tumor cell for its proliferation and/or survival. The kit of the present invention may also comprise other components conventionally used in common measurement, in addition to the above polynucleotide.

The nucleotide sequences of the above-mentioned genes are registered in various databases. For example, nucleotide sequence information may be available with the following GenBank accession numbers.

TGF-α gene: NM_003236
HB-EGF gene: NM_001945
EGF gene: NM_001963
Epiregulin gene: NM_001432
EGF receptor gene: NM_005228

The expression "at least a part of . . . RNA" refers to a nucleotide sequence with at least 15 bases, preferably 15-50 bases, more preferably 20-35 bases, still more preferably 20-30 bases. Those skilled in the art could appropriately select the length of the sequence.

5. Pharmaceutical Composition, Kit and Cancer Treatment Method

The present invention relates to a pharmaceutical composition, a kit and a method for treating cancer, each of which is characterized by a combination of a VEGF receptor kinase inhibitor and an EGF inhibitor.

In the present invention, the VEGF receptor kinase inhibitor is as described earlier in "3. Angiogenesis Inhibitors". Specific examples include those compounds represented by general formula (I). As a preferable example, 4-(3-chloro-4-(cyclopropylaminocarbonyl)aminophenoxy)-7-methoxy-6-quinolinecarboxamide may be given.

In the present invention, the EGF inhibitor is not particularly limited as long as it has inhibitory activity against EGF. Examples of the EGF inhibitor include, but are not limited to, EGF receptor kinase inhibitor and anti-EGF receptor antibody. Preferably, gefitinib, erlotinib, lapatinib, canertinib, pelitinib, AEE-788, HKI-272, cetuximab, panitumumab, matuzumab, nimotuzumab, IMC-11F8 and MDX-447 may be enumerated. More preferably, gefitinib, erlotinib and cetuximab may be enumerated. Particularly preferable is erlotinib.

In the present invention, the VEGF receptor kinase inhibitor and the EGF inhibitor encompass pharmacologically acceptable salts thereof and solvates of these inhibitors or the salts.

In the present invention, the expression "comprising a combination of" means a combination for using compounds jointly. This expression includes both forms of administration: (A) separate substances are applied together at the time of administration and (B) a mixture of two substances is administered.

The preparation contained in the kit of the present invention is not particularly limited in formulation as long as the preparation contains a VEGF receptor kinase inhibitor and/or an EGF inhibitor. The pharmaceutical composition and/or kit of the present invention is useful as a therapeutic pharmaceutical composition and/or kit for cancer treatment.

The pharmaceutical composition and/or kit and the method of treating cancers according to the present invention may be further combined with one or more other antitumor agents. Other antitumor agents are not particularly limited as long as they are preparations with antitumor effect. Specific examples of other antitumor agents include, but are not limited to, irinotecan hydrochloride (CPT-11), oxaliplatin, 5-fluorouracil (5-FU), docetaxel (Taxotere™), gemcitabine hydrochloride (Gemzar™), calcium folinate (Leucovorin) and bevacizumab (Avastin™). When the cancer to be treated is large bowel cancer, preferable examples of the other antitumor agent are irinotecan hydrochloride, oxaliplatin, 5-fluorouracil, calcium folinate and bevacizumab; when the cancer to be treated is pancreatic cancer, preferable examples of the other antitumor agent are gemcitabine hydrochloride and bevacizumab; when the cancer to be treated is renal cancer, bevacizumab is particularly preferable as the other antitumor agent; and when the cancer to be treated is lung cancer, docetaxel is particularly preferable as the other antitumor agent.

The pharmaceutical composition and/or kit of the present invention may be used as a therapeutic for cancers.

In the present invention, the term "therapeutic for cancers" includes antitumor agents, cancer prognosis improving agents, cancer recurrence preventing agents, cancer metastasis inhibiting agents and the like.

The effect of cancer treatment can be confirmed with X-ray photographs, observations on CT, histopathology of biopsy and levels of tumor markers.

The pharmaceutical composition and/or kit of the present invention may be administered to a mammal (e.g., human, rat, rabbit, sheep, pig, cattle, cat, dog, monkey, etc.).

The type of cancer to be treated with the therapeutic for cancers is not particularly limited. For example, brain tumor, neck cancer, esophageal cancer, tongue cancer, lung cancer, breast cancer, pancreatic cancer, gastric cancer, cancer of the intestine or duodenum, large bowel cancer (colon cancer, rectal cancer), bladder cancer, renal cancer, liver cancer, prostate cancer, uterine cancer, ovary cancer, thyroid cancer, gallbladder cancer, pharyngeal cancer, sarcoma (e.g., osteosarcoma, chondrosarcoma, Kaposi sarcoma, myosarcoma, angiosarcoma, fibrosarcoma or the like), leukemia (e.g., chronic myelogenous leukemia (CML), acute myelogenous leukemia (AML), chronic lymphocytic leukemia (CLL), acute lymphocytic leukemia (ALL), lymphoma, malignant lymphoma, multiple myeloma (MM) or the like), melanoma and so forth may be enumerated.

When the pharmaceutical composition and/or kit of the present invention is used, the composition and/or kit may be administered orally or parenterally. When the pharmaceutical composition and/or kit of the present invention is used, the dose of VEGF receptor kinase inhibitor varies depending on the degree of symptoms, the age, sexuality, body weight and sensitivity difference of the patient, method of administration, time of administration, interval of administration, the nature, prescription and type of pharmaceutical preparation, the type of active ingredient and so on, and is not particularly limited. Usually, the VEGF receptor kinase inhibitor may be administered at 0.1-1000 mg/day, preferably 0.5-100 mg/day, more preferably 1-30 mg/day, for adult (body weight: 60 kg). This amount may be administered once or divided into two or three administrations a day.

When the pharmaceutical composition and/or kit of the present invention is used, the dose of EGF receptor kinase inhibitor is not particularly limited. Usually, the EGF receptor kinase inhibitor may be administered at 0.1-6000 mg/day preferably 10-4000 mg/day, more preferably 50-2000 mg/day for adult. This amount may be administered once or divided into two or three administrations a day.

When the pharmaceutical composition and/or kit of the present invention is used, the dose of anti-EGF receptor antibody is not particularly limited. Usually, the anti-EGF receptor antibody may be administered at 1-6000 mg/day, preferably 10-2000 mg/day, more preferably 10-1000 mg/day. This amount may be administered once in one to seven days.

When the pharmaceutical composition and/or kit of the present invention is used, the dose of anti-EGF antibody is not particularly limited. Usually the anti-EGF antibody may be administered at 1-6000 mg/day, preferably 10-2000 mg/day, more preferably 10-1000 mg/day. This amount may be administered once in one to seven days.

The amount of VEGF receptor kinase inhibitor to be used is not particularly limited. This amount varies depending on individual combinations with an EGF inhibitor. For example, the amount of VEGF receptor kinase inhibitor is about 0.01- to 100-fold of the amount of EGF inhibitor (in weight ratio). More preferably, the amount is about 0.1- to 10-fold (in weight ratio).

The pharmaceutical composition of the present invention may be formulated into solid preparations for oral administration, injections or the like.

Further, the VEGF receptor kinase inhibitor and the EGF inhibitor contained in the kit of the present invention may be independently formulated into a solid preparation for oral administration, injection or the like.

When solid preparations for oral administration are prepared, excipients and, if necessary, binders, disintegrants, lubricants, coloring agents, flavoring/aromatic agents, etc. are added to a base component. Then, the resultant mixture may be made into tablets, coated tablets, granules, fine granules, powder, capsules and so on by conventional methods.

Examples of excipients include lactose, corn starch, white sugar, glucose, sorbitol, crystalline cellulose and silicon dioxide; examples of binders include polyvinyl alcohol, ethylcellulose, methylcellulose, gum arabic, hydroxypropylcellulose and hydroxypropylmethylcellulose; examples of lubricants include magnesium stearate, talc and silica; examples of coloring agents include those agents which are allowed to be added to pharmaceuticals; examples of flavoring/aromatic agents include cocoa powder, peppermint crystal, aromatic acid, peppermint oil, borneol and cinnamon powder. Needless to say, these tablets and granules may be appropriately coated with a sugar coating, gelatin coating or the like.

When injections are prepared, pH adjusting agents, buffers, dispersing agents dissolution aids, stabilizers, isotonizing agents, preservatives and so on are added to a base component, if necessary. Then, the resultant mixture may be made into intravenous injections, subcutaneous injections or intramuscular injections by conventional methods. If necessary, these injections may be made into freeze-dried products by conventional methods.

Examples of dispersing agents include methylcellulose, Polysorbate 80, hydroxyethylcellulose, gum arabic, Tragacanth powder, sodium carboxymethylcellulose and polyoxyethylene sorbitan monolaurate.

Examples of dissolution aids include polyoxyethylene hydrogenated castor oil, Polysorbate 80, nicotinamide, polyoxyethylene sorbitan monolaurate, macrogol and castor oil fatty acid ethyl ester.

Examples of stabilizers include sodium sulfite and sodium metasulfite; and examples of preservatives include methyl paraoxybenzoate, ethyl paraoxybenzoate, sorbic acid, phenol, cresol and chlorocresol.

In the kit of the present invention, a preparation comprising a VEGF receptor kinase inhibitor and a preparation comprising an EGF inhibitor may be in the form of a mixture. Alternatively, the two preparations may be packed separately in one wrapping container. When these two preparations are packed separately, the order of administration is not particularly limited. The two preparations may be administered simultaneously. Alternatively, one of them may be administered first.

The pharmaceutical composition and/or kit of the present invention may comprise, in addition to the above-described VEGF receptor kinase inhibitor and EGF inhibitor, a wrapping container, a handling instruction, an accompanying document or the like. In the wrapping container, handling instruction, accompanying document or the like, combinations of substances for combined application may be described. Also, for each of the embodiments (A) separate substances are applied together at the time of administration and (B) the substances are administered as a mixture, usage and dose may be described. The usage and dose may be described in reference to the description provided above.

In another embodiment, the kit of the present invention may comprise the following (a) and (b): (a) at least one selected from the group consisting of a wrapping container, a handling instruction and an accompanying document, each of which is stating that a VEGF receptor kinase inhibitor and an EGF inhibitor are to be used in combination, and (b) a pharmaceutical composition comprising a VEGF receptor kinase inhibitor. Such a kit is useful as a kit for treating cancers. The pharmaceutical composition comprising a VEGF receptor kinase inhibitor is useful as a pharmaceutical composition for treating cancers. In the wrapping container, the handling instruction or the accompanying document, combined application of compounds may be described. For each of the embodiments (A) separate substances are applied together at the time of administration and (B) the substances are administered as a mixture, usage and dose may be described. The usage and dose may be described in reference to the description provided above.

Further, the present invention includes use of a VEGF receptor kinase inhibitor in preparing a pharmaceutical composition comprising a combination with an EGF inhibitor. In the use of the present invention, the pharmaceutical composition is useful as a pharmaceutical composition for treating cancers.

Further, the present invention also includes a VEGF receptor kinase inhibitor for use in a pharmaceutical composition comprising a combination with an EGF inhibitor.

Further, the present invention also includes a method of treating cancers, which is characterized by administering to a patient a VEGF receptor kinase inhibitor and an EGF inhibitor simultaneously or at different times. In the method of treating cancers of the present invention, the administration route and administration method for the VEGF receptor kinase inhibitor and EGF inhibitor are not particularly limited. For the administration route and administration method, the description provided for the pharmaceutical composition of the present invention may be consulted.

Further, the present invention also includes a pharmaceutical composition comprising a VEGF receptor kinase inhibitor, characterized by being administered to a patient with a EGF inhibitor simultaneously or at a different time. In the pharmaceutical composition of the present invention, the administration route and administration method for the VEGF receptor kinase inhibitor and EGF inhibitor are not particularly limited. For the administration route and administration method, the description provided for the pharmaceutical composition of the present invention may be consulted.

EXAMPLES

Hereinbelow, the present invention will be described more specifically with reference to the following Examples. However, the present invention is not limited to these Examples.

Example 1

Anti-Tumor Effect of VEGF Receptor Kinase Inhibitor in Human Tumor Cell Line Subcutaneous Xenograft Models (In Vivo)

Human tumor cell lines MDA-MB-231, MDA-MB-468, DU145, AsPC-1 (these four lines were purchased from ATCC), A549 (purchased from Dainippon Pharmaceutical Co., Ltd.), Lovo, SK-OV-3, H526, PC-3, DLD-1, HCT116 (these six lines were purchased from ATCC), SEKI, HMV-1 (these two lines were purchased from JCRB cell bank, National Institute of Biomedical Innovation), LOX (purchased from AntiCancer) and A375 (purchased from Dainippon Pharmaceutical Co., Ltd.) were cultured with RPMI1640 (containing 10% FBS) in a 5% $CO_2$ gas incubator until they reached about 80% confluence. After culturing, cells from each line were recovered with trypsin-EDTA by conventional procedures. The cells were suspended in phosphate buffer to prepare a cell suspension of $1 \times 10^8$ cells/ml or $5 \times 10^7$ cells/ml. Subsequently, 0.1 ml of the cell suspension was subcutaneously transplanted on the flank of each nude mouse. After transplantation, when the tumor volume reached about 100-200 $mm^3$, administration of 4-(3-chloro-4-(cyclopropylaminocarbonyl)aminophenoxy)-7-methoxy-6-quinolinecarboxamide (a methanesulfonate) (100 mg/kg; twice a day; one week; oral administration) was started. The 4-(3-chloro-4-(cyclopropylaminocarbonyl)aminophenoxy)-7-methoxy-6-quinolinecarboxamide (a methanesulfonate) was prepared based on the disclosure in WO 02/32872 and WO 2005/063713. The major axis and minor axis of tumor were measured with a Digimatic Caliper (Mitsutoyo). Then, tumor volume, relative tumor volume and ΔT/C were calculated using the following formulas:

Tumor volume(TV)=tumor major axis (mm)×tumor minor axis$^2$ (mm$^2$)/2

Relative tumor volume(RETV)=tumor volume on the measurement day/tumor volume on the starting day of administration ΔT/C=(tumor volume at day 8 of administration groups−tumor volume at day 1 of administration groups)/(tumor volume at day 8 of control group−tumor volume at day 1 of control group)×100

In the above formulas, "day 1" means the day when administration started and "day 8" means the 8th day from the start of the administration.

Depending on the intensity of the antitumor effect of 4-(3-chloro-4-(cyclopropylaminocarbonyl)aminophenoxy)-7-methoxy-6-quinolinecarboxamide, individual tumor cell lines were classified into high sensitivity lines, medium sensitivity lines and low sensitivity lines. Tumor cell lines which showed ΔT/C<−30% (MDA-MB-231, MDA-MB-468 and DU145) were classified as high sensitivity lines; tumor cell lines which showed −30%<ΔT/C<10% (AsPC-1, A549, Lovo and SK-OV-3) were classified as medium sensitivity lines; and tumor cell lines which showed 10%<ΔT/C(H526, PC-3, DLD-1, HCT116, SEKI, HMV-1, LOX and A375) were classified as low sensitivity lines.

Example 2

Analysis of the Expression Levels of EGF Receptor and the State of Phosphorylation of Tyrosine Residues Thereof (pY1068, pY1148) in Human Tumor Cell Line Subcutaneous Xenograft Models (In Vivo)

Human tumor cell lines MDA-MB-231, MDA-MB-468, DU145, AsPC-1 (these four lines were purchased from ATCC), A549 (purchased from Dainippon Pharmaceutical Co., Ltd.), Lovo, SK-OV-3, H526, PC-3, DLD-1, HCT116 (these six lines were purchased from ATCC), SEKI, HMV-1 (these two lines were purchased from JCRB cell bank, National Institute of Biomedical Innovation), LOX (purchased from AntiCancer) and A375 (purchased from Dainippon Pharmaceutical Co., Ltd.) were cultured with RPMI1640 (containing 10% FBS) in a 5% $CO_2$ gas incubator until they reached about 80% confluence. After culturing, cells from each line were recovered with trypsin-EDTA by conventional procedures. The 15 types of tumor cells (MDA-MB-231, MDA-MB-468, DU145, AsPC-1, A549, Lovo, SK-OV-3, H526, PC-3, DLD-1, HCT116, SEKI, HMV-1, LOX and A375) were subcutaneously transplanted into nude mice at $3$-$10 \times 10^6$ cells/mouse. When the tumor volume expanded to about 100-200 $mm^3$, each tumor was resected. Then, tumor cell lysates were prepared with a cell lysis solution containing various protease inhibitors (Leupeptin, p-APMSF, EDTA, o-NaVO4) and 10% glycerol.

For each of the thus prepared tumor cell lysates, a specific amount of protein (20 μg or 8 μg) was fractionated by SDS-PAGE and transferred onto a nitrocellulose membrane (Hybond ECL; Amersham Bioscience). Then, Western blotting was performed by conventional methods using anti-EGF receptor antibody (Santa Cruz Biotechnology), anti-EGF receptor pY1068 antibody (anti-EGF receptor tyrosine phosphorylation antibody) (Cell Signaling) and anti-EGF receptor pY1148 antibody (anti-EGF receptor tyrosine phosphorylation antibody) (Cell Signaling).

Then, the expression levels of EGF receptor and the degrees of phosphorylation thereof in individual cell lines were compared with the sensitivity to 4-(3-chloro-4-(cyclopropylaminocarbonyl)aminophenoxy)-7-methoxy-6- quinolinecarboxamide in those cell lines. As a result, a substantial amount of expression of EGF receptor and/or phosphorylation thereof was recognized in 6 lines out of the 7 high sensitivity and medium sensitivity tumor cell lines, whereas a substantial amount of expression of EGF receptor and/or phosphorylation thereof was recognized in only one line out of the 8 low sensitivity tumor cell lines (FIG. 1).

Since it is believed that the expression level of EGF receptor and/or the degree of phosphorylation thereof in tumor cells indicates the EGF dependency of individual cell lines for their proliferation and/or survival, tumor cell lines with higher EGF dependency (i.e., cell lines which were classified into high sensitivity and medium sensitivity lines in Example 1) have been found to be more sensitive to 4-(3-chloro-4-(cyclopropylaminocarbonyl)aminophenoxy)-7-methoxy-6-quinolinecarboxamide.

Therefore, it has become clear that the antitumor effect of an angiogenesis inhibitor can be predicted by evaluating the EGF dependency of a tumor cell of interest for its proliferation and/or survival and using the resultant EGF dependency as an indicator.

Example 3

Combined Application of VEGF Receptor Kinase Inhibitor and EGF Inhibitor in Human Non-Small Cell Lung Cancer Cell Line (A549) Subcutaneous Xenograft Model (In Vivo)

Human non-small cell lung cancer cell line A549 (purchased from Dainippon Pharmaceutical Co., Ltd.) was cultured at 37° C. with RPMI1640 (containing 10% FBS) in a 5% $CO_2$ gas incubator until cells reached about 80% confluence. Then, cells were recovered with trypsin-EDTA. A cell suspension ($5 \times 10^7$ cells/ml) was prepared with phosphate buffer containing 50% matrigel. The resultant cell suspension was subcutaneously transplanted into the flank of nude (0.1 ml/mouse). From day 10 of transplantation, 4-(3-chloro-4-(cyclopropylaminocarbonyl)aminophenoxy)-7-methoxy-6-quinolinecarboxamide (a methanesulfonate) and erlotinib were orally administered independently or in combination. With respect to 4-(3-chloro-4-(cyclopropylaminocarbonyl) aminophenoxy)-7-methoxy-6-quinolinecarboxamide (a methanesulfonate), it was administered at 3 mg/kg, 10 mg/kg or 30 mg/kg; once a day; for 4 weeks. With respect to erlotinib, it was administered at 50 mg/kg, once a day, for 4 weeks. The major axis and minor axis of tumor were measured with a Digimatic Caliper (Mitsutoyo). Then, tumor volume and relative tumor volume were calculated using the following formulas:

Tumor volume(TV)=tumor major axis (mm)×tumor minor axis$^2$ (mm$^2$)/2

Figure 2:
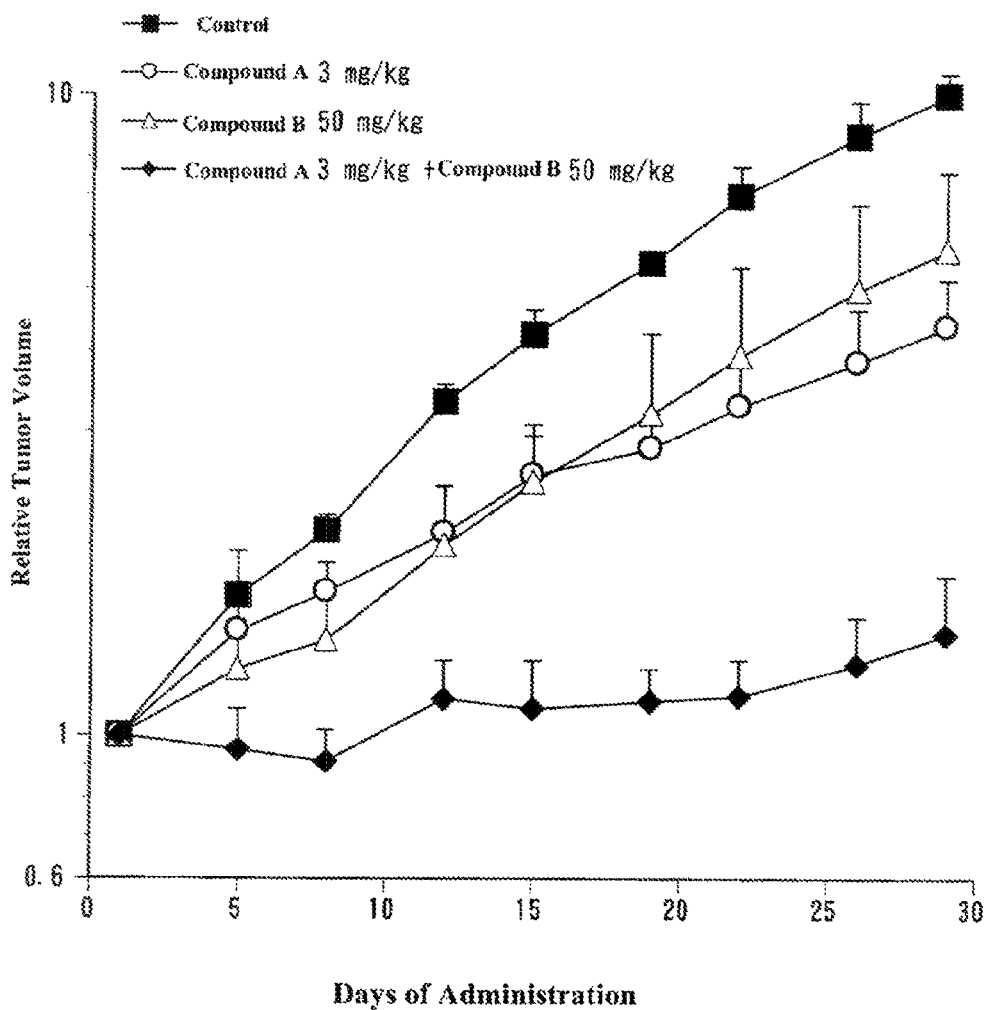
FIG. 2 shows the effect of combined administration of a VEGF receptor kinase inhibitor and an EGF inhibitor in a model in which a human non-small-cell lung cancer cell line (A549) was subcutaneously transplanted.
Figure 3:
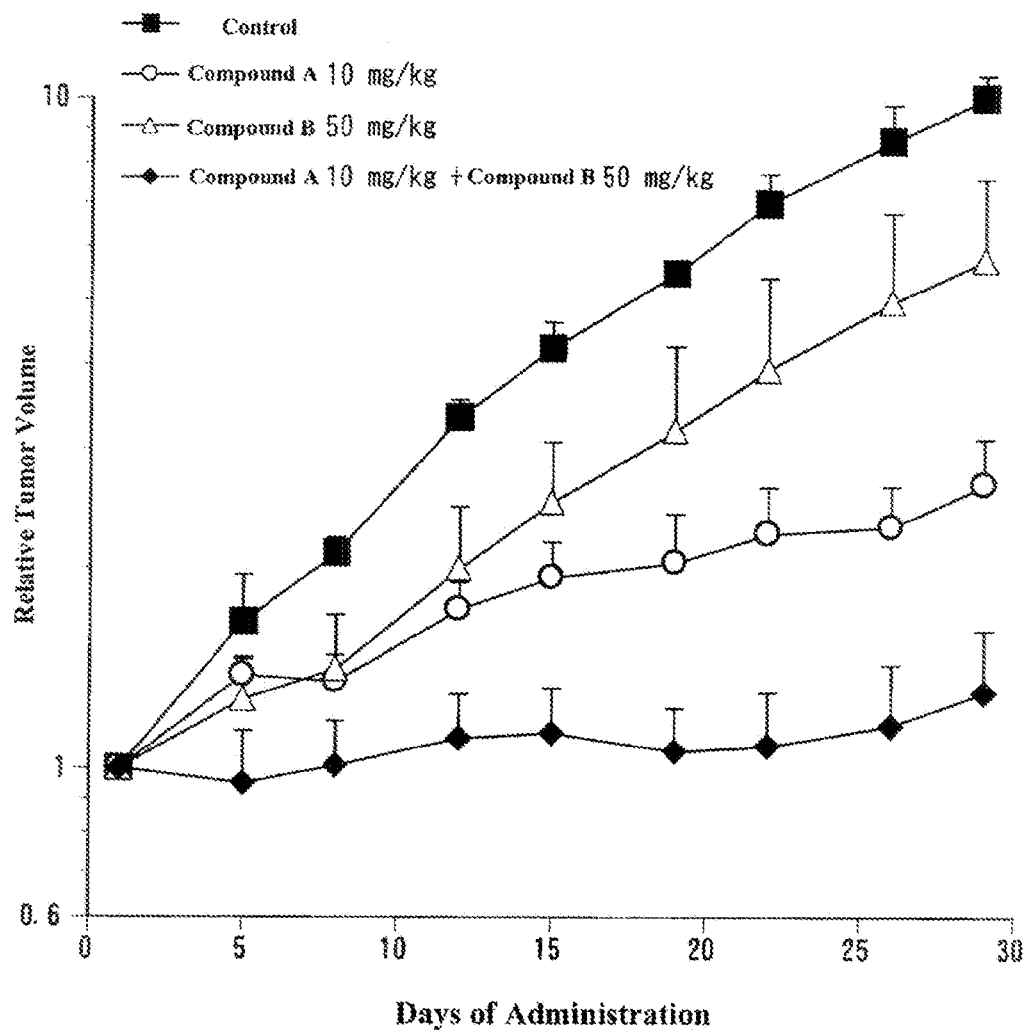
FIG. 3 shows the effect of combined administration of a VEGF receptor kinase inhibitor and an EGF inhibitor in a model in which a human non-small-cell lung cancer cell line (A549) was subcutaneously transplanted.
Figure 4:
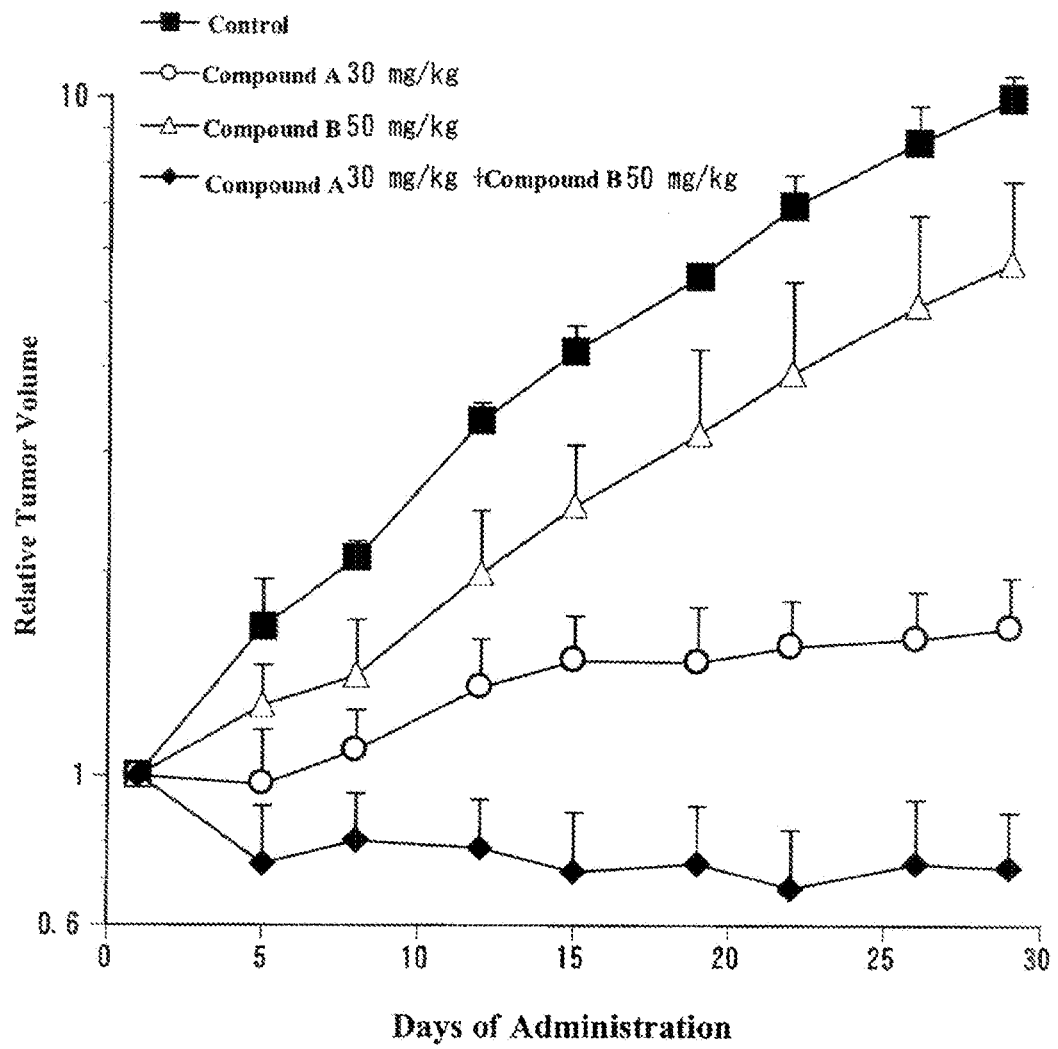
FIG. 4 shows the effect of combined administration of a VEGF receptor kinase inhibitor and an EGF inhibitor in a model in which a human non-small-cell lung cancer cell line (A549) was subcutaneously transplanted.

Relative tumor volume(RTV)=tumor volume on the measurement day/tumor volume on the starting day of administration As a result, by combining 4-(3-chloro-4-(cyclopropylaminocarbonyl)aminophenoxy)-7-methoxy-6-quinolinecarboxamide (Compound A) with erlotinib (Compound B), an excellent antitumor effect was obtained, compared to their effects produced independently (see Tables 1 to 3 and FIGS. 2 to 4). Further, the combined application of 4-(3-chloro-4-(cyclopropylaminocarbonyl)aminophenoxy)-7-methoxy 6-quinolinecarboxamide and erlotinib produced an excellent antitumor effect (such as tumor reduction effect) which erlotinib alone cannot produce (see Tables 1 to 3 and FIGS. 2 to 4).

TABLE 1

| Compound Administration | | Relative Tumor Volume at Day 29 Mean ± Standard Deviation |
|---|---|---|
| Control (no treatment) | | 9.94 ± 0.77 |
| Erlotinib | 50 mg/kg | 5.71 ± 1.84 |
| Compound A | 3 mg/kg | 4.34 ± 0.80 |
| Compound A +Erlotinib | 3 mg/kg 50 mg/kg | 1.44 ± 0.34 |

Table 1 shows the antitumor effects produced by 4-(3-chloro-4-(cyclopropylaminocarbonyl)aminophenoxy)-7-methoxy-6-quinolinecarboxamide (indicated as Compound A in Table 1), erlotinib and a combined application of these two compounds in a human non-small cell lung cancer cell line (A549) subcutaneous xenograft model. The day when administration was started is counted as day 1.

TABLE 2

| Compound Administration | | Relative Tumor Volume at Day 29 Mean ± Standard Deviation |
|---|---|---|
| Control (no treatment) | | 9.94 ± 0.77 |
| Erlotinib | 50 mg/kg | 5.71 ± 1.84 |
| Compound A | 10 mg/kg | 2.65 ± 0.45 |
| Compound A +Erlotinib | 10 mg/kg 50 mg/kg | 1.30 ± 0.31 |

Table 2 shows the antitumor effects produced by 4-(3-chloro-4-(cyclopropylaminocarbonyl)aminophenoxy)-7-methoxy-6-quinolinecarboxamide (indicated as Compound A in Table 2), erlotinib and a combined application of these two compounds in a human non-small cell lung cancer cell line (A549) subcutaneous xenograft model. The day when administration was started is counted as day 1.

TABLE 3

| Compound Administration | | Relative Tumor Volume at Day 29 Mean ± Standard Deviation |
|---|---|---|
| Control (no treatment) | | 9.94 ± 0.77 |
| Erlotinib | 50 mg/kg | 5.71 ± 1.84 |
| Compound A | 30 mg/kg | 1.65 ± 0.31 |
| Compound A +Erlotinib | 30 mg/kg 50 mg/kg | 0.73 ± 0.15 |

Table 3 shows the antitumor effects produced by 4-(3-chloro-4-(cyclopropylaminocarbonyl)aminophenoxy)-7-methoxy-6-quinolinecarboxamide (indicated as Compound A in Table 3), erlotinib and a combined application of these two compounds in a human non-small cell lung cancer cell line (A549) subcutaneous xenograft model. The day when administration was started is counted as day 1.

Example 4

Combined Application of VEGF Receptor Kinase Inhibitor and EGF Inhibitor in Human Non-Small Cell Lung Cancer Cell Strain (PC-9) Subcutaneous Xenograft Model (In Vivo)

Human non-small cell lung cancer cell strain PC-9 (purchased from Immuno-Biological Laboratories Co., Ltd.) was cultured at 37° C. with RPMI1640 (containing 10% FBS) in a 5% $CO_2$ gas incubator until cells reached about 80% confluence.

Then, cells were recovered with trypsin-EDTA. A cell suspension ($5 \times 10^7$ cells/ml) was prepared with phosphate buffer.

The resultant cell suspension was subcutaneously transplanted into the flank of nude mice (0.1 ml/mouse). From day 13 of transplantation, 4-(3-chloro-4-(cyclopropylaminocarbonyl)aminophenoxy)-7-methoxy-6-quinolinecarboxamide (a methanesulfonate) (10 mg/kg, once a day, 4 weeks) and erlotinib (50 mg/kg, once a day, 4 weeks) were orally administered independently or in combination. The major axis and minor axis of tumor were measured with a Digimatic Caliper (Mitsutoyo). Then, tumor volume and relative tumor volume were calculated using the following formulas:

Tumor volume(TV)=tumor major axis (mm)×tumor minor axis$^2$ (mm$^2$)/2

Relative tumor volume(RTV)=tumor volume on the measurement day/tumor volume on the starting day of administration When a statistically significant interaction was recognized in the combined application group by two-way ANOVA analysis, such interaction was judged synergistic effect.

Figure 5:
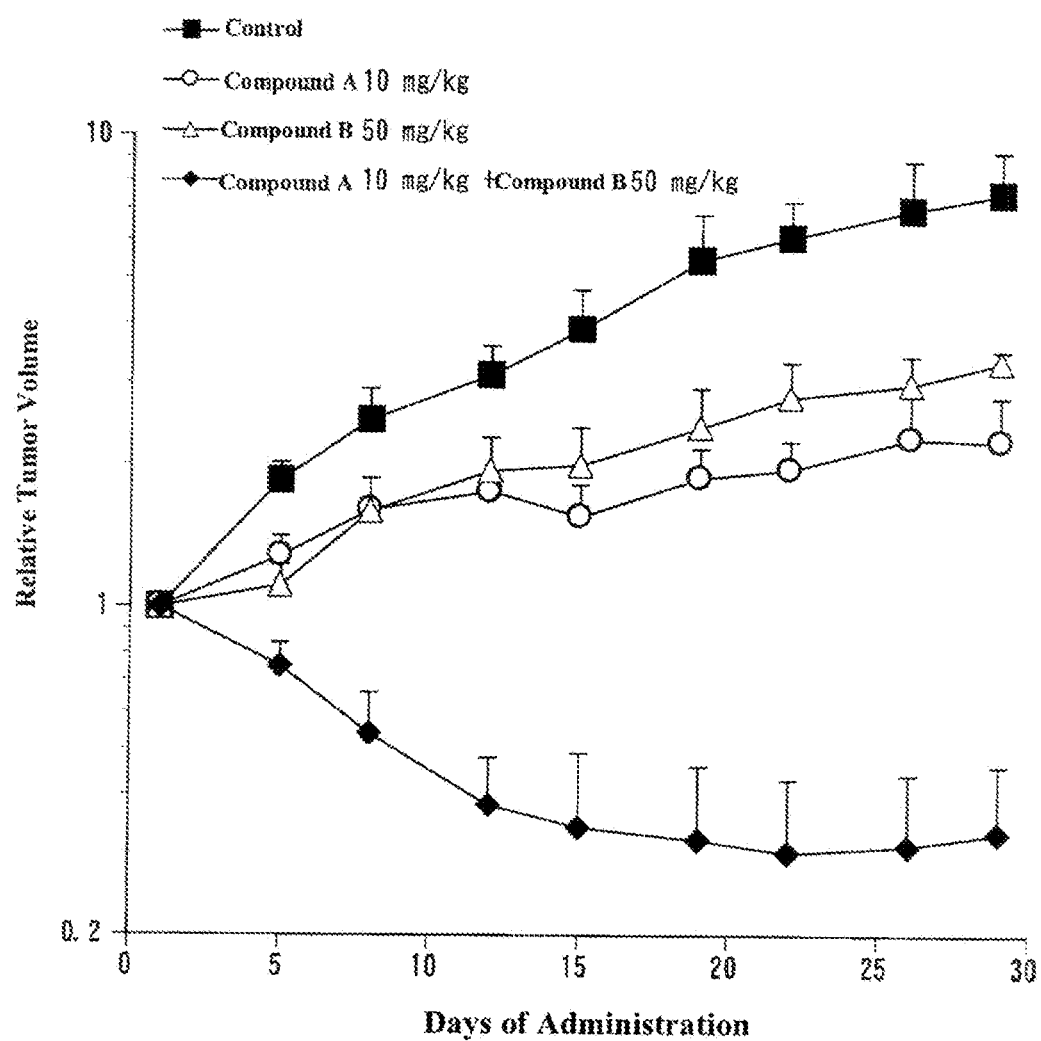
FIG. 5 shows the effect of combined administration of a VEGF receptor kinase inhibitor and an EGF inhibitor in a model in which a human non-small-cell lung cancer cell line (PC-9) was subcutaneously transplanted.

As a result, by combining 4-(3-chloro-4-(cyclopropylaminocarbonyl)aminophenoxy)-7-methoxy-6-quinolinecarboxamide (Compound A) with erlotinib (Compound B), a synergistic effect was observed. The combined application of these compounds produced excellent antitumor effect compared to their effects produced independently (see Table 4 and FIG. 5). Further, by combining 4-(3-chloro-4-(cyclopropylaminocarbonyl)aminophenoxy)-7-methoxy-1-quinolinecarboxamide with erlotinib, an excellent antitumor effect (such as tumor reduction effect) which erlotinib alone cannot produce was observed (see Table 4 and FIG. 5).

It should be noted here that an activation mutation of EGF receptor is recognized in PC-9. It is a tumor cell line in which phosphorylation of EGF receptor has been enhanced.

Considering from what has been described, it is believed that the pharmaceutical composition of the present invention comprising a combination of a VEGF receptor kinase inhibitor and an EGF inhibitor produces more antitumor effect against tumor cells with higher EGF dependency for their proliferation and/or survival.

TABLE 4

| Compound Administration | | Relative Tumor Volume at Day 29 Mean ± Standard Deviation | Two-way ANOVA |
|---|---|---|---|
| Control (no treatment) | | 7.51 ± 1.69 | |
| Compound A | 10 mg/kg | 2.24 ± 0.54 | |
| Erlotinib | 50 mg/kg | 3.30 ± 0.19 | |
| Compound A +Erlotinib | 10 mg/kg 50 mg/kg | 0.33 ± 0.13 | p < 0.01 Synergistic effect |

Table 4 shows the antitumor effects produced by 4-(3-chloro-4-(cyclopropylaminocarbonyl)aminophenoxy)-7-methoxy-6-quinolinecarboxamide (indicated as Compound A in Table 4), erlotinib and the combined application of 4-(3-chloro-4-(cyclopropylaminocarbonyl)aminophenoxy)-7-methoxy-6-quinolinecarboxamide and erlotinib. The day when administration was started is counted as day 1.

From these results, a pharmaceutical composition and a kit with excellent antitumor effect have been provided by combining 4-(3-chloro-4-(cyclopropylaminocarbonyl)aminophenoxy)-7-methoxy-6-quinolinecarboxamide with erlotinib, and it has become possible to use such a pharmaceutical composition and a kit for treatment of cancers.

REFERENCE EXAMPLE

Hereinbelow, a method of producing a preparation of 4-(3-chloro-4-(cyclopropyl aminocarbonyl)aminophenoxy)-7-methoxy-6-quinolinecarboxamide, one of VEGF receptor kinase inhibitors, will be described as a reference example.

(Production of Pharmaceutical Composition)

(1) 1 mg Tablets

Crystals of a methanesulfonate of 4-(3-chloro-4-(cyclopropylaminocarbonyl)aminophenoxy)-7-methoxy-6-quinolinecarboxamide (C) (hereinafter, sometimes referred to as "crystal (C)"; the crystal (C) was prepared according to the method described in Example 7 of WO 2005/063713) (24 g) and light silicic anhydride (antigelling agent; product name: AEROSIL™ 200; Nippon Aerosil) (192 g) were mixed in a 20 L super-mixer. To the resultant mixture, 1236 g of D-mannitol (excipient; Towa Chemical Industry), 720 g of crystalline cellulose (excipient; product name: Avicel™ PH101; Asahi Kasei Corporation) and 72 g of hydroxypropylcellulose (binder; product name: HPC-L; Nippon Soda) were added and mixed. Subsequently an appropriate amount of absolute ethanol was added thereto to thereby obtain crystal (C)-containing rude granules. These rude granules were dried in a shelf-type dryer (60° C.) and processed in a power mill to thereby obtain granules. Together with these granules, 120 g of croscarmellose sodium (disintegrant; product name: Ac-Di-Sol; FMC International Inc.) and 36 g of sodium stearyl fumarate (lubricant; JRS Pharma LP) were put in a 20 L tumbler mixer and mixed. The resultant mixture was processed with a tableting machine to thereby obtain tablets with a total mass of 100 mg/tablet. Further, the tablets were coated with an aqueous solution of 10% Opadry Yellow (Opadry 03F42069 Yellow; Colorcon Japan) using a tablet coating machine to thereby obtain coated tablets with a total mass of 105 mg/tablet.

(2) 10 mg Tablets

Crystal (C) (60 g) and light silicic anhydride (antigelling agent; product name: AEROSIL™200; Nippon Aerosil) (192 g) were mixed in a 20 L super-mixer. To the resultant mixture, 1200 g of D-mannitol (excipient; Towa Chemical Industry), 720 g of crystalline cellulose (excipient; product name: Avicel™ PH101; Asahi Kasei Corporation) and 72 g of hydroxypropylcellulose (binder; product name: HPC-L; Nippon Soda) were added and mixed. Subsequently an appropriate amount of absolute ethanol was added thereto to thereby obtain crystal (C)-containing rude granules. These rude granules were dried in a shelf-type dryer (60° C.) and processed in a power mill to thereby obtain granules. Together with these granules, 120 g of croscarmellose sodium (disintegrant; product name: Ac-Di-Sol; FMC International Inc.) and 36 g of sodium stearyl fumarate (lubricant; JRS Pharma LP) were put in a 20 L tumbler mixer and mixed. The resultant mixture was processed with a tableting machine to thereby obtain tablets with a total mass of 400 mg/tablet. Further, the tablets were coated with an aqueous solution of 10% Opadry Yellow (Opadry 03F42069 Yellow; Colorcon Japan) using a tablet coating machine to thereby obtain coated tablets with a total mass of 411 mg/tablet.

(3) 100 mg Tablets

Crystal (C) (31.4 g) and light silicic anhydride (antigelling agent; product name: AEROSIL™ 200; Nippon Aerosil) (4 g) were mixed in a 1 L super-mixer. To the resultant mixture, 40.1 g of anhydrous dibasic calcium phosphate (excipient; Kyowa Chemical Industry), 10 g of low-substituted hydroxypropylcellulose (binder; product name: L-HPC (LH-21); Shin-Etsu Chemical) and 3 g of hydroxypropylcellulose (binder; product name: HPC-L; Nippon Soda) were added and mixed. Subsequently an appropriate amount of absolute ethanol was added thereto to thereby obtain crystal (C)-containing rude granules. These rude granules were dried in a shelf-type dryer (60° C.) and processed in a power mill to thereby obtain granules. Together with these granules, 10 g of croscarmellose sodium (disintegrant; product name: Ac-Di-Sol; FMC International Inc.) and 1.5 g of sodium stearyl fumarate (lubricant; JRS Pharma LP) were mixed. The resultant mixture was processed with a tableting machine to thereby obtain tablets with a total mass of 400 mg/tablet.

INDUSTRIAL APPLICABILITY

According to the present invention, a method of predicting the antitumor effect of angiogenesis inhibitors has been provided.

More specifically, it has become possible to predict the antitumor effect of angiogenesis inhibitors by evaluating the EGF dependency of a tumor cell of interest for its proliferation and/or survival and by using the EGF dependency as an indicator.

Since the method according to the present invention is capable of predicting the antitumor effect of angiogenesis inhibitors without administering those agents to patients, it is possible to select and treat those patients who are expected to show higher antitumor effect. Thus, it has become possible to contribute to patients' QOL.

Further, according to the present invention, a pharmaceutical composition and/or a kit comprising a combination of a VEGF receptor kinase inhibitor and an EGF inhibitor has been provided, and it has become possible to use such a pharmaceutical composition and/or a kit for treating cancers.

The invention claimed is:

1. A method for treating an EGF-dependent cancer, which method comprises administering, to a patient in need thereof, an effective amount of a VEGF receptor kinase inhibitor in combination with an effective amount of a substance having EGF inhibitory activity, wherein the VEGF receptor kinase inhibitor is a compound selected from the group consisting of:

4-(3-chloro-4-(cyclopropylaminocarbonyl)aminophenoxy)-7-methoxy-6-quinolinecarboxamide,
4-(3-chloro-4-(ethylaminocarbonyl)aminophenoxy)-7-methoxy-6-quinolinecarboxamide,
N6-methoxy-4-(3-chloro-4-(((cyclopropylamino)carbonyl)amino)phenoxy)-7-methoxy-6-quinolinecarboxamide,
4-(3-chloro-4-(methylaminocarbonyl)aminophenoxy)-7-methoxy-6-quinolinecarboxamide,
N6-methoxy-4-(3-chloro-4-(((ethylamino)carbonyl)amino)phenoxy)-7-methoxy-6-quinolinecarboxamide and
pharmacologically acceptable salts and solvates thereof; and
wherein the substance having EGF inhibitor activity is at least one compound selected from the group consisting of:
4-(3-chloro-4-fluorophenylamino)-7-methoxy-6-(3-(4-morpholino) propoxy-quinazoline),
4-(3-ethynylphenylamino)-6,7-bis(2-methoxyethoxy)-quinazoline,
N-[3-chloro-4-[(3-fluorobenzyl)oxy]phenyl]-6-[5-[[[2-(methylsulfonyl)ethyl]-amino]methyl]furan-2-yl]quinazoline-4-amine,
N-[4-[N-(3-chloro-4-fluorophenyl)amino]-7-[3-(4-morpholinyl)propoxy]-quinazoline-6-yl]acrylamide,
(2E)-N-[4-[(3-chloro-4-fluorophenyl)amino]-3-cyano-7-ethoxy-6-quinolinyl]-4-(dimethylamino)-2-butenamide,
[6-[4-[(4-ethylpiperazine-1-yl)methyl]phenyl]-7H-pyrrolo[2,3-d]pyrimidine-4-yl]-((R)-1-phenylethyl)amine,
(E)-N-{4-[3-chloro-4-(2-pyridinylmethoxy)anilino]-3-cyano-7-ethoxy-6-quinolinyl}-4-(dimethylamino)-2-butenamide and
pharmacologically acceptable salts and solvates thereof.

2. The method according to claim 1, wherein the VEGF receptor kinase inhibitor is 4-(3-chloro-4-(cyclorpopylaminocarbonyl)aminophenoxy)-7-methoxy-6-quinolinecarboxamide, a pharmacologically acceptable salt thereof, or a solvate of said compound or salt.

3. The method according to claim 1, wherein the VEGF receptor kinase inhibitor is a methanesulfphonic acid salt of 4-(3-chloro-4-(cyclorpopylaminocarbonyl)aminophenoxy)-7-methoxy-6-quinolinecarboxamide.

4. The method according to claim 1, wherein the substance having EGF inhibitor activity is 4-(3-ethynylphenylamino)-6,7-bis(2-methoxyethoxy)-quinazoline, a pharmacologically acceptable salt thereof, or a solvate of said compound or salt.

* * * * *

UNITED STATES PATENT AND TRADEMARK OFFICE
CERTIFICATE OF CORRECTION

| | | |
|---|---|---|
| PATENT NO. | : 8,969,344 B2 | Page 1 of 1 |
| APPLICATION NO. | : 13/624278 | |
| DATED | : March 3, 2015 | |
| INVENTOR(S) | : Junji Matsui, Yuji Yamamoto and Toshimitsu Uenaka | |

It is certified that error appears in the above-identified patent and that said Letters Patent is hereby corrected as shown below:

Title page, item (62) (Related U.S. Application Data)
Line 1, delete "Division" and replace it with --Continuation--.

Title page, item (57) (Abstract)
Line 4, delete "EOF" and replace it with --EGF--.

In the Specification,
Column 1, Line 7
Delete "divisional" and replace it with --continuation--.

In the Claims,
Column 62, claim 3
Line 36, delete "methanesulfphonic" and replace it with --methanesulfonic--.

Signed and Sealed this
Eighteenth Day of August, 2015

Michelle K. Lee
*Director of the United States Patent and Trademark Office*